(12) United States Patent
Frants et al.

(10) Patent No.: US 6,825,332 B1
(45) Date of Patent: Nov. 30, 2004

(54) GENE RELATED TO MIGRAINE IN MAN

(75) Inventors: Rune Robert Isak Erik Frants, Hoofddorp (NL); Michel Dominique Ferrari, Oegstgeest (NL); Gisela Marie Terwindt, Heemstede (NL); Roel André Ophoff, Leiden (NL)

(73) Assignee: Rijksuniversiteit Tel Leiden, Leiden (NL)

( * ) Notice: Subject to any disclaimer, the term of this patent is extended or adjusted under 35 U.S.C. 154(b) by 0 days.

(21) Appl. No.: 09/269,446

(22) PCT Filed: Sep. 26, 1997

(86) PCT No.: PCT/NL97/00538

§ 371 (c)(1),
(2), (4) Date: May 27, 1999

(87) PCT Pub. No.: WO95/04822

PCT Pub. Date: Feb. 16, 1995

(30) Foreign Application Priority Data

Sep. 27, 1996 (NL) ............................................ 96202707

(51) Int. Cl.[7] .......................... C07H 21/04; C07H 21/02
(52) U.S. Cl. ...................................... 536/23.5; 536/23.1
(58) Field of Search .............................. 435/320.1, 325, 435/455; 536/23.1, 23.5; 424/93.2, 93.21

(56) References Cited

FOREIGN PATENT DOCUMENTS

WO    WO 95 04822 A    2/1995

OTHER PUBLICATIONS

Ellis et. al.; GenBank Seq. No. AAQ84660, 1995. 5–8.*
Ellis et. al.; GenBank Seq. No. AAQ84660, 1995,5–9.*
Skolnick et. al.; From genes to protein struture and function: novel applications of computational approaches in the genomic era, 2000, TIBETECH, vol. 18: 34–39.*
Kaye et. al.; A single amino acid substitution results in a retinoblastoma protein defective in phosphorylation and oncoprotein binding, 1990, Proc. Natl. Acad. Sci., vol. 87: 6922–6926.*
Rudinger; Characteristics of the amino acids as components of a peptide hormone sequence, 1976, Peptide Hormones: 1–7.*
Ellis et al., AC Q84659, Feb. 16, 1995, Gene seq. 36.*
Opoff, R.A., AC Z80116, Nov. 01, 1996, Gene Embl.*
Ophoff R A et al. (Oct 24–28, 1995) *Am J of Human Genetics* 57 (4 Suppl.).
N. Soldatov (1994) *Genomics* 22:77–87.
B. Lewin (1994) "Genes V" Oxford U Press.
Hullin R et al. (1992) *The Embo Journal* 11:3:885–90.
Perez–Reyes E et al (Jan 25, 1992) *J of Biol Chem* 267:3:1792–977.
Browne, D.L. et al. (1994) *Nat. Genet.* 8:136–140.
Diriong, S. et al. (1995) *Genomics.* 30:605–609.
Fletcher C.F. et al. (1996) *Cell* 87:607–617.
Hovatta I. et al. (1994) *Genomics* 23:707–709.
Joutel, A. et al. (1993) *Nature Genet.* 5:40–45.
Joutel, A. et al. (1994) *Am. J. Hum. Genet.* 55:1166–1172.
Joutel, A. et al. (1994) *Rev. Neurol.* 150:340–345.
Lara M. et al. (1995) *Rev. Neurol.* 23 supp 2:S179–184.
May, A. et al. (1995) *Hum. Genet.* 96:604–608.
Vahedi, K. et al. (1995) *Ann. Neurol.* 37:289–293.

* cited by examiner

*Primary Examiner*—Shin-Lin Chen
(74) *Attorney, Agent, or Firm*—Rae-Venter Law Group, P.C.

(57) ABSTRACT

Genes for familial hemeplegic migraine (FHM), episodic ataxia type-2 (EA-2), common forms of migraine, and other episodic neurological disorders, such as epilepsy, have been mapped to chromosome 19p13. A brain-specific P/Q type calcium channel subunit gene, covering 300 kb with 47 exons is provided. The exons and their surroundings reveal polymorphic variations and deleterious mutations that are linked to various types of cation channel dysfunctions causing episodic neurological disorders in man or animals.

15 Claims, 48 Drawing Sheets

Figure 2:
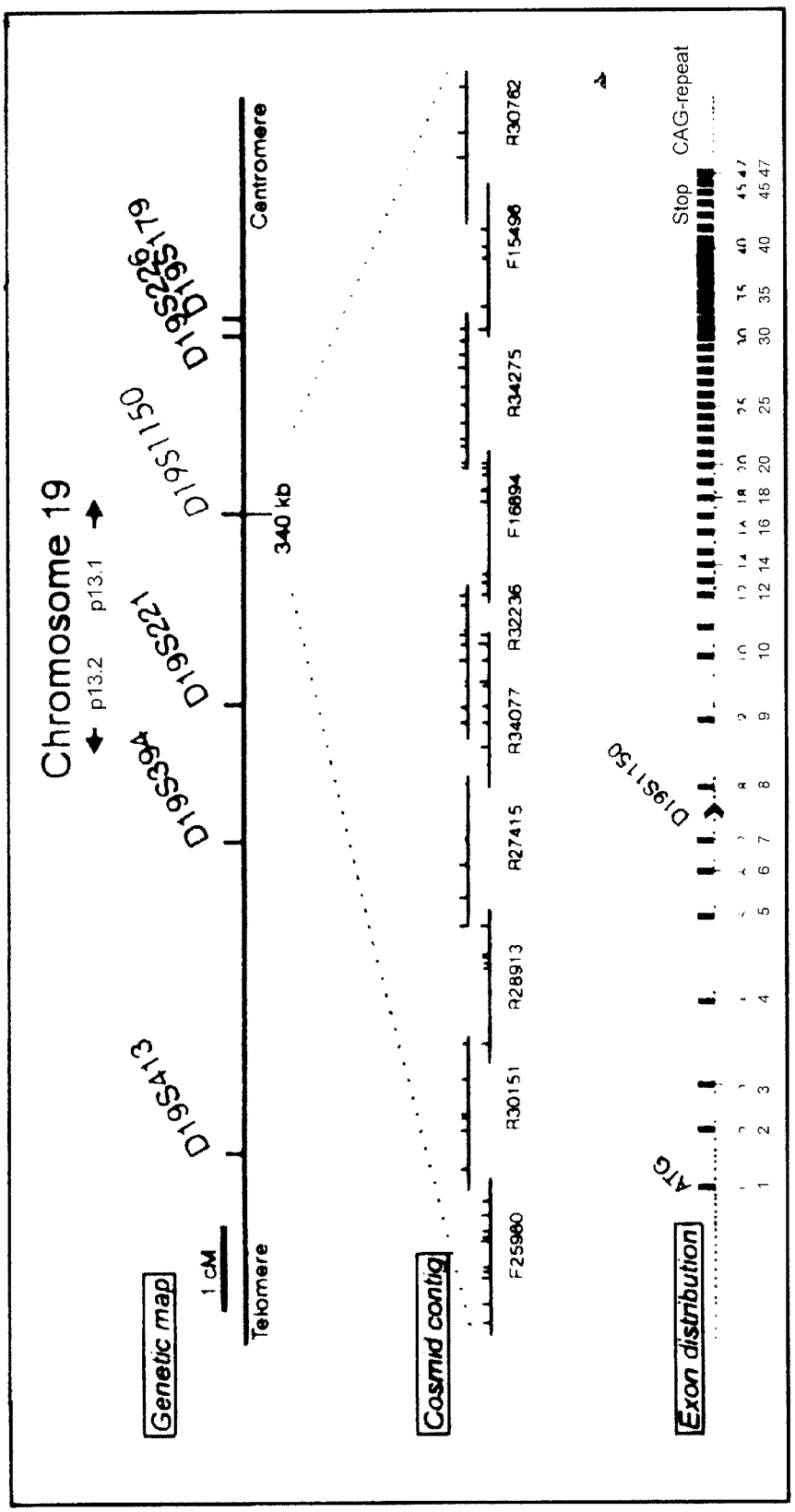

```
//
Submission no   :   1
exon 1          :   <..672
start codon     :   381..383
intron 1        :   673.
Remarks         :   no consensus splice site intron 1
```

| | | | | |
|---|---|---|---|---|
| tttttttacg | ttctcttttt | tttcgagtgg | tgactggatg | ctgattcttc | 50 |
| ctcgtatttt | tgctgcttct | ctctccctcc | cctccttccc | gggcccgggc | 100 |
| ccgccccgca | ccctccttcc | gcccctcctt | ctccggggtc | agccaggaag | 150 |
| atgtcccgag | ctgctatccc | cggctcggcc | cgggcagccg | ccttctgagc | 200 |
| ccccgacccg | agcgccgagc | cgccgcgcga | tgggctgggc | cgtggagcgt | 250 |
| ctccgcagtc | gtagctccag | ccgccgcgct | cccagccccg | gcagcctcag | 300 |
| catcagcggc | ggcggcggcg | gcggcggcgt | cttccgcatc | gttcgccgca | 350 |
| gcgtaaccgg | agccctttgc | tctttgcaga | ATGGCCCGCT | TCGGAGACGA | 400 |
| GATGCCGGCC | CGCTACGGGG | GAGGAGGCTC | CGGGGCAGCC | GCCGGGGTGG | 450 |
| TCGTGGGCAG | CGGAGGCGGG | CGAGGAGCCG | GGGGCAGCCG | GCAGGGCGGG | 500 |
| CAGCCCGGGG | CGCAAAGGAT | GTACAAGCAG | TCAATGGCGC | AGAGAGCGCG | 550 |
| GACCATGGCA | CTCTACAACC | CCATCCCCGT | CCGACAGAAC | TGCCTCACGG | 600 |
| TTAACCGGTC | TCTCTTCCTC | TTCAGCGAAG | ACAACGTGGT | GAGAAAATAC | 650 |
| GCCAAAAGAT | CACCGAATGG | CCatatcctt | ttgcccgaac | cccagcagca | 700 |
| gctgcgcctc | ccctcctcc | ctccgcctcc | cctcttccag | gctgggagag | 750 |
| agacccgggg | gttgatggga | ggtggggagg | agggggtct | tccaggggct | 800 |
| gggagagggg | gcaccgggag | gagtgtgaaa | gaatctctcc | accccgagct | 850 |
| gggttgagct | accctggagg | cttgggaatg | ggttttcgg | gggctggggg | 900 |
| ccggccagcc | ggagagtgga | tccttcccaa | ggaccgactc | tagaatgaga | 950 |
| tct | | | | | 953 |

Fig. 1

```
//
Submission no  :    2
Intron 1       :    <..88
Exon 2         :    89..194
Intron 2       :    195..>
Remarks        :    No consensus splice site intron 1 gatctttycc actggggtca gtgggggtgg gtgcacctcc aacacccttc      50
        ttttctttga acaagatttt tccttaattc cccaatacTC CCTTTGAATA     100
        TATGATTTTA GCCACCATCA TAGCGAATTG CATCGTCCTC GCACTGGAGC     150
        AGCATCTGCC TGATGATGAC AAGACCCCGA TGTCTGAACG GCTGgtgagt     200
        gatgtctttt ctcagggtct tctccttggc tttagcagga cattaatttt     250
        tgggggagtg gagcagggca cagaggaggc tctcagtcct ggagcccaga     300
        gccagatcat gggaagccta aatttccttt tcatttttc ttgaaccaga      350
        gtctcgctct gtcacccagg ctggagtgca gtggttcagt catagctcac     400
        tgcagcctcc acctcctggg ctcaagccat cctcccactg cagcctcctg     450
        agtagcaggg actaacaggt gccaccatgc ccagttaatt ttcttatttt     500
        tatcttttt tgtaagaaga tggggat                              527
```

Fig. 1A-1

```
//
Submission no  :  3
Intron 2       :  <..57
Exon 3         :  58..197
Intron 3       :  198..> gatcttgtca  acatctgccc  agcccaagac  gctgaccttg  ccttctctcc        50
     cttccagGAT  GACACAGAAC  CATACTTCAT  TGGAATTTTT  TGTTTCGAGG       100
     CTGGAATTAA  AATCATTGCC  CTTGGGTTTG  CCTTCCACAA  AGGCTCCTAC       150
     TTGAGGAATG  GCTGGAATGT  CATGGACTTT  GTGGTGGTGC  TAACGGGgta       200
     agtggcgcgt  gctatacgct  ttggatttaa  ctagctgaag  gattacgagg       250
     cttttggttg  gtgtggtccg  ggccaggctc  aggaaggctg  agcccttgtg       300
     ttctccctcc  ccttgttatg  cgcctgcctc  ctttctgcca  acaccccacc       350
     tccatgtctc  agctgtatat  tacagcagat  gctttctgtt  acaattaaaa       400
     taatagctca  ttattgttgg  ctgcttccag  agtgctttat  g                441
```

Fig. 1A-2

```
//
Submission no  :   4
Intron 3       :   <..142
Exon 4         :   143..234
Intron 5       :   235..> aaaactgagg ccagtggtgt cgagtcacct gcctgtggtc acccaaccaa      50
     tacaggacag cttggaatcc caagcacccc cgccctgctg tctgaccccc     100
     aaaacccacc ctctgttctc cattctggct tctttctttc agCATCTTGG     150
     CGACAGTTGG GACGGAGTTT GACCTACGGA CGCTGAGGGC AGTTCGAGTG     200
     CTGCGGCCGC TCAAGCTGGT GTCTGGAATC CCAAgtgcgt gagtttccga     250
     ccctgacaa                                                  259
```

Fig. 1A-3

```
//
Submission no   :   5
Intron 4        :   <..118
Exon 5          :   119..271
Intron 5        :   272..> cttaatattc  cctcaggaac  acacctgctt  tgtctgggag  agacctgggc        50
        gtcttggtgg  cggggttttg  ggggtacttg  ctcatgggct  tatggggcct       100
        ctctctgtgt  ccccccagGT  TTACAAGTCG  TCCTGAAGTC  GATCATGAAG       150
        GCGATGATCC  CTTTGCTGCA  GATCGGCCTC  CTCCTATTTT  TTGCAATCCT       200
        TATTTTTGCA  ATCATAGGGT  TAGAATTTTA  TATGGGAAAA  TTTCATACCA       250
        CCTGCTTTGA  AGAGGGGACA  Ggtaggtcca  cggagcatga  tgcatctttc       300
        cagttttctc  cttcagggac  aagctcttgg  gaggattagg  cagggglglg       350
        cttctttctc  ctggcagctg  ggaggaccgt  ctccttcaga  gagcactac        399
```

Fig. 1A-4

```
//
Submission no  :  6
Intron 5       :  <..22
Exon 6         :  23..216
Intron 6       :  217..> tttttcccct tcccttttgt agATGACATT CAGGGTGAGT CTCCGGCTCC      50
         ATGTGGGACA GAAGAGCCCG CCCGCACCTG CCCCAATGGG ACCAAATGTC     100
         AGCCCTACTG GGAAGGGCCC AACAACGGGA TCACTCAGTT CGACAACATC     150
         CTGTTTGCAG TGCTGACTGT TTTCCAGTGC ATAACCATGG AAGGGTGGAC     200
         TGATCTCCTC TACAATgtaa gtgatgctgg gacagtgtgt gtggacaatc     250
         agagtctcag ggaggtggcc tcctgggacc agtgagactc caacgctgca     300
         atggagggac cctgagctgg gaaaggcagc ccaaggacaa cacagcccca     350
         ctgaagctgg cctgaggctc aggcttttga agattacagg ggctcatgag     400
         cagaactcta actataggge atagaagtct ggagggcccc cagatgcaac     450
         atcatttttc attgtgcaag tgtttagata taatttaga ttttgaata        500
         cggaaaggtt atgtgatcca aaatccaaca cagataaaag atagagtaat     550
         atctttggac gtaggcgagg ggtccctgcc ctgagg                    586
```

Fig. 1A-5

```
//
Submission no   :   7
Intron 6        :   <..183
Exon 7          :   184..287
Intron 7        :   288..> tttcttcaga aaacggttcc ttcctccatt tcccctctg ggatgccaga         50
        gccccagaac tccacaagcc aagaacattt aagacagagc cacaagagaa        100
        ccgagcttcc ccttccctca cctgtcaggt tctatctgag tcccagtcaa        150
        ctctcacctg ctttccctcc tcacaccta cagAGCAACG ATGCCTCAGG         200
        GAACACTTGG AACTGGTTGT ACTTCATCCC CCTCATCATC ATCGGCTCCT        250
        TTTTTATGCT GAACCTTGTG CTGGGTGTGC TGTCAGGgta agtttctgct        300
        actccccacc ccatcccact cactcctctt tgctaacttc tttccaagta        350
        gaggccattg aagctttgtt ttcattcact agacaga                      387
```

Fig. 1A-6

```
//
Submission no  :  8
Intron 7       :  <..190
Exon 8         :  191..306
Intron 8       :  307..>
Sequence       :  412
Remark         :  intron 7 contains CA-repeat (D19S1150)
```

```
cccagtcttt tcccagaagt cctgactcct cctgttgaaa actcctgacc     50
tccagggact tctgaatccc caaacacaca cacacacaaa cacacacaca    100
cacacacaca cacacacaca caaacacaca cacaaacgtt tcctaacatt    150
ttaaaaacag ccatactctg gcttttctat gcttctccag GGAGTTTGCC    200
AAAGAAAGGG AACGGGTGGA GAACCGGCGG GCTTTTCTGA AGCTGAGGCG    250
GCAACAACAG ATTGAACGTG AGCTCAATGG GTACATGGAA TGGATCTCAA    300
AAGCAGgtga ggcccttcca tctggggcc cagggatgga gatcccaggc     350
cacagagtac aaagagagtc atgcagtttg gagaaggcta agctgggagg    400
gttatgatgg ga                                             412
```

Fig. 1A-7

```
//
Submission no  :  9
Intron 8       :  <..513
Exon 9         :  514..570
Intron 9       :  571..> gagtaggaag ttagaggcag ggtggtcagg gaaggcttct ctaaggaagt          50
accctctgag cagagagacc tgaaggacgt gaagaaggaa gctgtgggga         100
tgtcaaggga aggggcattc caggcagaga cagcaagtgc aaaggccctg         150
agctaggaac gtatttgaga cacagcaagg aagccagtgc agctgaaaca         200
gagtgagagg tggggacagc tggaggagag gaagacagga aggtgatgga         250
gatcagatca agcaggggct tataggctgt ggtgtggaca ttggttttta         300
ttttgcgcga ggtggggaga atgttggcta ttgctactgt tgcggaggtg         350
gggcttgaag tcacaaacca cccagcagca tgttttttgg tcggttgagc         400
tgtcaccatc agtcagcaga gaatgggggt ggccgggcag acccttcttc         450
ctggtccaag ggagaactca tcctccaaat gcaggagctt aactctgtgc         500
tcttcctctt cagAAGAGGT GATCCTCGCC GAGGATGAAA CTGACGGGGA         550
GCAGAGGCAT CCCTTTGATG gtaactgctc taaacccacc tcagggtgg          600
gtcccagggg a                                                   611
```

Fig. 1A-8

```
//
Submission no    :   10
Intron 9         :   <..86
Exon 10          :   87..179
Intron 10        :   179..> ttaatccaag acacactgtg tgtcctatat ggtctgtgtt cgaaaaaggg      50
        taacgtcttt ttctcttgcc atgtttccat tgttagGAGC TCTGCGGAGA     100
        ACCACCATAA AGAAAAGCAA GACAGATTTG CTCAACCCCG AAGAGGCTGA     150
        GGATCAGCTG GCTGATATAG CCTCTGTGGg tgagtccctt cctctgccac     200
        ctatcagttg ttcatcacct atcgcccaag agacatggtg gggtgggggc     250
        agagggcttg caaaccgtgc tgcctggatt tgggtctcag ctccaccctt     300
        tcccacctgt gcgtgtgtcc tgggcagatt acatcattat gggaataaca     350
        tccgtgccta gcttctcatt attttgtggg aattcaacta aatgatcccc     400
        atgaagcatg gcaaaccagc acctggcagg gacgaagctc ccagtcaagt     450
        tggtgaatgt ttgtgactca ttcgggaagt atcatggggg acctgcttat     500
        attaggtgct tggttgcaaa caaacaaggc agtcacgagg ctgagctggg     550
        aggatcactt cagcctggga agtggaggct gcaataagcc attattgtgt     600
        tactgcactc cagcctggca cagaaaaaaa aaaaaaanac aaactgagcc     650
        agcaca                                                    656
```

Fig. 1A-9

```
//
Submission no  :  11
Intron 10      :  <..450
Exon 11        :  451..660
Intron 11      :  661..>
```

```
gatcacttct aaagttaaat gtccatggga aaacagtctc atccacatct        50
ctttctggag gccttccaag cgtgctccat gcagctctgt tgcctgcccc       100
tgcatcaggg aatggaggct ctgctttatc ctgccctgtg gtgtgactcc       150
cagaggcatc agatgtggct gggagtggga gacatggaaa attggctcct       200
gcaacagaga actatcagcc ttcccatcaa ttggttactt ctaattctgt       250
tattttcag  gggcactgtc ttctcataag ctccatctat gcaaaactaa       300
gcccatgggt catgatggtt ccctcaggcc agaggcttgc tggagagact       350
aatggatccc ctggctaaaa tctgtgcttg ggctgcacat tggttaattt       400
cttctgaagg aacagcctga gcctgacatt ctccatcttt tccctggcag       450
GTTCTCCCTT CGCCCGAGCC AGCATTAAAA GTGCCAAGCT GGAGAACTCG       500
ACCTTTTTTC ACAAAAAGGA GAGGAGGATG CGTTTCTACA TCCGCCGCAT       550
GGTCAAAACT CAGGCCTTCT ACTGGACTGT ACTCAGTTTG GTAGCTCTCA       600
ACACGCTGTG TGTTGCTATT GTTCACTACA ACCAGCCCGA GTGGCTCTCC       650
GACTTCCTTT gtgagtatca cccagcccca ccctgccaa  ctccctgatc       700
cctccctcac acccttttc  cacttctctt tctctggtag tatgtgtatc       750
ttctttggtc ctcattgaat ctgcccct                              778
```

Fig. 1A-10

```
//
Submission no   :   12
Intron 11       :   <..323
Exon 12         :   324..436
Intron 12       :   437..> gatcacttgt ggccaggagt tcaagancag ccagggcaac atagtgagga        50
       cccccatctc cacattaaaa attttaaaaa gaaaaaagat aagtcagaag       100
       ttgggtgtgg tgacacatgc ctgtagttct agcatgttgg aggccaaatc       150
       agggaaactg tttgaggcca ggagtttgaa accagcctaa cagcatagca       200
       agacctcatc tctacaaaaa ataaaaagtt taaaaatgat aataaaagga       250
       aagtcagagc cacctggaac ccctaccctc agcaagccta acctcctctc       300
       tgtttcctcc ttctcccttc tagACTATGC AGAATTCATT TTCTTAGGAC       350
       TCTTTATGTC CGAAATGTTT ATAAAAATGT ACGGGCTTGG GACGCGGCCT       400
       TACTTCCACT CTTCCTTCAA CTGCTTTGAC TGTGGGgtaa gtgctcttgt       450
       ttctaagagt tcatttctcc agctcttgcc tggaatgaca gatacctgga       500
       cacattaaag ggagaaaggt aaagtcaccc ctgaatatga gagactcaga       550
       tggatgcaga aggaatgaga aaacaatcca aacactggca aggatacagt       600
       gtacccagaa ccctcaacca ccgcca                                626
```

Fig. 1A-11

```
//
Submission no  :  13
Intron 12      :  <..545
Exon 13        :  546..658
Intron 13      :  659..821
Exon 14        :  822..953
Intron 14      :  954..>
```

```
gatcngncat gcacaccagc ctgggtgata agagcaagac tcctctcaaa       50
ataaatgaat aaataaaaat aaataaataa ataagaggcc gggtgcagtg      100
gctcaatgct ttggaaagtg gaggccaaca gttggagaga ccaaagcagg      150
aggatggctt cagcccagaa gtttgaggcc mgcctgggca atactagcga      200
gacactatct ctataaaaat gttttaaaat tagccagatg tggtggggca      250
cacctgtaat cccagctact caagaggctg aggtgggagg atcacttaag      300
cccaggagga cagtgctgca gtgagctatg attgcgccca ctgcactcca      350
gcctgggtga cacagtgaga cccggtctct atagataaat gaatggatga      400
atgaggggt caaggatcct cacccggctt ccatttggag ggaggagttt       450
ggttgagttc ttgcaaggtt ggtacctagg aaatgcttgc cagttctgga      500
gcccagacac tgtccctgga catgagacca ggttctctgc cctagGTTAT      550
CATTGGGAGC ATCTTCGAGG TCATCTGGGC TGTCATAAAA CCTGGCACAT      600
CCTTTGGAAT CAGCGTGTTA CGAGCCCTCA GGTTATTGCG TATTTTCAAA      650
GTCACAAAgt aagtctttgg ggttcctgga catttgtaca ggggtgggg      700
atgggggaca tggtggggcc gcctccagaa agttgggaaa gtgagcctcg      750
tgtttcgagg gctgactccg gggcctgcct wccccgcctg gcctgagtcc      800
tcgcctggsc tctgtcggca gGTACTGGGC ATCTCTCAGA AACCTGGTCG      850
TCTCTCTCCT CAACTCCATG AAGTCCATCA TCAGCCTGTT GTTTCTCCTT      900
TTCCTGTTCA TTGTCGTCTT CGCCCTTTTG GGAATGCAAC TCTTCGGCGG      950
CCAgtaagtc cttcacagga attcaa                                976
```

Fig. 1A-12

```
//
Submission no  :  14
Intron 14      :  <..201
Exon 15        :  202..274
Intron 15      :  274..>
```

```
ccctccacgt gcaggctgcc ttcctcgtag cccagacacc catttgcggt         50
cacccaaatg ggcagggccc tgggtaccac tcagggtttc ctggggacag        100
agatgatgga aacgttcgtt tccttggaga tgagatactg agccacaccc        150
tcagagcacc ccgggtgggg ccaacgtgaa atgtctgtgt cctccctgca        200
gGTTTAATTT CGATGAAGGG ACTCCTCCCA CCAACTTCGA TACTTTTCCA        250
GCAGCAATAA TGACGGTGTT TCAGgtacag cctccacctg gccccacggg        300
ccaacacctc tcagtgtcac agatgaaagt gcctgctcca catccaaggg        350
gcttccctga actcctcctt ctctacctgg ccttttcaca ccactttgaa        400
acacagattt tatggttatc attattcaat tatggtgagg ccaacagatc        450
aggagatgaa tgtcattgga aagatagttt gtggctgggc acggtggctc        500
acacccataa tcccagcact ttggccaggt acggtggctc acacctgtaa        550
tcccaacgct ttgggaagcc caggtgggcgg atcacttga gatcaggaat        600
tcgagaccag cctggccaan atggtgaaac cccatctcta ctaaaaatac        650
aaaaattagc cgggcgtggt agcacatgcc tgtaatccca gctactcggg        700
agatgaggca caagaattgc ttgaacctgg gaggcagagg ttgcagtgag        750
ccaagatcgc gccactgcac tcmagcctgg gcaacagagt gagactccat        800
ctcaaaaaag caaaagaaaa aaaaaaccac tttgggaggt caagatggga        850
ggactacttg aggccaggag tttgagcaa gtctgggcaa catagtgaga        900
ctccgtctct gcaaaaaaat wataataata attagctggg catggtgata        950
catacctcct agctactagg gcagctgaag tggaaggatt gcttaagccc       1000
aggaggttga ggctgcagta agctacaatc acaccactat actccagcct       1050
gggcgagaga gcaaagccct gtctcaaaaa cgaaaagaaa gtttgttata       1100
ctcacagatc                                                   1110
```

Fig. 1A-13

```
//
Submission no  :  15
Intron 15      :  <..524
Exon 16        :  525..642
Intron 16      :  643..795
Exon 17        :  796..863
Intron 17      :  864.>
```

```
         gatcctccca ccttggcctc ccaaagtgct gggattacag gcatgagcca    50
         tggcatgcgg tctcttcctg ttcttataag ggcactaata ccatcatgaa   100
         gtcccccatg acctcatcta accctagtta cctcttaaag gccccatctc   150
         caaataccat cccatcatag gttagggctt caactcatga atttggaggc   200
         gggcacaatt tagtccataa caaatcccct taatcacatc aagtaagaca   250
         gagttacagg agggtctgtg actcctccag ggtcccattt tcctagaagc   300
         caggctaaga gccccacgac gcaggaacgg ccctttctac tcgcaaacaa   350
         agagaaaagc caaggagaag ccaacacgga gtctggctct gcaaaccggg   400
         caggattgtt aaagacctcc tgggctcggg gatggggtgg gcggattccg   450
         gctccacagc tgcatctcca aggggcccgt ggctgagagg ggggttggct   500
         gtgtgtttct tcctcccctt tcagATCCTG ACGGGCGAAG ACTGGAACGA   550
         GGTCATGTAC GACGGGATCA AGTCTCAGGG GGGCGTGCAG GGCGGCATGG   600
         TGTTCTCCAT CTATTTCATT GTACTGACGC TCTTTGGGAA CTgtatcctt   650
         catggagaga gagaagggga caggcctgga cctctggcag aggagaggtt   700
         gcaggggctc aagggagggt actgagagac ccagatacccc agggcccaag   750
         tggtgtccca ccagtggttg cttttcctga ctcagacatt tgcagACACC   800
         CTCCTGAATG TGTTCTTGGC CATCGCTGTG GACAATCTGG CCAACGCCCA   850
         GGAGCTCACC AAGgtggagg cggtgggaga atgtttctct ggcaaagtta   900
         ccacctgccc atggcagatc aagcactttt ttggattaac tgagccacag   950
         gaaataacat tttcaaatag atkaaaaaga tc                       982
```

Fig. 1A-14

//
```
Submission no  :    16
Intron 17      :    <..119
Exon 18        :    120..226
Intron 18      :    227..>
```

```
ccttggttct  gattggtcga  aatatttcaa  atgttgcccc  tggtcagcaa       50
cagggtcaga  agtgagtccc  caaggcctag  ttcatgtttt  gtgaacaaag      100
attccacgtg  cctttcagG   ACGAGCAAGA  GGAAGAAGAA  GCAGCGAACC      150
AGAAACTTGC  CCTACAGAAA  GCCAAGGAGG  TGGCAGAAGT  GAGTCCTCTG      200
TCCGCGGCCA  ACATGTCTAT  AGCTGTgtaa  gtccctaat   ccctgggatg      250
cta cctggc  tcctgaacgt  gtccgaccac  tatccaggca  cagatttggg      300
aagcagtggg  ggtg                                                314
```

Fig. 1A-15

```
//
Submission no  :  17
Intron 18      :  <..209
Exon 19        :  210..1019
Intron 19      :  1020..>
```

```
gccccuagcc aggtgggagc catggagggt tcttgagcag aggaggctgg      50
gacctgactc agatgctcac agactcctag cattcaggtg gggagtagag     100
ggtggagagc aggagtggga ggctgagatg tgggttggtt cgcctgggtc     150
atccatccaa gctacagtgc ctagcaatgc tctaagctcc tgtgaccatg     200
ccactgcagG AAAGAGCAAC AGAAGAATCA AAAGCCAGCC AAGTCCGTGT     250
GGGAGCAGCG GACCAGTGAG ATGCGAAAGC AGAACTTGCT GGCCAGCCGG     300
GAGGCCCTGT ATAACGAAAT GGACCCGGAC GAGCGCTGGA AGGCTGCCTA     350
CACGCGGCAC CTGCGGCCAG ACATGAAGAC GCACTTGGAC CGGCCGCTGG     400
TGGTGGACCC GCAGGAGAAC CGCAACAACA ACACCAACAA GAGCCGGGCG     450
GCCGAGCCCA CCGTGGACCA GCGCCTCGGC CAGCAGCGCG CCGAGGACTT     500
CCTCAGGAAA CAGGCCCGCT ACCACGATCG GGCCCGGGAC CCCAGCGGCT     550
CGGCGGGCCT GGACGCACGG AGGCCCTGGG CGGGAAGCCA GGAGGCCGAG     600
CTGAGCCGGG AGGACCCCTA CGGCCGCGAG TCGGACCACC ACGCCCGGGA     650
GGGCAGCCTG GAGCAACCCG GGTTCTGGGA GGGCGAGGCC GAGCGAGGCA     700
AGGCCGGGGA CCCCACCGG AGGCACGTGC ACCGGCAGGG GGGCAGCAGG     750
GAGAGCCGCA GCGGGTCCCC GCGCACGGGC GCGGACGGGG AGCATCGACG     800
TCATCGCGCG CACCGCAGGC CCGGGGAGGA GGGTCCGGAG GACAAGGCGG     850
AGCGGAGGGC GCGGCACCGC GAGGGCAGCC GGCCGGCCCG GGCGGCGAG     900
GGCGAGGGCG AGGGTCCCGA CGGGGGCGAG CGCAGGAGAA GGCACCGGCA     950
TGGCGCTCCA GCCACGTACG AGGGGGACGC GCGGAGGGAG GACAAGGAGC    1000
GGAGGCATCG GAGGAGGAAg taagtggagg tgacctcgaa tccgcagaat    1050
gacggtaaca ttaataatac aacagccaaa gtagcacgtg ctgtgtattt    1100
gttataaaat ata                                            1113
```

Fig. 1A-16

```
//
Submission no  :  18
Intron 19      :  <..67
Exon 20        :  68..531
Intron 20      :  532..> gtcctgaaac tttgccttttt aatcctaaat cattgttggt tctttttcat         50
       tcacttgcct tcctcagAGA GAACCAGGGC TCCGGGGTCC CTGTGTCGGG        100
       CCCCAACCTG TCAACCACCC GGCCAATCCA GCAGGACCTG GGCCGCCAAG        150
       ACCCACCCCT GGCAGAGGAT ATTGACAACA TGAAGAACAA CAAGCTGGCC        200
       ACCGCGGAGT CGGCCGCTCC CCACGGCAGC CTTGGCCACG CCGGCCTGCC        250
       CCAGAGCCCA GCCAAGATGG GAAACAGCAC CGACCCCGGC CCCATGCTGG        300
       CCATCCCTGC CATGGCCACC AACCCCAGA ACGCCGCCAG CCGCCGGACG         350
       CCCAACAACC CGGGGAACCC ATCCAATCCC GGCCCCCCA AGACCCCCGA         400
       GAATAGCCTT ATCGTCACCA ACCCCAGCGG CACCCAGACC AATTCAGCTA        450
       AGACTGCCAG GAAACCCGAC CACACCACAG TGGACATCCC CCCAGCCTGC        500
       CCACCCCCCC TCAACCACAC CGTCGTACAA Ggtgagaccc tctgctctca        550
       catcactggg cagggacct ggcgtcctgg agccagaggt                    590
```

Fig. 1A-17

```
//
Submission no  :  19
Intron 20      :  <..75
Exon 21        :  76..217
Intron 21      :  218..>
```

```
ggagtacacc gaggagttcc cagagacttg tgggaaattg tggagggagc        50
cctgtgttgg ttcttgtccc aacagTGAAC AAAAACGCCA ACCCAGACCC       100
ACTGCCAAAA AAAGAGGAAG AGAAGAAGGA GGAGGAGGAA GAAGACGACC       150
GTGGGGAAGA CGGCCCTAAG CCAATGCCTC CCTATAGCTC CATGTTCATC       200
CTGTCCACGA CCAACCCgtg agtatggccc ccgagcagag ggcaggggggg      250
gctgggtctc ccaccagggt ggcggaannn nnnnnnnnnn nnnnnnnctc       300
ccaccagggt ggcggaagtc aggccagatt agagggcaat                  340
```

Fig. 1A-18

```
//
Submission no  :   20
Intron 21      :   <..97
Exon 22        :   98..227
Intron 22      :   228..>
```

```
gatctcagta gtggtaggta acatgagatt atggaagaaa agggtttgtg      50
agcctgtggt ctgagtggac ctctgcacgc ccatctgtct ccaacagCCT     100
TCGCCGCCTG TGCCATTACA TCCTGAACCT GCGCTACTTT GAGATGTGCA     150
TCCTCATGGT CATTGCCATG AGCAGCATCG CCCTGGCCGC CGAGGACCCT     200
GTGCAGCCCA ACGCACCTCG GAACAACgtg agtcccacag agcacacccc     250
ttcctagcct ggctgctctg cctcaggcca ctttctcctg catccaaaat     300
gctcataggt agggtgggat gttggggtca cccctaggca tagcccttat     350
ggctgctggt tgagagggga agctctgatt ccttggggat gctcttggga     400
gcaagacatt ccttgaggca gtttctctgt gagcctggtg gggtggaggt     450
ggcccagagt gactggggct gaaaatt                              477
```

Fig. 1A-19

```
//
Submission no  :  21
Intron 22      :  <..33
Exon 23        :  34..93
Intron 23      :  94..> gatccactgc tctcttgctt ttatccctta cagGTGCTGC GATACTTTGA        50
        CTACGTTTTT ACAGGCGTCT TTACCTTTGA GATGGTGATC AAGgtgagtg       100
        cagattataa gtgagaacac acggtaattt ttttttttaa gcaagtgcag       150
        ggctgggcac agtggatc                                          168
```

Fig. 1A-20

```
//
Submission no  :  22
Intron 23      :  <..232
Exon 24        :  233..339
Intron 24      :  340..> gatctaagag ccggcaagcc agagctggct tccatcaggc aaaggggggc       50
     cgcctcatgg ggcaggggct ccccactcct ccctgggagt cctctggcca      100
     ctgcccatcc ctgcaagatg aggtggcctc attggcttcc ctgcctctcc      150
     ccgagaggct agagagtggg tggcagcacc ccagggtggg gatcaggtgg      200
     gggttctgag caccctctct tctccccac agATGATTGA CCTGGGGCTC      250
     GTCCTGCATC AGGGTGCCTA CTTCCGTGAC CTCTGGAATA TTCTCGACTT      300
     CATAGTGGTC AGTGGGGCCC TGGTAGCCTT TGCCTTCACg taagtctctt      350
     cgcaagggtt tcctcttg                                         368
```

Fig. 1A-21

//
Submission no  :  23
Intron 24      :  <..244
Exon 25        :  245..344
Intron 25      :  345..>

```
gatcttaacc ccaagacact tcatctaaag gaaaaactgc cataatacac         50
agattatttt aggtcagctc actttactgc catctgctgg gaagttgtaa        100
taatacaaat atccatacac gatggctagg atgttatcag caccctcctt        150
aatgtgttgt ccttgagcag tgtacaacct gctcagctgt acatgataac        200
cctgacagtc cccccaccg cacccacca tctcccaatc tcacCTTGAG         250
CTTTGGCAGC CGCTTGATGG TTTTAAGAGG TCGTAGCACC CGGAGGACTC        300
GGAGGGATTT AATCGTGTTG ATGTCTTTTC CTTTGCTATT GCCActgtgg        350
aggaatgttt aggtgggaag aagggaagag aggaagcaga ggtcaggttg        400
ggtaggggc agcccacagc tccatgggac cctacccttc ccaggcctag         450
aagtctgggg tgagcttggc acaagcctgc cctttcctgg tgaagagtgg        500
tccattttac cctgt                                              515
```

Fig. 1A-22

```
//
Submission no  :  24
Intron 25      :  <..67
Exon 26        :  68..228
Intron 26      :  229..>
```

```
ggccactgga ggcagaaggt tggcaggtcc ccagcccctc atgctctctg       50
tcaactccac cccacagGCT GTGTTTGACT GTGTGGTGAA CTCACTTAAA      100
AACGTCTTCA ACATCCTCAT CGTCTACATG CTATTCATGT TCATCTTCGC      150
CGTGGTGGCT GTGCAGCTCT TCAAGGGGAA ATTCTTCCAC TGCACTGACG      200
AGTCCAAAGA GTTTGAGAAA GATTGTCGgt gggtctccgc tttccagcac      250
attcccattg gaaccagcag gtgggcaggg gggaagtggc tagaggcatt      300
ggccacttgg gctcagagac tggagaagtg atgagccttg gaagtgactc      350
agttgcaacc agcttggatc aagggtagaa agaaaaccgg ttttagaatt      400
tgagtc                                                      406
```

Fig. 1A-23

```
//
Submission no  :   25
Intron 27      :   <..177
Exon 27        :   178..315
Intron 26      :   316..>
Remark         :   reversed direction!

gatctcaaac tcctggcctc aagtgataca tctgccttgg cctcctaaag        50
        tgttgggatt acaggcgtga gcaccatgcc cggcctccaa gacctttctt       100
        attgctaagc tctcaggccc tttatcctcc tgctccccag ggctcctcct       150
        ggatagattt ccagtcgggc cacttacTGT GGCCAGCCTT CTCCCGTGGA       200
        CACGGTGAAG AGGGTCAGCA GAGCCCACAG CACATTGTCG TAATGGAATT       250
        CATACTTCTT CCACTCCCGG TCTCGCGCCT TCACCTCATT CTTCTCGTAG       300
        AGGAGGTATT TGCCTctgcc acagagagtg gggactgtta gtaaatggga       350
        aagagggget gtcttgcact tgtctttggt tatcagagac agggggaggg       400
        aaaggaagag tggtccacca ncctagactg cttgggaagc agtgacttcc       450
        catcctgcca ccatgtgttc ctgtgcttca taggggatgn cgtgtgcaat       500
        ctacttttna ggataa                                            516
```

Fig. 1A-24

```
//
Submission no    :    26
Intron 27        :    <..84
Exon 28          :    85..276
Intron 28        :    277..> accttcctca  tcacccttgg  gtccctgtct  ctctccttcc  tgccccttcc      50
        ctctccctgc  cccattcctt  gcagGGTCCT  CAAGCATTCG  GTGGACGCCA     100
        CCTTTGAGAA  CCAGGGCCCC  AGCCCCGGGT  ACCGCATGGA  GATGTCCATT     150
        TTCTACGTCG  TCTACTTTGT  GGTGTTCCCC  TTCTTCTTTG  TCAATATCTT     200
        TGTGGCCTTG  ATCATCATCA  CCTTCCAGGA  GCAAGGGGAC  AAGATGATGG     250
        AGGAATACAG  CCTGGAGAAA  AATGAGgtgc  acttccaat   tccatctgtc     300
        ctttaaaaac  tggggacaca  cacaaacttt  aaaacacaca  caacacccag     350
        gaaccccttt  ctaggggtac  ctggggagg   gaacagaagc  attgtcccaa     400
        ccgaatccag  tcttcagggc  agcccttcat  ggagtttcag  aggaaacaca     450
        tcatatagtg  tatgtatcag  tcagtttaga  ctaggttat                  489
```

Fig. 1A-25

```
//
Submission no   :   27
Intron 28       :   <..253
Exon 29         :   254..418
Intron 29       :   419..>
```

```
tagcccatgc aanaatgggg aaatgncagt gcaagttttg gcagttgntg        50
acatctcaag caactgtanc tgttgggata agaaagcaat ggtgagaagg       100
aanagaganc ccaggaatcc tggctggggg caananaggc agagactcaa       150
gcagaagcac ttgagaaccg cgacgagtta gacagagggt gcccggtgta       200
cagccacctt cctcctgcct ctgccgctct caccactggc ctctctcccg       250  50
cagAGGGCCT GCATTGATTT CGCCATCAGT GCCAAGCCGC TGACCCGACA       300
CATGCCGCAG AACAAGCAGA GCTTCCAGTA CCGCATGTGG CAGTTCGTGG       350
TGTCTCCGCC TTTCGAGTAC ACGATCATGG CCATGATCGC CCTCAACACC       400
ATCGTGCTTA TGATGAAGgt aagtgcccca caccagcccc cagcactant       450
taacccccac ctcgttcctg cctctaccct gataaaatga aaccatttgc       500
agatttccca ga                                                512
```

Fig. 1A-26

```
//
Submission no  :  28
Intron 29      :  156
Exon 30        :  157..267
Intron 30      :  268..> gggtctttcc tgaactgtgc ctcctaccag tgaggttgct cagaccttgc         50
   ctggggctgg agtgttgcct ggagaacagc catgaagctg acctccccac        100
   ttcccacttc ccacccctgc tcgctgaccc ctgctactcc tgcttctttc        150
   ccctagTTCT ATGGGGCTTC TGTGGCTTAT GAAAATGCCC TGCGGGTGTT        200
   CAACATCGCC TTCACCTCCC TCTTCTCTCT GGAATGTGTG CTGAAAGCCA        250
   TGGCTTTTGG GATTCTGgta agtaccacct tggggctaca gctatgggct        300
   tggaanaanc caaggggga acaatgggtc ctggatgatg gtctcccaac         350
   gtggccccaa gaacccaac ctcaagggtg gcttcagtat cctgcccagt         400
   ggccacagat c                                                  411
```

Fig. 1A-27

```
//
Submission no  :  29
Intron 30      :  <..115
Exon 31        :  116..199
Intron 31      :  200..> ctgtcccggg cactccgctg atgggcaact gtgcctctaa catgcaccgg      50
          ccagcctagg gggccgggaa ccaagccctc tgttggcatc tctgtcttgt     100
          gggtccccat tctagAATTA TTTCCGCGAT GCCTGGAACA TCTTCGACTT     150
          TGTGACTGTT CTGGGCAGCA TCACCGATAT CCTCGTGACT GAGTTTGGGg     200
          taagtctccc tccagcttct ctctgggtga ctctgggctg gacgaggcag     250
          gcggcagggg gcgggggagc ggtcccagag gcagtgtgtc ccggaagcca     300
          tagctgcttg agccagcact tggccatgac cagagaggga gaactggggc     350
          cccggggaca agggcagccc ctcaggaggg cattgtgggg agatgggggt     400
          aacaaagctt ggctgtaggg                                      420
```

Fig. 1A-28

//
Submission no : 30
Intron 31 : <..148
Exon 32 : 149..265
Intron 32 : 266..>

```
ttaatagtgc tttctctctc cctccttatt tggggtctgg cttgcttttt       50
tcctgttggt tggcttcatg tagggcctc tgtgagtggt gacagctctg       100
agcctttggg gtgggtggat ggtcacccct cttcctccat ctccccagAA      150
TAACTTCATC AACCTGAGCT TTCTCCGCCT CTTCCGAGCT GCCCGGCTCA      200
TCAAACTTCT CCGTCAGGGT TACACCATCC GCATTCTTCT CTGGACCTTT      250
GTGCAGTCCT TCAAGgtgag tcctcgtccc tgctgctggc ccagggctg       300
agaagacagg tgaccctcat gctctggctg aatgtagaag tc              342
```

Fig. 1A-29

```
//
Submission no    :    31
Intron 32        :    <..156
Exon 33          :    157..222
Intron 33        :    223..394
Exon 34          :    395..509
Intron 34        :    510..>
```

```
          cccccaagaa gaatgcccac caagccctgg aaggactctg gcacgtggca      50
          tatggccacc caacccagtg gggcagagca ctgggacaag ggaggaagac     100
          tgcagtgcgg ctgagggacc cccagcactc ttcttcattg ccttttttcc     150
          caccagGCCC TGCCTTATGT CTGTCTGCTG ATCGCCATGC TCTTCTTCAT     200
          CTATGCCATC ATTGGGATGC AGgtgagtgt cgtgtcccta aggttcccag     250
          agcctcccaa ggagggcagc cacccttaga aagggtggg tcagaggagc      300
          ctggttcaca gaagcagcca tggaggttga gctgggtttc ccagaagcca     350
          ctggaggaat ggcagcccct ggtcgtcacc cwmcaattcc acagGTGTTT     400
          GGTAACATTG GCATCGACGT GGAGGACGAG GACAGTGATG AAGATGAGTT     450
          CCAAATCACT GAGCACAATA ACTTCCGGAC CTTCTTCCAG GCCCTCATGC     500
          TCTCTTCCGg tcagaagggg acctgctctg ataatnctgt ttccgtgggg     550
          tggggtgcc                                                  559
```

Fig. 1A-30

```
//
Submission no  :  32
Intron 34      :  <..94
Exon 35        :  95..245
Intron 35      :  246..>
Sequence       :  316 tcagagccat gctcactgtg tgctccactc ctgaggaggc gttggtacca    50
      gtcagggctg ggtgtccgag tctctgattt ctccctgtcc tcagGAGTGC   100
      CACCGGGGAA GCTTGGCACA ACATCATGCT TTCCTGCCTC AGCGGGAAAC   150
      CGTGTGATAA GAACTCTGGC ATCCTGACTC GAGAGTGTGG CAATGAATTT   200
      GCTTATTTTT ACTTTGTTTC CTTCATCTTC CTCTGCTCGT TTCTGgtgag   250
      tctgtggaca ctgtgagggc cgtctgggct ccctaagcct ggcttccttt   300
      cagggagtgg ttctgt                                        316
```

Fig. 1A-31

```
//
Submission no  :  33
Intron 35      :  <..211
Exon 36        :  212..339
Intron 36      :  340..> gtgtagtgag aactcacctc tccattcccc agtctctttc tgtctctgtc      50
tcatttcctt tccccatctt ctctctatcc ctctctccat ctggggcctc     100
tgtgtctgtc tttgggtctg tctgtccgtc tgactgtctg tatccttctc     150
acttcactca ttcattccct cggtctctgc cccattctct cttggtcccg     200
ggtccccaca gATGCTGAAT CTCTTTGTCG CCGTCATCAT GGACAACTTT     250
GAGTACCTCA CCCGAGACTC CTCCATCCTG GGCCCCCACC ACCTGGATGA     300
GTACGTGCGT GTCTGGGCCG AGTATGACCC CGCAGCTTGg taagaagtca     350
ccccgaatcc tccagccaca atactcacct ctccctggaa ctggaacacg     400
ggctaggcta ggncccccaga ctctggagca ctgaactcct ggggctccta    450
gcagggtct cacaggttca gtcaggagag aagatataag aatcatcacc      500
cttgcatacc ccagattaaa cacgtagggt gccaacctgc ccaaaccctg     550
gaggactttc tgggaaatga ggagggcgtc aaccatgaga tgtctgaaga     600
gccctctcct cctacgagtc tctcctgtct ctcactgtga agtctccaga     650
tggtgaggat cgattagcca ggctccagga gaaaccaaca gact           694
```

Fig. 1A-32

```
//
Submission no  :   34
Intron 36      :   <..213
Exon 37        :   214..310
Intron 37      :   311..> aagggaggtg cctgcagtcc cgaactcgac tgacatccta cacccctggg       50
tctccccagt gtctgggaat gtactgggaa ttcacttgtc cccagtctct      100
cccactcctt gaagccaggg acacccagc ctcgggcatc atgacctcgt       150
tgtgtgccca gggagcccgt gtgaaccat tgcctgcact aaccccsttt      200
cttctccttt cagCGGTCGG ATTCATTATA AGGATATGTA CAGTTTATTA      250
CGAGTAATAT CTCCCCCTCT CGGCTTAGGC AAGAAATGTC CTCATAGGGT      300
TGCTTGCAAG gtttgacttc cactaaaacc tgctagcatc catggaatga      350
gtgtggcttg gggttcttca atatatatat ttcatatata tatatatata      400
tatctctctc tctctaaaaa aacagagcca tctctctttc ttgcattaaa      450
ctagaaaact ctcttagcca acag                                  474
```

Fig. 1A-33

```
//
Submission no  :  35
Intron 37      :  <..82
Exon 38        :  83..188
Intron 38      :  189..>
```

```
cctgggtagg ggcgggcgcg gctcacggga gacccaggag ggatgcctgg         50
gaatgactgc gcttgccttg ggttttctgt agCGGCTTCT GCGGATGGAC        100
CTGCCCGTCG CAGATGACAA CACCGTCCAC TTCAATTCCA CCCTCATGGC        150
TCTGATCCGC ACAGCCCTGG ACATCAAGAT TGCCAAGGgt aaggaaggga        200
caggggcggg cacagacagg cgtgacaggg tggaactggg gatctcctcc        250
ctaccccaaa ctagaggatc tgctgtcacc acccggatct tcattcactc        300
ttccattcat tcgttccaca ggnnttttg gnnnttggnn ntttggtgtt         350
ttttttttt ttttgagaca gagtcttgct ctgttgccca ggcagcagtg         400
cggtgacatg atc                                                413
```

Fig. 1A-34

```
//
Submission no   :   36
Intron 38       :   <..96
Exon 39         :   97..204
Intron 39       :   205..369
Exon 40         :   370..470
Intron 40       :   471..>
```

```
gggtctcgtt ctcgggagcc tatggctttg cagctgaccc agagtccagc      50
tgacacccag gcaggcagtc agggtctgtc tacaccccca ttgcagGAGG     100
AGCCGACAAA CAGCAGATGG ACGCTGAGCT GCGGAAGGAG ATGATGGCGA     150
TTTGGCCCAA TCTGTCCCAG AAGACGCTAG ACCTGCTGGT CACACCTCAC     200
AAGTgtaaga gctgagccca gccctgggat ccaatccacc aggacagatg     250
gaggggagg gaaaggggag gcctgggag agtgttggct gggctggtat       300
acacagggac ccaggacaag gtccccaaag angcctgccc ttggtgagct     350
caccgtgtgt gtcccccagC CACGGACCTC ACCGTGGGGA AGATCTACGC     400
AGCCATGATG ATCATGGAGT ACTACCGGCA GAGCAAGGCC AAGAAGCTGC     450
AGGCCATGCG CGAGGAGCAG gtgcgctgtt cgccgctctg gggacatctg     500
ggctggggac agtggcttgc atgtcaccac gggaaccaac tggaatatga     550
gggtggctga gcccagggc aggtccctga aaagtagggg ctggtgcaca      600
gcagctcaca cctgcaatct cagtgctttg agaggc                    636
```

```
//
Submission no  :  37
Intron 40      :  <..407
Exon 41        :  408..517
Intron 41      :  518..625
Exon 42        :  626..764
Intron 42      :  765..>
Sequence       :  829 gatcttcagg gccatgggag ctgcaggaag gactctggct ttttccccaa    50
         gcaagtggga gccatggagg gttctaagca aaggagggat aggacctgac   100
         tcaagtgctc atgggcgccc tctggtggct cttgtggaac agtggggttg   150
         aaggtaggag cgggagacct gggagaaggt gcctgcagtg agagatgagg   200
         acgcgggacc aggctggggc tatgacttgg gtggaggagt gagaagtggt   250
         ccagttctgc gtggaattgg aagggtctag atggatgaga cctgagagag   300
         tgtgtgtgtg tgtgtgtgtg tatactgggg atgtcgcaat gccttctggg   350
         taccaccgtc caccacccca cccttgtcca cacactgctc tctgccccat   400
         tccccagGAC CGGACACCCC TCATGTTCCA GCGCATGGAG CCCCCGTCCC   450
         CAACGCAGGA AGGGGGACCT GGCCAGAACG CCCTCCCCTC CACCCAGCTG   500
         GACCCAGGAG GAGCCCTgtg agtgtcaccc ctgccaggga ggtggagtgt   550
         gggggtgccg tggtccccac gttctggaag ctgcccaagc gcccactgct   600
         accccggcct ctgtccccca tgcagGATGG CTCACGAAAG CGGCCTCAAG   650
         GAGAGCCCGT CCTGGGTGAC CCAGCGTGCC CAGGAGATGT TCCAGAAGAC   700
         GGGCACATGG AGTCCGGAAC AAGGCCCCCC TACCGACATG CCCAACAGCC   750
         AGCCTAACTC TCAGgtgcct ctgtccccca actcccaat ggctcccagg    800
         gcccgggtgg ttgcggtgga aggaaccat                          829
```

Fig. 1A-36

```
//
Submission no  :  38
Intron 42      :  <..219
Exon 43        :  220..333
Intron 43      :  334..>
```

```
tcactgcaac ctccaccttc cagtctcaag tgattcctcc tgcctcagcc        50
tcccaagtca ctggattaca ggcgcccacc accatgctca ggtatttttt       100
tttgtatttt tagtagagac ggggtttcac aatgttggtc aggctggtct       150
cgaactgctg nccattgtga tctggaggtc aggccccaga gctcatctgg       200
ctttgccatt cgtccgcagT CCGTGGAGAT GCGAGAGATG GGCAGAGATG       250
GCTACTCCGA CAGCGAGCAC TACCTCCCCA TGGAAGGCCA GGGCCGGGCT       300
GCCTCCATGC CCCGCCTCCC TGCAGAGAAC CAGgtgaggg ctttcaccac       350
tgccctgggg ctggacccct cactctgcac tgggtagggc caggcccccc       400
cacaagcagc ccagtgcatc ccctcctgcc ggactcaggc ctgggtaggg       450
actccttcag tctctgaagc agtctgcagg ccccacccac cacctggtca       500
cacctggagc acctgcagac cctcctccct cacagaggac agagaggaaa       550
gtgctccccc tggggcagag ggcagtggcc actgcaaaat ggtctctggc       600
tgccctggtt ggaggctgca gacaggggag gttgtggaar atttgtgggt       650
gcagcagggt tcaacagggc cagctgagac ctgccacgaa gawcctttga       700
ggccaggagt ttgagaccag gttgggcaac atagcaaaac cctgtctctt       750
ttttttttt gagacggagt ttcactcttg ttgcccaggc tggagtgac         800
a                                                            801
```

Fig. 1A-37

```
//
Submission no    :    39
Intron 43        :    <..83
Exon 44          :    84..119
Intron 44        :    120..>
Sequence         :    329 cctcctcact cttccctctt gcctttatat ttattttctt ctttctgttt         50
        tttctgtgtg caccatccat ggggctgtga cagAGGAGAA GGGGCCGGCC        100
        ACGTGGGAAT AACCTCAGTg tatgtacggc ctgcccaggg cccagcaggc        150
        tccggccccc tcttcctccc cacccncct  ccaggagtc  ccgtaatctc        200
        taccggtccc cggaccccac cctttctttg gcaatcgcac cctctcccct        250
        ccatggagcc caatccttgt gtgtggtgtc ctgtgtgtgc cctgacccat        300
        aagcctggtg gggcggccat ccccatcct                              329
```

Fig. 1A-38

```
//
Submission no  :  40
Intron 44      :  <..166
Exon 45        :  167..353
Intron 45      :  354..> gatcagggggg agccaaggcc ccatggcatc ccctggcccc tgccccagga    50
     tggtcacacc gcagtcaccg aaggccacca ccaggctgcc acaatggggc    100
     aggaaggacc gggaccactt ggtgctagct gctgacccca gcccaccggc    150
     ctgtcccctc ccccagACCA TCTCAGACAC CAGCCCCATG AAGCGTTCAG    200
     CCTCCGTGCT GGGCCCCAAG GCCCGACGCC TGGACGATTA CTCGCTGGAG    250
     CGGGTCCCGC CCGAGGAGAA CCAGCGGCAC CACCAGCGGC GCCGCGACCG    300
     CAGCCACCGC GCCTCTGAGC GCTCCCTGGG CCGCTACACC GATGTGGACA    350
     CAGgtgggca gccctgtggt gctcagggac aagcagaaca gaggagagga    400
     gagggagga gaaggcaggg cggaggagac actaaggaag aagaaaggga    450
     gaggcctcca tggagagggg acagagcggg ccaggcagcg gctgcaggaa    500
     cctgggtact accccctccc cccaacccac tgacctgcct cggttcaggg    550
     gatc                                                      554
```

Fig. 1A-39

```
//
Submission no  :  41
Intron 45      :  <..31
Exon 46        :  32..285
Intron 46      :  286..>
```

```
ctgtgtgctg tctgaccctc acccggccca gGCTTGGGGA CAGACCTGAG       50
CATGACCACC CAATCCGGGG ACCTGCCGTC GAAGGAGCGG GACCAGGAGC      100
GGGGCCGGCC CAAGGATCGG AAGCATCGAC AGCACCACCA CCACCACCAC      150
CACCACCACC ATCCCCCGCC CCCCGACAAG GACCGCTATG CCCAGGAACG      200
GCCGGACCAC GGCCGGGCAC GGGCTCGGGA CCAGCGCTGG TCCCGCTCGC      250
CCAGCGAGGG CCGAGAGCAC ATGGCGCACC GCCAGgtggg tgcggctgca      300
agtgacccca ggctgggctc ggccgggagg cggggaggag agaaggggat      350
acccatcca acagccactc taggcaaagg tccccggatc ccggctgtga       400
ccacctccca tcctgccccc aagccaccgg ggtgcccggc ggccggagcg      450
gagcacggat c                                                461
```

Fig. 1A-40

```
//
Submission no  :  42
Intron 46      :  <..279
Exon 47        :  280..>
Stop codon     :  280..282
UTR 3'         :  283..>
```

```
tttctcattt ctcttttcac ttttgttgtg ttggtttccg actcctcccc        50
tccctgtctc actcccccctc ctcccctccc tcctccctgt ggctgttgct      100
ttttccatt caatgtcctg tgtccccccct ctcctcctcc tcctcctcct      150
ccccctcctc cctctcctcc cggcccctct cccttcgctc ccctcatctt      200
cctcccaatc ccgtgtctcc tttgattttg ttgtatcttt ttttttgatt      250
tcctttgttt caattttcgt gtagggcagT AGTTCCGTAA GTGGAAGCCC      300
AGCCCCCTCA ACATCTGGTA CCAGCACTCC GCGGCGGGGC CGCCGCCAGC      350
TCCCCCAGAC CCCCTCCACC CCCCGGCCAC ACGTGTCCTA TTCCCCTGTG      400
ATCCGTAAGG CCGGCGGCTC GGGGCCCCCG CAGCAGCAGC AGCAGCAGCA      450
GCAGCAGCAG CAGGCGGTGG CCAGGCCGGC CGGCGGCCA CCAGCGGCCC       500
TCGGAGGTAC CCAGGCCCCA CGGCCGAGCC TCTGGCCGGA GATCGGCGCC      550
CACGGGGGGC CACAGCAGCG GCCGCACGCC CAGGATGGAG AGGCGGGTCC      600
AGGCCCGGCC CGGAGCGAGT CTCCAGGGCC TGGTCGACAC GGCGGGGCCC      650
GGCTGGCGGC AGTC                                             664
```

Fig. 1A-41

```
atggcccgcttcggagacgagatgccggcccgctacggggggaggaggctccggggcagcc    60
 M  A  R  F  G  D  E  M  P  A  R  Y  G  G  G  S  G  A  A       20
gccggggtggtcgtgggcagcggaggcgggcgaggagccggggcagccggcagggcggg     120
 A  G  V  V  V  G  S  G  G  G  R  G  A  G  G  S  R  Q  G  G    40
cagccggggcgcaaaggatgtacaagcagtcaatggcgcagagagcgcggaccatggca    180
 Q  P  G  A  Q  R  M  Y  K  Q  S  M  A  Q  R  A  R  T  M  A    60
ctctacaaccccatccccgtccgacagaactgcctcacggttaaccggtctctcttcctc    240
 L  Y  N  P  I  P  V  R  Q  N  C  L  T  V  N  R  S  L  F  L    80
ttcagcgaagacaacgtggtgagaaaatacgccaaaaagatcaccgaatggcctcccttt    300
 F  S  E  D  N  V  V  R  K  Y  A  K  K  I  T  E  W  P  P  F   100
gaatatatgattttagccaccatcatagcgaattgcatcgtcctcgcactggagcagcat   360
 E  Y  M  I  L  A  T  I  I  A  N  C  I  V  L  A  L  E  Q  H   120
ctgcctgatgatgacaagaccccgatgtctgaacggctggatgacacagaaccatacttc    420
 L  P  D  D  D  K  T  P  M  S  E  R  L  D  D  T  E  P  Y  F   140
attggaattttttgtttcgaggctggaattaaaatcattgcccttgggtttgccttccac    480
 I  G  I  F  C  F  E  A  G  I  K  I  I  A  L  G  F  A  F  H   160
aaaggctcctacttgaggaatggctggaatgtcatggactttgtggtggtgctaacgggc    540
 K  G  S  Y  L  R  N  G  W  N  V  M  D  F  V  V  V  L  T  G   180
atcttggcgacagttgggacggagtttgacctacggacgctgagggcagttcgagtgctg    600
 I  L  A  T  V  G  T  E  F  D  L  R  T  L  R  A  V  R  V  L   200
cggccgctcaagctggtgtctggaatcccaagtttacaagtcgtcctgaagtcgatcatg    660
 R  P  L  K  L  V  S  G  I  P  S  L  Q  V  V  L  K  S  I  M   220
aaggcgatgatccctttgctgcagatcggcctcctcctattttttgcaatccttatttt    720
 K  A  M  I  P  L  L  Q  I  G  L  L  L  F  F  A  I  L  I  F   240
gcaatcatagggttagaatttatatgggaaaatttcataccacctgctttgaagagggg    780
 A  I  G  L  E  F  Y  M  G  K  F  H  T  T  C  F  E  E  G      260
acagatgacattcagggtgagtctccggctccatgtgggacagaagagcccgccgcacc    840
 T  D  D  I  Q  G  E  S  P  A  P  C  G  T  E  E  P  A  R  T   280
tgccccaatgggaccaaatgtcagccctactgggaagggcccaacaacgggatcactcag    900
 C  P  N  G  T  K  C  Q  P  Y  W  E  G  P  N  N  G  I  T  Q   300
ttcgacaacatcctgtttgcagtgctgactgttttccagtgcataaccatggaagggtgg    960
 F  D  N  I  L  F  A  V  L  T  V  F  Q  C  I  T  M  E  G  W   320
actgatctcctctacaataacaacgatgcctcagggaacacttggaactggttgtacttc   1020
 T  D  L  L  Y  N  S  N  D  A  S  G  N  T  W  N  W  L  Y  F   340
atccccctcatcatcatcggctcctttttttatgctgaaccttgtgctggggtgtgctgtca   1080
 I  P  L  I  I  I  G  S  F  F  M  L  N  L  V  L  G  V  L  S   360
ggggagtttgccaaagaaagggaacggggtggagaaccggcgggcttttctgaagctgagg   1140
 G  E  F  A  K  E  R  E  R  V  E  N  R  R  A  F  L  K  L  R   380
cggcaacaacagattgaacgtgagctcaatgggtacatggaatggatctcaaaagcagaa   1200
 R  Q  Q  Q  I  E  R  E  L  N  G  Y  M  E  W  I  S  K  A  E   400
gaggtgatcctcgccgaggatgaaactgacggggagcagaggcatccctttgatggagct   1260
 E  V  I  L  A  E  D  E  T  D  G  E  Q  R  H  P  F  D  G  A   420
ctgcggagaaccaccataaagaaaagcaagacagatttgctcaaccccgaagaggctgag   1320
 L  R  R  T  T  I  K  K  S  K  T  D  L  L  N  P  E  E  A  E   440
gatcagctggctgatatagcctctgtgggttctcccttcgcccgagccagcattaaaagt   1380
 D  Q  L  A  D  I  A  S  V  G  S  P  F  A  R  A  S  I  K  S   460
gccaagctggagaactcgaccttttttcacaaaaaggagaggaggatgcgtttctacatc   1440
 A  K  L  E  N  S  T  F  F  H  K  K  E  R  R  M  R  F  Y  I   480
cgccgcatggtcaaaactcaggccttctactggactgtactcagtttggtagctctcaac   1500
 R  R  M  V  K  T  Q  A  F  Y  W  T  V  L  S  L  V  A  L  N   500
acgctgtgtgttgctattgttcactacaaccagcccgagtggctctccgacttcctttac   1560
 T  L  C  V  A  I  V  H  Y  N  Q  P  E  W  L  S  D  F  L  Y   520
tatgcagaattcattttcttaggactctttatgtccgaaatgtttataaaaatgtacggg   1620
 Y  A  E  F  I  F  L  G  L  F  M  S  E  M  F  I  K  M  Y  G   540
cttgggacgcggccttacttccactcttccttcaactgctttgactgtggggttatcatt   1680
 L  G  T  R  P  Y  F  H  S  S  F  N  C  F  D  C  G  V  I  I   560
gggagcatcttcgaggtcatctgggctgtcataaaacctggcacatcctttggaatcagc   1740
```

Fig. 4

```
  G   S   I   F   E   V   I   W   A   V   I   K   P   G   T   S   F   G   I   S         580
gtgttacgagccctcaggttattgcgtattttcaaagtcacaaagtactgggcatctctc                             1800
  V   L   R   A   L   R   L   L   R   I   F   K   V   T   K   Y   W   A   S   L         600
agaaacctggtcgtctctctcctcaactccatgaagtccatcatcagcctgttgtttctc                             1860
  R   N   L   V   V   S   L   L   N   S   M   K   S   I   I   S   L   L   F   L         620
cttttcctgttcattgtcgtcttcgccttttgggaatgcaactcttcggcggccagttt                              1920
  L   F   L   F   I   V   V   F   A   L   L   G   M   Q   L   F   G   G   Q   F         640
aatttcgatgaagggactcctcccaccaacttcgatacttttccagcagcaataatgacg                             1980
  N   F   D   E   G   T   P   P   T   N   F   D   T   F   P   A   A   I   M   T         660
gtgtttcagatcctgacgggcgaagactggaacgaggtcatgtacgacgggatcaagtct                             2040
  V   F   Q   I   L   T   G   E   D   W   N   E   V   M   Y   D   G   I   K   S         680
caggggggcgtgcagggcggcatggtgttctccatctatttcattgtactgacgctcttt                             2100
  Q   G   G   V   Q   G   G   M   V   F   S   I   Y   F   I   V   L   T   L   F         700
gggaactacacCCtcctgaatgtgttcttggccatcgctgtggacaatctggccaacgcc                             2160
  G   N   Y   T   L   L   N   V   F   L   A   I   A   V   D   N   L   A   N   A         720
caggagctcaccaaggacgagcaagaggaagaagaagcagcgaaccagaaacttgcccta                             2220
  Q   E   L   T   K   D   E   Q   E   E   E   A   A   N   Q   K   L   A   L             740
cagaaagccaaggaggtggcagaagtgagtcctctgtccgcggccaacatgtctatagct                             2280
  Q   K   A   K   E   V   A   E   V   S   P   L   S   A   A   N   M   S   I   A         760
gtgaaagagcaacagaagaatcaaaagccagccaagtccgtgtgggagcagcggaccagt                             2340
  V   K   E   Q   Q   K   N   Q   K   P   A   K   S   V   W   E   Q   R   T   S         780
gagatgcgaaagcagaacttgctggccagccgggaggccctgtataacgaaatggacccg                             2400
  E   M   R   K   Q   N   L   L   A   S   R   E   A   L   Y   N   E   M   D   P         800
gacgagcgctggaaggctgcctacacgcggcacctgcggccagacatgaagacgcacttg                             2460
  D   E   R   W   K   A   A   Y   T   R   H   L   R   P   D   M   K   T   H   L         820
gaccggccgctggtggtggacccgcaggagaaccgcaacaacaacaccaacaagagccgg                             2520
  D   R   P   L   V   V   D   P   Q   E   N   R   N   N   N   T   N   K   S   R         840
gcggccgagcccaccgtggaccagcgcctcggccagcagcgcgccaggacttcctcagg                              2580
  A   A   E   P   T   V   D   Q   R   L   G   Q   Q   R   A   E   D   F   L   R         860
aaacaggcccgctaccacgatcgggcccgggaccccagcggctcggcgggcctggacgca                             2640
  K   Q   A   R   Y   H   D   R   A   R   D   P   S   G   S   A   G   L   D   A         880
cggaggccctgggcggggaagccaggaggccgagctgagccgggaggacccctacggccgc                            2700
  R   R   P   W   A   G   S   Q   E   A   E   L   S   R   E   D   P   Y   G   R         900
gagtcggaccaccacgcccggggagggcagcctggagcaacccgggttctggggagggcgag                           2760
  E   S   D   H   H   A   R   E   G   S   L   E   Q   P   G   F   W   E   G   E         920
gccgagcgaggcaaggccggggaccccaccggaggcacgtgcaccggcaggggggcagc                              2820
  A   E   R   G   K   A   G   D   P   H   R   R   H   V   H   R   Q   G   G   S         940
agggagagccgcagcgggtccccgcgcacgggcgcggacggggagcatcgacgtcatcgc                             2880
  R   E   S   R   S   G   S   P   R   T   G   A   D   G   E   H   R   R   H   R         960
gcgcaccgcaggcccggggaggagggtccggaggacaaggcggagcggagggcgcggcac                             2940
  A   H   R   R   P   G   E   E   G   P   E   D   K   A   E   R   R   A   R   H         980
cgcgagggcagccggccggcccggggcggcgagggcgagggcgaggtcccgacggggc                               3000
  R   E   G   S   R   P   A   R   G   G   E   G   E   G   P   D   G   G                1000
gagcgcaggagaaggcaccggcatggcgctccagccacgtacgaggggacgcgcggagg                              3060
  E   R   R   R   R   H   R   H   G   A   P   A   T   Y   E   G   D   A   R   R        1020
gaggacaaggagcggaggcatcggaggaggaaagagaaccagggctccggggtccctgtg                             3120
  E   D   K   E   R   R   H   R   R   R   K   E   N   Q   G   S   G   V   P   V        1040
tcgggccccaacctgtcaaccacccggccaatccagcaggacctgggccgccaagaccca                             3180
  S   G   P   N   L   S   T   T   R   P   I   Q   Q   D   L   G   R   Q   D   P        1060
cccctggcagaggatattgacaacatgaagaacaacaagctggccaccgcggagtcggcc                             3240
  P   L   A   E   D   I   D   N   M   K   N   N   K   L   A   T   A   E   S   A        1080
gctccccacggcagccttggccacgccggcctgccccagagcccagccaagatgggaaac                             3300
  A   P   H   G   S   L   G   H   A   G   L   P   Q   S   P   A   K   M   G   N        1100
agcaccgaccccggccccatgctggccatccctgccatggccaccaaccccagaacgcc                              3360
  S   T   D   P   G   P   M   L   A   I   P   A   M   A   T   N   P   Q   N   A        1120
gccagccgccggacgcccaacaacccggggaacccatccaatcccggcccccccaagacc                             3420
  A   S   R   R   T   P   N   N   P   G   N   P   S   N   P   G   P   P   K   T        1140
```

Fig. 4A

```
cccgagaatagccttatcgtcaccaaccccagcggcacccagaccaattcagctaagact   3480
 P   E   N   S   L   I   V   T   N   P   S   G   T   Q   T   N   S   A   K   T      1160
gccaggaaacccgaccacaccacagtggacatcccccagcctgcccacccccctcaac     3540
 A   R   K   P   D   H   T   T   V   D   I   P   P   A   C   P   P   P   L   N      1180
cacaccgtcgtacaagtgaacaaaaacgccaacccagacccactgccaaaaaaagaggaa   3600
 H   T   V   V   Q   V   N   K   N   A   N   P   D   P   L   P   K   K   E   E      1200
gagaagaaggaggaggaggaagaagacgaccgtggggaagacggccctaagccaatgcct   3660
 E   K   K   E   E   E   E   D   D   R   G   E   D   G   P   K   P   M   P         1220
ccctatagctccatgttcatcctgtccacgaccaacccccttcgccgcctgtgccattac   3720
 P   Y   S   S   M   F   I   L   S   T   T   N   P   L   R   R   L   C   H   Y      1240
atcctgaacctgcgctactttgagatgtgcatcctcatggtcattgccatgagcagcatc   3780
 I   L   N   L   R   Y   F   E   M   C   I   L   M   V   I   A   M   S   S   I      1260
gccctggccgccgaggaccctgtgcagcccaacgcacctcggaacaacgtgctgcgatac   3840
 A   L   A   A   E   D   P   V   Q   P   N   A   P   R   N   N   V   L   R   Y      1280
tttgactacgttttacaggcgtctttaccttgagatggtgatcaagatgattgacctg    3900
 F   D   Y   V   F   T   G   V   F   T   F   E   M   V   I   K   M   I   D   L      1300
gggctcgtcctgcatcagggtgcctacttccgtgacctctggaatattctcgacttcata   3960
 G   L   V   L   H   Q   G   A   Y   F   R   D   L   W   N   I   L   D   F   I      1320
gtggtcagtggggccctggtagcctttgccttcactggcaatagcaaaggaaaagacatc   4020
 V   V   S   G   A   L   V   A   F   A   F   T   G   N   S   K   G   K   D   I      1340
aacacgattaaatccctccgagtcctccgggtgctacgacctcttaaaaccatcaagcgg   4080
 N   T   I   K   S   L   R   V   L   R   V   L   R   P   L   K   T   I   K   R      1360
ctgccaaagctcaaggctgtgtttgactgtgtggtgaactcacttaaaaacgtcttcaac   4140
 L   P   K   L   K   A   V   F   D   C   V   V   N   S   L   K   N   V   F   N      1380
atcctcatcgtctacatgctattcatgttcatcttcgccgtggtggctgtgcagctcttc   4200
 I   L   I   V   Y   M   L   F   M   F   I   F   A   V   V   A   V   Q   L   F      1400
aaggggaaattcttccactgcactgacgagtccaaagagtttgagaaagattgtcgaggc   4260
 K   G   K   F   F   H   C   T   D   E   S   K   E   F   E   K   D   C   R   G      1420
aaataccteetctacgagaagaatgaggtgaaggcgcgagaccgggagtggaagaagtat   4320
 K   Y   L   L   Y   E   K   N   E   V   K   A   R   D   R   E   W   K   K   Y      1440
gaattccattacgacaatgtgctgtgggctctgctgaccctcttcaccgtgtccacggca   4380
 E   F   H   Y   D   N   V   L   W   A   L   L   T   L   F   T   V   S   T   A      1460
gaaggctggccacaggtcctcaagcattcggtggacgccacctttgagaaccagggcccc   4440
 E   G   W   P   Q   V   L   K   H   S   V   D   A   T   F   E   N   Q   G   P      1480
agcccgggtaccgcatggagatgtccatttttctacgtcgtctactttgtggtgttcccc   4500
 S   P   G   Y   R   M   E   M   S   I   F   Y   V   V   Y   F   V   V   F   P      1500
ttcttctttgtcaatatctttgtggccttgatcatcatcaccttccaggagcaaggggac   4560
 F   F   F   V   N   I   F   V   A   L   I   I   I   T   F   Q   E   Q   G   D      1520
aagatgatggaggaatacagcctggagaaaaatgagagggcctgcattgatttcgccatc   4620
 K   M   M   E   E   Y   S   L   E   K   N   E   R   A   C   I   D   F   A   I      1540
agtgccaagccgctgacccgacacatgccgcagaacaagcagagcttccagtaccgcatg   4680
 S   A   K   P   L   T   R   H   M   P   Q   N   K   Q   S   F   Q   Y   R   M      1560
tggcagttcgtggtgtctccgcctttcgagtacacgatcatggccatgatcgccctcaac   4740
 W   Q   F   V   V   S   P   P   F   E   Y   T   I   M   A   M   I   A   L   N      1580
accatcgtgcttatgatgaagttctatggggcttctgtggcttatgaaaatgccctgcgg   4800
 T   I   V   L   M   M   K   F   Y   G   A   S   V   A   Y   E   N   A   L   R      1600
gtgttcaacatcgccttcacctcccttcttctctctggaatgtgtgctgaaagccatggct   4860
 V   F   N   I   A   F   T   S   L   F   S   L   E   C   V   L   K   A   M   A      1620
tttgggattctgaattatttccgcgatgcctggaacatcttcgactttgtgactgttctg   4920
 F   G   I   L   N   Y   F   R   D   A   W   N   I   F   D   F   V   T   V   L      1640
ggcagcatcaccgatatcctcgtgactgagtttgggaataacttcatcaacctgagcttt   4980
 G   S   I   T   D   I   L   V   T   E   F   G   N   N   F   I   N   L   S   F      1660
ctccgcctcttccgagctgcccggctcatcaaacttctccgtcagggttacaccatccgc   5040
 L   R   L   F   R   A   A   R   L   I   K   L   L   R   Q   G   Y   T   I   R      1680
attcttctctggacctttgtgcagtccttcaaggccctgccttatgtctgtctgctgatc   5100
 I   L   L   W   T   F   V   Q   S   F   K   A   L   P   Y   V   C   L   L   I      1700
gccatgctcttcttcatctatgccatcattgggatgcaggtgtttggtaacattggcatc   5160
```

Fig. 4B

```
A  M  L  F  F  I  Y  A  I  I  G  M  Q  V  F  G  N  I  G  I              1720
gacgtggaggacgaggacagtgatgaagatgagttccaaatcactgagcacaataacttc            5220
D  V  E  D  E  D  S  D  E  D  E  F  Q  I  T  E  H  N  N  F              1740
cggaccttcttccaggccctcatgcttctcttccggagtgccaccggggaagcttggcac            5280
R  T  F  F  Q  A  L  M  L  L  F  R  S  A  T  G  E  A  W  H              1760
aacatcatgctttcctgcctcagcggggaaaccgtgtgataagaactctggcatcctgact           5340
N  I  M  L  S  C  L  S  G  K  P  C  D  K  N  S  G  I  L  T              1780
cgagagtgtggcaatgaatttgcttatttttactttgtttccttcatcttcctctgctcg            5400
R  E  C  G  N  E  F  A  Y  F  Y  F  V  S  F  I  F  L  C  S              1800
tttctgatgctgaatctctttgtcgccgtcatcatggacaactttgagtacctcacccga            5460
F  L  M  L  N  L  F  V  A  V  I  M  D  N  F  E  Y  L  T  R              1820
gactcctccatcctgggcccccaccacctggatgagtacgtgcgtgtctgggccgagtat            5520
D  S  S  I  L  G  P  H  H  L  D  E  Y  V  R  V  W  A  E  Y              1840
gaccccgcagcttgcggtcggattcattataaggatatgtacagtttattacgagtaata            5580
D  P  A  A  C  G  R  I  H  Y  K  D  M  Y  S  L  L  R  V  I              1860
tctcccctctcggcttaggcaagaaatgtcctcatagggttgcttgcaagcggcttctg             5640
S  P  P  L  G  L  G  K  K  C  P  H  R  V  A  C  K  R  L  L              1880
cggatggacctgcccgtcgcagatgacaacaccgtccacttcaattccaccctcatggct            5700
R  M  D  L  P  V  A  D  D  N  T  V  H  F  N  S  T  L  M  A              1900
ctgatccgcacagccctggacatcaagattgccaagggaggagccgacaaacagcagatg            5760
L  I  R  T  A  L  D  I  K  I  A  K  G  G  A  D  K  Q  Q  M              1920
gacgctgagctgcggaaggagatgatggcgatttggcccaatctgtcccagaagacgcta            5820
D  A  E  L  R  K  E  M  M  A  I  W  P  N  L  S  Q  K  T  L              1940
gacctgctggtcacacctcacaagtccacgacctcaccgtggggaagatctacgcagcc             5880
D  L  L  V  T  P  H  K  S  T  D  L  T  V  G  K  I  Y  A  A              1960
atgatgatcatggagtactaccggcagagcaaggccaagaagctgcaggccatgcgcgag            5940
M  M  I  M  E  Y  Y  R  Q  S  K  A  K  K  L  Q  A  M  R  E              1980
gagcaggaccggacacccctcatgttccagcgcatggagcccccgtccccaacgcaggaa            6000
E  Q  D  R  T  P  L  M  F  Q  R  M  E  P  P  S  P  T  Q  E              2000
gggggacctggccagaacgccctccctccacccagctggacccaggaggagccctgatg             6060
G  G  P  G  Q  N  A  L  P  S  T  Q  L  D  P  G  G  A  L  M              2020
gctcacgaaagcggcctcaaggagagcccgtcctgggtgacccagcgtgcccaggagatg            6120
A  H  E  S  G  L  K  E  S  P  S  W  V  T  Q  R  A  Q  E  M              2040
ttccagaagacgggcacatggagtccggaacaaggccccctaccgacatgcccaacagc             6180
F  Q  K  T  G  T  W  S  P  E  Q  G  P  P  T  D  M  P  N  S              2060
cagcctaactctcagtccgtggagatgcgagagatgggcagagatggctactccgacagc            6240
Q  P  N  S  Q  S  V  E  M  R  E  M  G  R  D  G  Y  S  D  S              2080
gagcactactctccccatggaaggccagggccgggctgcctccatgccccgcctccctgca          6300
E  H  Y  L  P  M  E  G  Q  G  R  A  A  S  M  P  R  L  P  A              2100
gagaaccagaggagaaggggccggccacgtggaataacctcagtaccatctcagacacc            6360
E  N  Q  R  R  R  G  R  P  R  G  N  N  L  S  T  I  S  D  T              2120
agccccatgaagcgttcagcctccgtgctgggccccaaggcccgacgcctggacgattac           6420
S  P  M  K  R  S  A  S  V  L  G  P  K  A  R  R  L  D  D  Y              2140
tcgctggagcgggtcccgccccgaggagaaccagcggcaccaccagcggcgccgcgaccgc          6480
S  L  E  R  V  P  P  E  E  N  Q  R  H  H  Q  R  R  R  D  R              2160
agccaccgcgcctctgagcgctccctgggccgctacaccgatgtggacacaggcttgggg           6540
S  H  R  A  S  E  R  S  L  G  R  Y  T  D  V  D  T  G  L  G              2180
acagacctgagcatgaccacccaatccggggacctgccgtcgaaggagcgggaccaggag           6600
T  D  L  S  M  T  T  Q  S  G  D  L  P  S  K  E  R  D  Q  E              2200
cggggccggcccaaggatcggaagcatcgacagcaccaccaccaccaccaccaccaccac            6660
R  G  R  P  K  D  R  K  H  R  Q  H  H  H  H  H  H  H  H  H              2240
catccccgcccccgacaaggaccgctatgcccaggaacggccggaccacggccgggca             6720
H  P  P  P  P  D  K  D  R  Y  A  Q  E  R  P  D  H  G  R  A              2260
cgggctcgggaccagcgctggtcccgctcgcccagcgagggccgagagcacatggcgcac           6780
R  A  R  D  Q  R  W  S  R  S  P  S  E  G  R  E  H  M  A  H              2280
cggcagtag                                                                6786
R  Q  *                                                                  2282
```

Fig. 4C

GENE RELATED TO MIGRAINE IN MAN

Migraine is a frequent paroxysmal neuro-vascular disorder, characterized by recurrent attacks of disabling headache, vomiting, photo/phonophobia, malaise, and other general symptoms (migraine without aura). Up to 20% of patients may, in addition, experience transient neurological (aura) symptoms during attacks (migraine with aura) (HCC, 1988). Up to 24% of females and 12% of males in the general population are affected, however with variable attack frequency, duration and severity (Russell et al., 1995). Knowledge about the mechanisms of the final common pathway of migraine attacks has increased substantially the last five years, resulting in improved, though still only symptomatic (and sub-optimal) acute treatment for the attack. There is, however, still very little knowledge about the etiology of migraine attacks, i.e. why and how attacks begin and recur. Accordingly, prophylactic treatment for migraine is non-specific and has only limited efficacy.

Family, twin and population-based studies suggest that genetic factors are involved In migraine, most likely as part of a multifactorial mechanism (reviewed by Haan et al., 1996). The complex genetics has hampered identification of candidate genes for migraine. Familial Hemiplegic Migraine (FHM) is a rare, autosomal dominant, subtype of migraine with aura, associated with ictal hemiparesis and, in some families cerebellar atrophy (HCC, 1988). Otherwise, the symptoms of the headache and aura phase of FHM and "normal" migraine attacks are very similar and both types of attacks may alternate within subject and co-occur within families. FHM is thus part of the migraine spectrum and can be used as a model to study the complex genetics of the more common-forms of migraine (Haan et al., 1996). A gene for FHM has been assigned to chromosome 19p13 in about half of the families tested (Joutel et al., 1993; Ophoff et al., 1994; Joutel et al., 1995). Remarkably, cerebellar atrophy was found only in families with FHM linked to chromosome 19p13, but not in unlinked families. Recently, we showed the 19p13 FHM locus to be also involved in "normal" migraine (May et al., 1995).

Episodic ataxia type 2 (EA-2) is another, autosomal dominant, paroxysmal neurological disorder, characterized by acetazolamide-responsive attacks of cerebellar ataxia and migraine-like symptoms, and interictal nystagmus and cerebellar atrophy. Recently, a gene for EA-2 was assigned to chromosome 19p13, within the same interval as for FHM (Kramer et al., 1995). This finding, as well as the clinical similarities, raise the possibility of EA-2 and FHM being allelic disorders.

Since other hereditary episodic neurological disorders responding to acetazolamide (such as hypokalaemic and hyperkalaemic periodic paralysis), as well as EA type-1 A (which, in contrast to EA-2, is associated with continuous myokymia and non-responsive to acetazolamide) have all been associated with mutations in genes encoding for ion channels (Ptacek et al., 1991; Ptacek et al., 1994; Brown et al., 1994), we specifically looked for similar genes within the FHM and EA-2 candidate region.

In view of the above, the FHM/EA-2 locus can, since FHM is part of the migraine spectrum, thus be used to study the genetic factors and biological mechanisms that are related to various episodic neurological disorders such as FHM, EA-2, common migraine and others such as epilepsy.

Calcium channels are multisubunit complexes composed of at least an α1, an α2δ, and a β subunit. The central α1 subunit is functionally the most important component, acting as a voltage sensor and forming the ion-conducting pore. The other subunits have auxiliary regulatory roles. The membrane topology of the α1 subunit consist of four hydrophobic motifs (I to IV), each containing six transmembrane α-helices (S1–S6) and one hairpin (P) between S5–S6 that spans only the outer part of the transmembrane region.

The present invention provides an isolated and/or recombinant nucleic acid, or fragments thereof, encoding a $Ca^{2+}$-channel α1 subunit related to familial hemiplegic migraine and/or episodic ataxia type-2, derived from a gene present on chromosome 19p13.1–19p13.2; a gene encoding the α1 (ion-conducting) subunit of a P/Q-type voltage gated calcium channel. The present invention also provides access to and methods to study the genetic background and identify other subunits of the calcium channel subunit complexes and the proteins related therewith that are associated with the genetic factors and biological mechanisms that are related to various episodic neurological disorders such as FHM, EA-2, common migraine and others such as epilepsy which are related to cation channel dysfunction.

The sequence of the cDNA of the gene is highly related ($\geq 90\%$) to a brain-specific rabbit and rat voltage gated P/Q-type calcium channel al subunit (Mori et al., 1991; Starr et al., 1991), and the open reading frame consists of 2261 amino acid residues. Northern blot analysis showed a brain-specific expression, especially in the cerebellum. Primary study of a cosmid contig harbouring the gene already indicated an exon distribution over at least 300 kb of genomic DNA. Recently, a neuronal $Ca^{2+}$ α1A subunit gene was localized to chromosome 19p13.1–p13.2 by FISH analysis (Diriong et al, 1995). The gene symbol is CACNL1A4 and the al subunit is classified as a P/Q-type. No sequence data for the CACNL1A4 gene have been provided by Diriong or others, but the same localization (chromosome 19p13.1) and the identical classification (P/Q-type) suggests that the $Ca^{2+}$ channel α1 subunit we have identified is very similar to CACNL1A4. No relation with migraine has been disclosed for CACNL1A4. The genomic structures of three other human $Ca^{2+}$ channel α1 subunit genes (CACNL1A1, CACNL1A2 and CACNL1A3) have been published to date (Hogan et al, 1994; Soldatov, 1994; Yamada et al, 1995). Both CACNL1A1 and CACNL1A2 span about 150 kb and consist of 50 and 49 exons, respectively. The smaller CACNL1A3 gene is composed of 44 exons, distributed over 90 kb.

The present invention also provides an isolated and/or recombinant nucleic acid comprising alleles of the invented gene which contain mutations relevant to the occurence of migraine and other neurological disorders which are related to cation channel dysfunction. Such mutations are for example a mutation at codon 192 resulting in the replacement of arginine by glutamine (R192Q), and/or a mutation at codon 666 resulting in the replacement of threonine by methionine, and/or a mutation at codon 714 resulting in a replacement of valine by alanine and/or a mutation at codon 1811 resulting in a replacement of isoleucine by leucine, but also other mutations of alleles of said gene which bear relationships with cation channnel dysfunction.

The present invention also provides isolated and/or recombinant nucleic acid comprising alleles of said gene which contain a polymorphic CA-repeat sequence specific for various alleles of said gene. The present invention also provides isolated and/or recombinant nucleic acids comprising alleles of said gene which contain a CAG repeat.

The present invention also provides methods and tests (such as PCR, but also other tests to detect or amplify nucleic acids are known in the art) to detect, identify and localize or distinguish genes and alleles of such genes, or fragments thereof, encoding for proteins or α, β or χ sub-units of specific cerebral cation channels, more specifically the invented gene and its various alleles encoding the α1 subunit of a P/Q-type voltage gated calcium channel and the gene encoding the β2 sub-unit, which are involved in the primary pathogenesis of neurological disorders such as FHM, migraine, EA-2 and SCA6. With such methods and tests one can study abnormalities of said gene.

The invention also provides recombinant expression vectors comprising isolated and/or recombinant nucleic acid comprising alleles of said genes or fragments therof, and provides host cells or animals that comprise such vectors or that are otherwise transformed with an isolated and/or recombinant nucleic acid according to the invention.

The invention thus also provides a rationale and methods for the testing and the development of specific prophylactic medication for migraine and other episodic neurological, in particular brain, disorders, such as epilepsy, associated with cation channel dysfunction.

The invention for example provides cells or animals that comprise recombinant vectors that comprise variants of said genes or cells or animals that are transformed with said variants. Also, the invention provides means to identify naturally occuring variants of experimental animals with changes in said gene related to FHM, EA-2, SCA7, migraine or other neurological disorders associated with cation channel dysfunction. An example of such an animal is the tottering mouse, and its variants called leaner and rolling, described in the experimental part of the invention. The invention also provides cells or animals in which changes such as deletions or mutations in said gene have been introduced by recombinant nucleic acid techniques. All such cells or animals provided by the invention can be used to study the pathophysiology of FHM, EA-2, migraine or other neurological disorders associated with cation channel dysfunction, for example to test or develop specific medication for the treatment of said disorders.

The invention also provides proteins or peptides encoded by said genes, or fragments thereof, related with cation channel dysfunction, and detection of such proteins or peptides by antibodies directed against said proteins or peptides. Such antibodies can be of natural or synthetic origin, and can be produced by methods known in the art. Such proteins and antibodies and detection methods can be used to further in vitro or in vivo studies towards the pathophysiology of FHM, EA-2, migraine or other neurological disorders associated with cation channel dysfunction, in addition such proteins, antibodies and detection methods can also be used to diagnose or identify such disorders in patients or in experimental animals.

Experimental Procedures

Subjects

Sixteen FHM patients were selected, including eight individuals from four unrelated chromosome 19-linked FHM families (NL-A, UK-B, USA-C (Ophoff et al, 1994), and USA-P (Elliot et al., 1995), two affected individuals from two small FHM families from Italy (Italy I & II) and six individuals with sporadic hemiplegic migraine (i.e. no other family member was shown to suffer from attacks of hemiplegic migraine). In families NL-A and USA-P cerebellar ataxia and/or nystagmus is associated with FHM. An additional set of four subjects from four unrelated EA-2 families linked to chromosome 19, was also included (CAN-25, -45, -191, -197. Fifty randomly collected individuals from the Dutch population (Smith et al., 1988) were used as a control to determine the allele frequencies of polymorphic sites.

Patients with migraine with or without aura were diagnosed according to the international Headache-Society (IHS) classification criteria. Patients attending the neurology outpatient clinic of Leiden University Medical Center, The Netherlands, and patients responding to calls in local newspapers or in the periodical of the Dutch Migraine Patients Association, were screened for a positive family history of migraine. Only families with migraine in at least two generations were asked to participate. Probands (n=36) and relatives (n=492) were personally examined and interviewed using semi-structured questionnaires. The questionnaire included questions about age at onset, frequency and duration of attacks, aura symptoms, premonitory signs and symptoms, triggers for attacks, medication, and additional headaches. When family members were not available for a personal interview, information on their migraine was collected by interviewing their relatives. Because of the low validity of diagnosing migraine auras through relatives, we only assessed the presence or absence of migraine headaches. Whenever possible, medical records were examined.

Genomic Structure

Ten different cosmids from the contig extending the invented gene, were subcloned separately in either M13 or pBlueScript KS vector. From each cosmid library at least 3×96 random clones with an average insert size of about 2 kb, were picked. Positive clones were identified by hybridization techniques and subsequently sequenced with vector-specific primers; intron-exon boundary sequences were completed using cDNA-based primers.

Mutation Analysis, DHPLC and SSCP

Genomic DNA was used as template to generate polymerase chain reaction (PCR) products for single-strand conformational polymorphism (SSCP) analysis and denaturing high-performance liquid chromatography (DHPLC). Amplifications were performed in standard conditions with primer pairs as listed in Table 1 or listed below. Except for the 5' side of exon 6, primers were chosen to produce fragments that contained a single exon and at least 35 basepairs (including primer) of each flanking intron sequence. Amplification of exons 1 and 20 was performed producing two overlapping fragments and exon 19 was amplified into three overlapping fragments. In addition, the following markers;

D10S191 Primer sequence 1 (SEQ ID NO: 141) CTT TAA TTG CCC TGT CTT C

Primer sequence 2 (SEQ ID NO: 142) TTA ATT CGA CCA CTT CCC

D10S245 Primer sequence 1 (SEQ ID NO: 143) AGT GAG ACT CGT CTC TAA TG

Primer sequence 2 (SEO ID NO: 144) ACC TAC CTG AAT TCC TGA CC

DIOS89 Primer sequence 1 (SEQ ID NO: 145) AAC ACT AGT GAC ATT ATT TTC A

Primer sequence 2 (SEQ ID NO: 146) AGC TAG GCC TGA AGG CTT CT

DHPLC (Oefner et al., 1995; Hayward et al., 1996) was carried out on automated HPLC instrumentation. Crude PCR products, which had been subjected to an additional 3-minute 95° C. denaturing step followed by gradual reannealing from 95–65° C. over a period of 30 minutes prior to analysis, were eluted with a linear acetonitrile (9017-03, J. T. Baker, Phillipsburg, N.J., USA) gradient of 1.8% per minute at a flow-rate of 0.9 ml/min. The start- and endpoints of the gradient were adjusted according to the size of the PCR products (Huber et al., 1995). The temperature required for successful resolution of heteroduplex molecules was determined empirically by injecting one PCR product of each exon at increasing mobile phase temperatures until a significant decrease in retention was observed.

For SSCP analysis, primary PCR products were labeled by incorporation of [α-$^{32}$P]dCTP in a second round of PCR. Samples were diluted and denatured in formamide buffer before electrophoresis. SSCP was carried out according to published protocols (Orita et al., 1989; Glavac et al., 1994). Digestion of several exons to yield products suitable for SSCP analysis.

Sequencing of PCR products was performed with an ABI 377 automated sequencing apparatus with cycle sequencing according to the manufacturer. Furthermore, PCR products were cloned in the TA vector (Invitrogen) and subjected to manual dideoxy sequence analysis (T7 Sequencing kit, Pharmacia Biotech.).

A total of 481 blood samples were collected from patients with migraine. Genomic DNA was isolated as described by Miller et al., 1988. The analyses of the highly informative microsatellite markers D19S391, D19S394, D19S221 and D19S226, D10S191, D10S248 and D10S89 were performed by PCR; primer sequences related to these markers are available through the human Genome Data Base (GDB).

The relative frequencies of marker alleles were estimated on the entire family material, with the relevant correction for genetic relationships between individuals (Boehnke, M, 1991) with the ILINK option of the I-INKAGE package, version 5.03 (Lathrop et al., 1985). The following marker order and recombination frequencies were used in the multipoint sib-pair analysis: D19S391-5%-D19S394-3%-D19S221-5%-D19S226. Affected-sib-pair analysis was performed using the MAPMAKER/SIBS software package, simultaneously including marker information for all four DNA markers (Kruglyak, 1995). Separate analyses were performed for migraine with aura, migraine without aura, and a combination of both. Allowance was made for dominance variance. When more than two affected sibs occurred in a single sibship, weighted scores were computed according to Suarez and Hodge (1979).

In a sib-pair analysis, the occurrence of parental marker alleles is compared among sibs. Normally, 25% of sib pairs share their marker alleles from both parents, 50% share one marker allele from one of their parents, while the remaining 25% share no parental allele. Deviations from this pattern towards increased sharing, and consistent with the constraints of Holmans's (1993) possible triangle, are explained as linkage (expressed as the maximum lod score MLS). Increased sharing of marker alleles thus indicate that the marker is located closely near a genetic risk factor. The relative-risk ratio for a sib ($\lambda_R$), defined as the ratio of the prevalence of a disease in sibs of affected individuals, divided by the prevalence of a disease in the population, can be calcutated (May et al., 1995). In other words:

$$\lambda_p = \frac{\text{Affected risk for sib of a proband}}{\text{Affection risk for an individual in the general population}}$$

Results

Genomic Structure

The combination of hybridization and PCR strategies resulted in a rapid assembly of the complete coding sequence of the human cDNA, with an open reading frame of 6783 nucleotides encoding 2261 amino acid residues (FIG. 4). The spatial distribution of the human Ca$^2$+ channel expression was assayed in rhesus monkey tissues. Total RNA was isolated from several tissues, including various brain structures, and probed with a human cDNA fragment. The probe detected a major transcript of approximately 9.8 kb in cerebellum, cerebral cortex, thalamus and hypothalamus, whereas no transcript was detected in heart, kidney, liver or muscle. There was also no hybridization signal found in RNA preparations from mouse skin tissue or from human peripheral lymphocytes. In addition, an attempt to amplify parts of the cDNA from human peripheral lymphocytes failed.

Complete alignment between the cDNA and individual exon sequences was achieved, allowing the establishment of the exon-incron structure (Table 1). The reconstruction of the exon-intron structure of the CACNL1A4 gene revealed 47 exons ranging in size from 36 bp (exon 44) to 810 bp (exon 19). The exons are distributed over about 300 kb at genomic DNA level. The result shows that the first 10 exons are located in a region of about 150 kb covered by the first 5 cosmids of the contig indicating relatively large introns at 5' side of the gene. Sequences (FIG. 1) were obtained of all exons including approximately 100 bp of flanking introns, except for intron 5 adjacent to exon 6. The forward primer of exon 6 harbours the splice junction and 3 bp of exon 6. Splice sites around all exons are compatible with consensus sequence with the exception of splice donor and acceptor of the first intron.

The cosmid conzig that yielded the initial Ca$^2$+ channel gene exons was extended to cover more than 300 kb. Hybridization experiments showed that the first and last cosmids of the contig were positive for 3'- and 5'-end cDNA sequences, respectively, indicating a genomic distribution of the gene over at least 300 kb (FIG. 2). The cosmid contig has been placed into the LLNL physical map of chromosome 19 at band p13.1, between the markers D19S221 and D19S226 (FIG. 2). We identified a new polymorphic CA-repeat sequence (D19S1150) on the cosmid contig. Oligonucleotide primers (Table 1) flanking the repeat were synthesized and amplification was performed by PCR as described. Analysis of D19S1150 in 45 random individuals from the Dutch population revealed nine alleles with an observed heterozygosity of 0.82. This highly polymorphic marker is located within the gene and is therefore very useful in genetic analysis.

Mutation Analysis

Exons and flanking intron sequences, containing the complete coding region of CACNL1A4 and part of untranslated sequences, were screened for the presence of mutations by SSCP and DHPLC analysis in 20 individuals with either FHM or EA-2. Several synonymous nucleotide substitutions and polymorphisms were identified including a highly polymorphic (CAG)n-repeat in the 3' untranslated region of exon 47 (Table 2). Of all polymorphisms only one was identified predicting an amino acid change, an alanine to threonine substitution at codon 454 (A454T).

Four different missense mutations were found in FHM patients of which one mutation was observed in two unrelated FHM affected individuals (Table 3). The mutations were shown to segregate with the disease within the families, and were not present in about 100 control chromosomes. A G-to-A transition was identified in family Italy-II at codon 192, resulting in a substitution of arginine to glutamine (R192Q) within the first voltage sensor domain (IS4). A second missense mutation occurs at codon 666, within the P-segment of the second repeat replacing a threonine residue for methione (T666M) in family USA-P. Two other mutations are located in the 6th transmembrane spanning segment of respectively repeat II and IV. The IIS6 mutation is a T-to-C transition at codon 714, resulting in a substitution of valine to alanine (V714A), identified in FHM family UK-B. The mutation in domain IVS6 is an A-to-C transversion at codon 1811 resulting in a substitution of isoleucine to leucine (I1811L). This I1811L mutation is found in family NL-A and family USA-C, two unrelated FHM families. Comparison of haplotypes in this region, including intragenic markers, did not reveal any evidence for a common founder of family NL-A and USA-C (data not shown). No mutation was found in FHM family Italy-I nor in the six sporadic hemiplegic migraine patients. In addition to missense mutations in FHM families, we also identified mutations in two out of four EA-2 families (Table 3). In EA-2 family CAN-191, a basepair deletion occurs in exxon 22 at nucleotide position 4073 causing a frameshift and a premature stop. The second EA-2 mutation is a transition of G-to-A of the first nucleotide of intron 24, predicted to leading to an aberrant splicing in family CAN-26. The invented gene also contains a CAG repeat, of which expansions have been found in patients with autosomal dominant cerebellar ataxia (SCA6). Hence FHM, EA-2 and SCA6 are alielic ion channel disorders and different mutations are associated with different clinical symptomatologies.

Our study patients with common migraine (with or without aura) included 36 independent multigenerational Dutch families. At least some data were available on 937 family members and 212 persons who "married-in" (spouses). Of these, 442 family members (247 affected) and 86 spouses (7 affected) were personally interviewed. The distribution of the different types of migraine among the 247 affected family members are as follows: 132 family members showed migraine without aura, 93 showed migraine with aura and 22 showed months-migraine, not fulfilling all critera by IHS. Among the 7 affected spouses these figures were 4, 1 and 2, respectively. We scored the parental transmission of migraine in the 36 families (Tabel 4) to investigate if an additional X-linked dominant or mitachondrial aene was involved. An approximately 2.5:1 preponderance of females among the migraine sufferers was noted, which remained in the affected offspring. Affected fathers were found to transmit migraine to their sons in 21 cases, making X-linked dominant or mitochondrial inheritance highly unlikely.

The genetic analysis included 204 potentially affected sib pairs; after correction for more than one sib pair in a single sibship the total number of sib pairs was 108. Affected-sib-pair analysis was performed for sib pairs who were both affected with any form of migraine and, in separate analyses, for sib pairs who where both suffering from either migraine with aura or migraine without aura. The informativeness of the region between the markers D19S391, D19S394, D19S221 and D19S226 varied between 82% and 96%. The combined analysis of migraine with and without aura resulted in a maximum multipoint lod score of 1.69 (p≈0.005) with marker D19S226. For migraine with aura the maximum multipoint lod score was 1.29 corresponding with p≈0.013 with marker D19S394. The maximum lod score for migraine without aura was not significant (MLS <0.25)(data not shown). The relative risk ratio for a sib to suffer from migraine with aura ($\lambda_p$), defined as the increase in risk of the trait attributable to the 19p13 locus, varied between $\lambda_R$=1.5 (for marker D19S394) and $\lambda_R$=2.4 (for marker D19S226). When combining migraine with and without aura, $\lambda_R$ was 1.25. In a selected portion of 36 Dutch families with migraine with aura and without aura, affected sib-pair analysis was performed for sib pairs who were affected with any form of migraine. The following markers, flanking the β2(CACNB2) calcium channel subunit gene on chromosome 10p12, were tested: D10S191, D1OS246 and D10S89. For the combined phenotype (migraine with and without aura) a maximum pultipoint iod score of 0,95 (p<0,01) was obtained with marker; D10S191. This result gives independent evidence for a role of the P/Q type $Ca^{2+}$ channel in migraine and other neurological disorders.

Discussion

The genomic structure of the exemplified invented gene revealed 47 exons distributed over about 300 kb (Table 1; FIG. 1). A comparison of the gene structure to already known $Ca^{2+}$ channel al subunit genes (CACNL1A1, CACNL1A2, and CACNL1A3) (Soldatov, 1994; Yamada et al., 1995; Hogan et al., 1995), reveals a similar number of exons (50, 49, and 44 respectively) but a larger genomic span (300 kb vs 90–150 kb). Remarkebly, all splice sites are according to consensus sequence except for intron 1. Splice donor as well as splice acceptor of the first intron do not contain the expected gt . . . ag intron sequence. An incorrect CDNA sequence is unlikely because the cDNA sequence containing the junction of the first two exons is identical to rabbit and rat sequence. Sequences corresponding to splice donor and acceptor are present in exon 1 and 2, suggesting an additional (yet unidentified) exon in the first intron encompassing part of sequences of exon 1 and exon 2.

To test the possible involvement of the invented gene relating to the $CA^{2+}$-channel sub-unit in migraine FHM, SCA6 and EA-2, we performed a mutation analysis by DHPLC and SSCP and found several alterations (For example Table 2 & 3). Only one missense variation was observed also present in 2% of the normal controls (Table 2). This polymorphism is a alanine to threonine substitution at codon 454 (A454T), located in the intracellular loop between IS6 and IIS1 (FIG. 2). This region contains a conserved alpha interaction domain (AID) that binds sub-units (De Waard et al., 1996). However, A454T is located outside the AID consensus sequence and is not likely to be involved.

The identification of two mutations that disrupt the predicted translation product of the invented gene in two unrelated EA-2 patients and the segregation of these mutations with the episodic ataxia phenotype in their families provide strong evidence that the invented gene is the EA-2 gene. A basepair deletion leads to a frame-shift in the putative translation product and encounters a stop codon in the next exon. The frame-shift in this EA-2 family is predicted to yield a calcium channel al subunit polypeptide consisting of repeat I and II, and a small portion of repeat III (IIIS1). The G-to-A transition of the first nucleotide of intron 24 is affecting the nearly invariant GT dinucleotide of the intronic 5' splice junction. The brain-specific expression of the exemplified invented gene makes it extremely difficult to test the hypothesis that this mutation produces aberrantly spliced RNAs by retaining the intron or utilizing other cryptic 5' splice sites.

The frameshift and splice site mutations in EA-2 may suggest a dominant negative effect of the truncated proteins by overruling the (corresponding) intact al subunits.

No mutations were found in the remaining EA-2 families (CAN-25 and -197). The use of two independent techniques for mutation screening (DHPLC and SSCP) makes it unlikely that we missed a heterozygote PCR product. Mutations in the promoter region or in intron sequences, resulting in aberrant splicing, may have been the cause of EA-2 in these families. We could also have missed a mutation around the splice acceptor site of intron 5, covered by the forward primer of exon 6. However, larger deletions of e.g. complete exons with flanking intron sequence will disturb the predicted translation product, like the $\Delta C_{4073}$ and splice site mutation do, but this is not detectable by a PCR-based screening method but can be seen Southern blot analysis instead.

Figure 3:
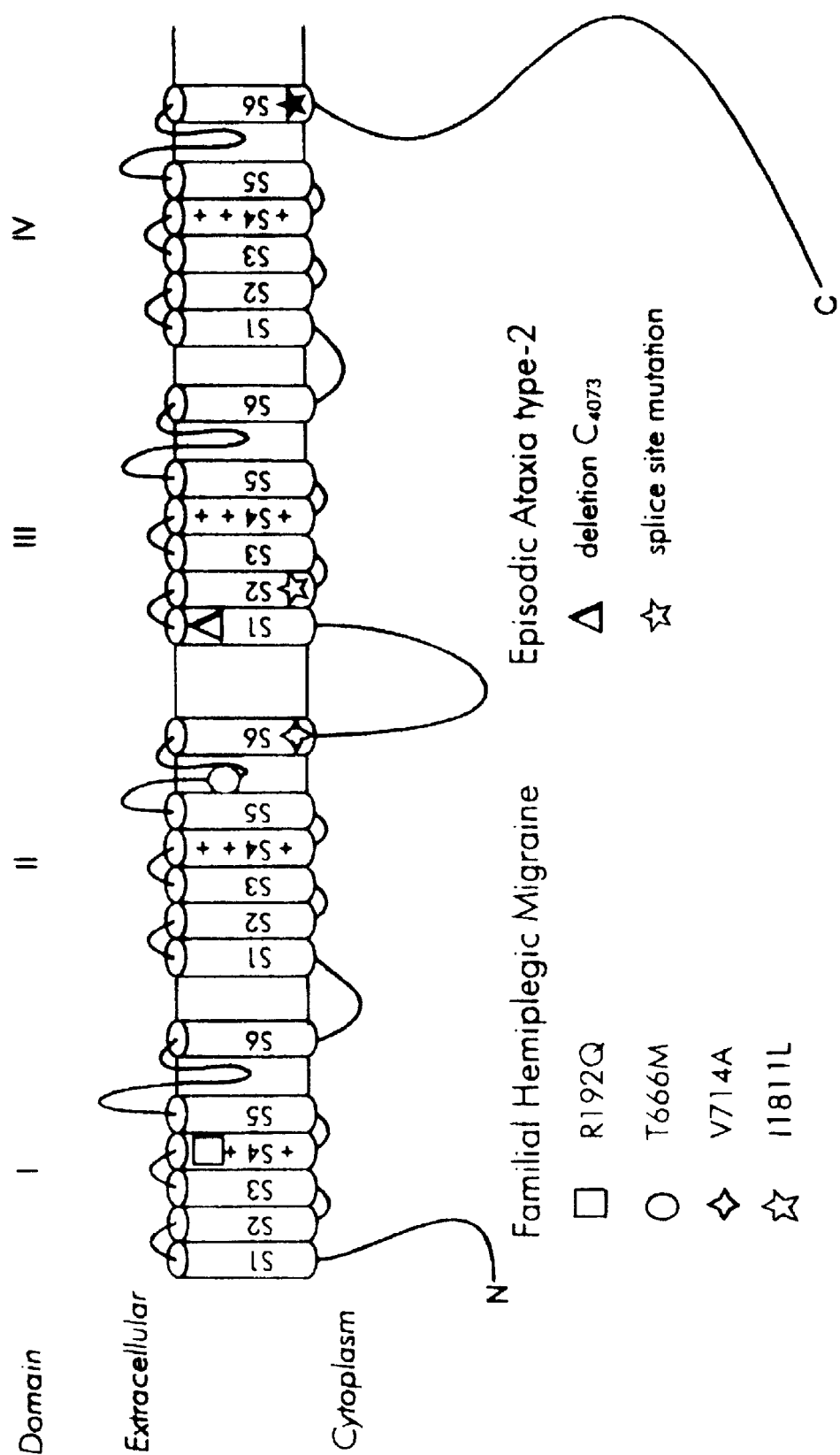

Four different missense mutations were identified in five unrelated FHM families. These mutations all segregate with FHM within a family and are not observed in over 100 normal chromosomes. The first missense mutation that we describe in the exemplified invented gene occurs in the IS4 domain of the al subunit (Table 3; FIG. 3). The S4 domains are postulated to be voltage sensors because they have an unusual pattern of positively charged residues at every third or fourth position separated by hydrophobic residues (Tanabe et al., 1987). In calcium channels the positively charged amino acid is an arginine residue (Stea et al., 1995). The mutation in FHM family Italy-II predicts a substitution of the first arginine in the IS4 segment with a neutral, non-polar alutamine (R192Q). The change of the net positive charge of this conserved region of the protein may influence correct functioning of the voltage sensor.

The second missense mutation in FHM family USA-P occurs in the P-segment of the second transmembrane repeat. A C-to-T transition predicts substitution of a threonine residue with methionine at codon 666 (T666M). Various observations have shown that P-segments, the hairpin between S5 and S6 that spans only the outer part of the transmembrane region, form the ion-selectivity filter of the pore and binding sites for toxins (Guy and Durell (1996). Alignment of protein sequence of different P-segments indicating that some residues occur in many different channel genes (Guy and Durell, 1996). The T666M substitution alters one of the conserved residues in the P-segment. It is conceivable that an alteration of a P-segment affects the ion-selectivity or toxin binding of a channel gene.

The remaining two missense mutations identified in FHM families alter the S6 segment of the second and the fourth repeat. A valine to alanine substitution in FHM family UK-B is found in domain IIS6 at codon 714 (V714A). Domain IVS6 is mutated in two unrelated FHM families (NL-A and USA-C), predicting a isoleucine to leucine substitution at codon 1811 (I1811L). The V714A and I1811L missense mutations do not really change the neutral-polar nature of the amino acid residues. However, both S6 mutations are located nearly at the same residue at the intracellular site of the segment and are conserved in all calcium channel al subunit genes. In addition, the A-to-C transversion leading the I1811L substitution occurred in two unrelated FHM families on different haplotypes indicating recurrent mutations rather than a founder effect. Although the exact function of the S6 domains are not known, these data strongly suggest that mutations in IIS6 and IVS6 result in FHM.

The I1811L mutation is present in two FHM families of which one (NL-A) also displays a cerebellar atrophy in (some) affected family members. The presence of cerebellar atrophy in FHM families has been reported in about 40% of chromosome 19-linked FHM families, whereas none of the unlinked families was found to have cerebellar atrophy (Terwindt et al., 1996).

The I1811L mutation excludes the possibility of allelic mutations in FHM and FHM with cerebellar atrophy. However, it is likely that FHM or FHM with cerebellar atrophy are the result of pleiotropic expression of a single defective gene.

No mutation was found in a small Italian FHM family (Italy-I). Apart from the possibilities discussed for EA-2, it should be noted that linkage to 19p13 was only suggested but never proved with significant lod scores (M. Ferrari, personal knowledge).

The four missense mutations identified indicate a mechanism for FHM in which both alleles of the α1 subunit are expressed, one harbouring an amino acid substitution which affects the function of this calcium channel α1 subunit by reducing or enhancing the electrical excitability. The relationship of FHM and other types of migraine makes it highly rewarding to investigate the involvement of the only missense variant observed (A454T) (Table 2), and to continue the search for other variants of the exemplified invented gene specific for common types of migraine.

The mutations in EA-2 and FHM demonstrate among others that the brain specific calcium channel gene CACNL1A4 is responsible for both EA-2 and FHM, and is also involved in the primary pathogenesis of the more common forms of migraine. We conducted the common migraine study in an independent sample of 36 extended Dutch families, with migraine with aura and migraine without aura. We found significant increased sharing of the marker alleles in sibs with migraine with aura (MLS=1.29 corresponding with p≈0.013). Although no such increased sharing was found for migraine without aura, a combined analysis for both migraine types resulted in an even more significant increased sharing (MLS=1.69 corresponding with p≈0.005). These results clearly indicate the involvement of the calcium cSIA-subunit gene region on 19p13 in both migraine with and without aura; the contribution to migraine with aura, however, seems strongest.

The positive findings in our study clearly demonstrate an involvement of the FHM locus region in non-hemiplegic familial migraine, notably in migraine with aura. The P/Q-type calcium channel $\alpha_{1A}$-subunit gene on chromosome 19p13 may be an "aura-gene" and is involved in both FHM and migraine with aura, but not in migraine without aura. This however, seems unlikely since an increased sharing of marker alleles was also found when we combined the results for migraine with and without aura. Furthermore, the increase in sharing was stronger than expected to be only due to the contribution of migraine with aura. An alternative explanation is that the gene is involved in both types of migraine, but in migraine without aura there is an additional strong effect of other, possibly environmental factors, thereby reducing the penetrance.

The latter view is also supported by the results obtained from calculating the relative risk ratios ($\lambda_R$) for sibs from affected individuals to also have migraine. The relative risk ratio for a sib to suffer from migraine with aura was $\lambda_R$=2.4. When combining migraine with and without aura, $\lambda_R$ was 1.25. In a population-based study the relative risk for first degree relatives of probands with migraine with aura to also have migraine with aura was $\lambda_R$=3.8. Because of the female preponderance among migraine patients, X-linked dominant or mitochondrial inheritance has been suggested to be involved in familial migraine. Although a predominant maternal inheritance pattern was noted in our families, X-linked dominant or mitochondrial inheritance were found to be highly unlikely because affected fathers transmit migraine to their sons. Furthermore, the predominant maternal inheritance can be explained by the female preponderance among the migraine patients.

We conclude that the well-established genetic contribution to the etiology of migraine is partly, but not entirely, due to genetic factors located in the chromosomal region of the P/Q-type calcium channel $\alpha_{1A}$-subunit gene. Further analysis of the cerebral distribution and function of this calcium channel, as well as of the "mutated channels", will help to unravel the pathogenetic pathway of migraine. It may also contribute to a better understanding of the mechanisms involved in related disorders such as episodic ataxia type-2, autosomal dominant cerebellar ataxia (SCA6), cerebral atrophy, and epilepsy, which all have been found to be associated with mutations in this gene. Study of FHM, EA-2 mutants and variants such as the A454T variant expressed in vitro or in mouse or other experimental animal models will ultimately lead to better understanding of the diseases, their cellular mechanisms, and the clinical relationship between FHM, EA-2, migraine, and other episodic neurological disorders such as epilepsy, and will provide rationales for the development of prophylactic therapy.

Localization and identification of the mouse gene related to the neurological mouse mutations tottering, leaning and rolling.

The tottering (tg) mutation arose spontaneously in the DBA inbred strain, and has been back-crossed into a C57BL/6J (B6) inbred strain for at least 30 generations. The genome of the tg mouse therefore is of B6 origin except for a small region around the tg gene on chromosome 8. Interestingly, the chromosome 8 region in mouse has synteny with the human chromosome 19p13.1, in which the human calcium channel alpha1 subunit has been identified. We therefore consider the tg locus as a possible site of the mouse homologue of the human calcium channel gene.

To determine the exact localization of the mouse homologue, PCR was carried out with primers based on human cDNA sequence selected from FIG. 1 and mouse genomic DNA aE template. In human, primers were known to be located in different flanking exons. POR amplification on human DNA yielded a 1.5kb fragment.

Forward primer (SEQ ID NO: 45)5'-caa cat cat gct ttc ctg cc-3'

Reversed primer (SEQ ID NO: 46)5'-atg atg acg gcg aca aag ag-3'

Amplification on mouse DNA yielded a 750-bp fragment. The fragment mainly consists of intronic sequences. SSCP analysis revealed several polymorphisms in the different inbred strains (each strain a specific pattern). Analysis of amplified product of the tg/tg (homozygote) and tg/+ (heterozygote) mice demonstrated a DBA specific signal in the tg/tg mouse, and a heterozygous pattern of DBA and B6 inbred strains in the heterozygous tg/+mouse. These results show that the mouse homologue of the human calcium channel alpha1 subunit is located within the mouse tottering interval on chromosome 8.

In conclusion: the phenotypic characteristics of the tg mouse (tg/tg and tg/+) suggest involvement of ion-channels in the tg-etiology. The localization of the mouse homologue of the human calcium gene within the tottering interval show that a tottering phenotype in mouse is caused by a mutation in the mouse homologue of the CACNL1A4 gene. With various variants of the tottering mouse (the Jackson Laboratory, Bar Habor, Me., USA), such as the leaner and rolling varieties, such mutations in the mouse homologue of the CACNL1A4 gene can be found, clearly demonstrating that the gene is related to a variety of episodic neurologic disorders and using this genetic information one can engage in a variety of pathofysiological studies, as for example indicated below.

The tg mutation arose spontaneously in the DBA/2 inbred strain. tg/tg homozygotes are characterized by a wobbly gait affecting the hindquarters in particular, which begins at about 3 to 4 weeks of age, and by intermittent spontaneous seizures which resemble human epileptic absence seizures. The central nervous system of the mice appears normal by light microscopy. There is no discernible cerebellar hypoplasia. In fluorescent histochemistry studies tg/tg mice show a marked increase in number of noradrenergic fibers in the terminal fields innervated by locus ceruleus axons, the hippocampus, cerebellum, and dorsal lateral geniculate. Treatment of neonatal tg/tg mice with 6-hydroxydopamine, which selectively causes degeneration of distal noradrenergic axons from the locus ceruleus, almost completely abolishes the ataxic and seizure symptoms.

The leaner mutation of the tottering mouse arose spontaneously in the AKR/J strain. Homozygotes are recognized at 8 to 10 days of age by ataxia, stiffness, and retarded motor activity. Adults are characterized by instability of the trunk, and hypertonia of trunk and limb muscles. The cerebellum is reduced in size, particularly in the anterior region, in tg<la>/tg<la>mice, as is the case with a certain number of FHM patients. There is loss of granule cells beginning at 10 days of age and loss of Purkinje and Golgi cells beginning after 1 month. Cell loss later slows but continues throughout life. Granule and Purkinje cells are more severely affected than Golgi cells and the anterior folia more severely affected than other parts of the cerebellum. The cerebellum of tg<la>/tg mice shows shrinkage and degenerative changes of the Purkinje cells. The loss in cerebellar volume in tg<la>/tg and in tg/tg mice is specific to the molecular layer, with no change in volume of the granule cell layer or the white matter layer. Allelism of aleaner with tottering was shown in complementation and linkage tests.

A third variety of the tottering mouse is (tg<rol>) called the rolling Nagoya. Found among descendants of a cross between the SIII and C57BL/6 strains, the tg<rol>mutation apparently occurred in the SIII strain. Homozygotes show poor motor coordination of hindlimbs that may lead to falling and rolling, and sometimes show stiffness of the hindlimbs and tail. No seizures have been observed. Symptoms are recognizable at 10 to 14 days old. They appear a little earlier than those of tg/tg mice and are somewhat more severe. The cerebellum is grossly normal until 10 days of age, but after that grows more slowly than normal. The size of the anterior part of the central lobe of the cerebellum is reduced with reduction in the numbers of granule, basket, and stellate cells but normal numbers of Purkinje cells. There is a reduced concentration of glutamate and an increased concentration of glycine and taurine in the cerebellum and decreased activity of tyrosine hydroxylase in the cerebellum and other areas.

LEGENDS TO FIGURES

FIG. 1

Nucleic acid sequences of 47 exons and flanking intron sequences containing the complete coding region of the invented gene and part of untranslated sequences SEQ ID NO: 41–SEQ ID NO: 42.

FIG. 2

Genetic map, cosmid contig and global exon distribution of the invented gene om chromosome 19p13.1. The cosmid contog is shown with EcoRI restriction sites, available via Lawrence Livermore National Laboratory; exon positions are indicated schematically, regardless of exon or intron sizes (Table 1). D19S1150 is a highly polymorpmic intragenic $(Ca)_{n-repeat}$.

FIG. 3

Membrane topology of α1 subunit of the P/Q-type $Ca^{2+}$-channel. The location and amino acid substitutions are indicated for mutations that cause FHM or EA-2.

FIG. 4

The coding sequence SEQ ID NO:43 of human cDNA of the invented gene with an open reading frame encoding 2261 amino acid residues SEQ ID NO: 44.

REFERENCES

1. Browne, D. L., Gancher S. T, Nutt, J. G., Brunt, E. R., Smith E. A., Kramer P., and Litt M. (1994). Episodic ataxia/myokymia syndrome is associated with point mutations in the human potassium channel gene, KCNA1. *Nat. Genet.* 8: 136–140.
2. Diriong S., Lory P., Williams M. E., Ellis S. B., Harpold M. M., and Taviaux S. (1995). Chromosomal localization of the human genes for α1A, α1B, and α1E voltage-dependent $Ca^{2+}$ channel subunits. *Genomics* 30: 605–609.
3. Headache Classification Committee (HCC) of the International Headache Society (1988). Classification and diagnostic criteria for headache disorders, cranial neuralgias and facial pain *Cephalalgia* 8: 19–28.
4. Hogan, K.,Powers, P. A., and Gregg, R. G. (1994). Cloning of the human skeletal muscle alpha 1 subunit of the dihydropyridine-sensitive L-type calcium channel (CACNL1A3). *Genomics* 24: 608–609.
5. Joutel A., Bousser M-G., Biousse V., Labauge P., Chabriat H., Nibbio A.,Maciazek J., Meyer B., Bach M-A., Weissenbach J., Lathrop G. M., and Tournier-Lasserve E. (1993). A gene for familial hemiplegic migraine maps to chromosome 19. *Nature Genet.* 5: 40–45.
6. Joutel A., Ducros A., Vahedi K., Labauge P., Delrieu O., Pinsard N., Mancini J., Ponsat G., Gaoftiere F., Gasant J. L., Maziaceck J. Weissenbach J., Bousser M. G., and Tournier-Lasserve E. (1994). Genetic heterogeneity of familial hemiplegic migraine. *Am. J. Hum. Genet.* 55: 1166–1172.
7. Hayward-Lester, A., Chilton, B. S., Underhill, P. A., Oefner, P. J., Doris, P. A. (1996). Quantification of specific nucleic acids, regulated RNA processing and genomic polymorphisms using reversed-phase HPLC.
In: F. Ferr (Ed.), Gene Quantification, Birkhuser Verlag, Basel, Switzerland.
8. Huber, C. G., Oefner, P. J., Bonn, G. K. (1995) Rapid and accurate sizing of DNA fragments by ion-pair chromatography on alkylated nonporous poly(styrene-divinylbenzene) particles. *Anal. Chem.*, 67, 578–585.
9. Kramer P. L., Yue Q., Gancher S. T., Nutt J. G., Baloh R., Smith E., Browne D., Bussey K., Lovrien E., Nelson S, and Litt M. (1995). A locus for the nystagmus-associated form of episodic ataxia maps to an 11-cM region on chromosome 19p. *Am. J. Hum. Genet.* 57: 182–185.
10. May A, Ophoff R. A., Terwindt G. M., Urban C., Van Eijk R., Haan J., Diener H. C., Lindhout D., Frants R. R., Sandkuiji L. A., and Ferrari M. D. (1995). Familial hemiplegic migraine locus on 19p13 is involved in the common forms of migraine with and without aura. *Hum. Genet.* 96: 604–608.
11. Mori Y, Friedrich T., Kim M. S., Mikami A., Nakai J., Ruth P., Bosse E., Hofmann F., Flockerzi V., Furuichi T., Mikoshiba K. Imoto K., Tanabe T., and Numa S. (1991). Primary structure and functional expression from complementary DNA of a brain calcium channel. *Nature* 350: 398–402.
12. Oefner, P. J., Underhill, P. A. (1995) Comparative DNA sequencing by denaturing high-performance liquid chromatography (DHPLC). *Am. J. Hum. Genet.* 57 [Suppl.], A266.
13. Ophoff R. A., Van Eijk R., Sandkuijl L. A., Terwindt G. M., Grubben C. P. M., Haan J., Lindhout D., Ferrari M. D., and Frants R. R. (1994). Genetic heterogeneity of familial hemiplegic migraine. *Genomics* 22: 21–26.
14. Orita, M., Suzuki, Y., Sekiya, T., and Hayashi, K. (1989). Rapid and sensitive detection of point mutations and DNA polymorphisms using the polymerase chain reaction. *Genomics* 5: 874–879.
15. Ptacek L. J., George A. L., Griggs R. C., Tawil R., Kallen R. G., Barchi R. L., Robertson M., and Leppert M. F. (1991). IdentifLication of a mutation in the gene causing hyperkalemic periodic paralysis. *Cell* 67: 1021–1027.
16. Ptacek L. J., Tawil R., Griggs R. C., Engel A. G., Layzer R. B., Kwiecinski H., McManis P. G., Santiago L., Moore M., Fouad G., Bradley P., and Leppert M. F. (1994). Dihydropyridine receptor mutations cause hypokalemic periodic paralysis. *Cell* 77: 863–868.
17. Ravnik-Glavac, M., Glavac D., and Dean, M. (1994). Sensitivity of single-strand conformation polymorphism and heteroduplex method for mutation detection in the cystic fibrosis gene. Hum. *Mol. Genet.* 3: 801–807.
18. Russell, M. B., Rasmussen B K., Thorvaldsen P., and Olesen J. (1995). Prevalence and sex-ratio of the subtypes of migraine. *Int. J Epidemiol.* 24: 612–618.
19. Starr T. V. B., Prystay W., and Snutch T. (1991). Primary structure of a calcium channel that is highly expressed in the rat cerebellum. *Proc. Natl. Acad. Sci.* 88: 5621–5625.
20. Soldatov N. M. (1994) Genomic structure of Human L-type $Ca^{2+}$ channel. Genomics 22: 77–87.
21. Teh B. T., Silburn P., Lindblad K., Betz R., Boyle R., Schalling M., and Larsson C. (1995). Familial periodic cerebellar ataxia without myokymia maps to a 19-cM region on 19p13. *Am. J. Hum. Genet.* 56: 1443–1449.
22. Terwindt G. M., Ophoff R. A., Haan J., Frants R. R., and Ferrari M. D. (1996). Familial hemiplegic migraine: a clinical comparison of families linked and unlinked to chromosome 19. *Cephalagia* 16: 153–155.
23. Von Brederlow, B., Hahn, A. F., Koopman, W. J., Ebers, G. C., and Bulman, D. (1995). Mapping the gene for acetozolamide responsive hereditary paroxysmal cerebellar ataxia to chromosome 19p. *Hum. Mol. Genet.* 2: 279–284.
24. Yamada Y., Masuda K., Li Q., Ihara Y, Kubota A., Miura T., Nakamura K., Fujii Y., Seino S., and Seino Y. (1995) The structures of the Human Calcium channel α1 subunit (CACNL1A2) and β-subunit (CACNLB3) genes. *Genomics* 27: 312–319.

TABLE 1

Exon/intron organization of the human invented gene and exon-specific primer pairs

| Exon | cDNA | Size | Domain | Cosmid(s) | Primer Forward | Primer Reversed | Size |
|---|---|---|---|---|---|---|---|
| 1 | UTR–568 | 500 | | 25960/30151 | tct ccg cag tcg tag ctc ca 53 | ggt tgt aga gtg cca tgg tc 87 | 320 |
| | | | | | cgc aaa gga tgt aca agc ag 54 | att ccc aag cct cca ggg tag 88 | 370 |
| 2 | 569–674 | 106 | I S1 | 30151 | cac ctc caa cac cct tct tt 55 | tct gtg ccc tgc tcc act c 89 | 240 |
| 3 | 675–814 | 140 | I S2, I S3 | 30151 | acg ctg acc ttg cct tct ct 56 | caa cca aaa gcc tcg taa tc 90 | 230 |
| 4 | 815–906 | 92 | I S3, I S4 | 28913 | aaa acc cac cct ctg ttc tc 57 | ttg tca ggg tcg gaa act ca 91 | 160 |
| 5 | 907–1059 | 153 | | 28913/27415 | ctt ggt ggc ggg gtt t 58 | ctg cct aat cct ccc aag ag 92 | 290 |
| 6 | 1060–1253 | 194 | | 27415 | tcc ctt ccc ttt tgt aga tg 59 | gtg ggg ctg tgt tgt ctt t 93 | 350 |
| 7 | 1254–1357 | 104 | I S6 | 27415 | gac aga gcc aca aga gaa cc 60 | agc aaa gag gag tga gtg gg 44 | 250 |
| 8 | 1358–1473 | 116 | | 34077/27415 | ata ctc tgg ctt ttc tat gc 61 | gca tga ctc tct ttg tac tc 95 | 230 |
| 9 | 1474–1530 | 57 | | 34077 | gca gag aat ggg ggt gg 62 | ctg agg tgg gtt tag agc ac 96 | 180 |
| 10 | 1531–1623 | 93 | | 34077 | ggg taa cgt ctt ttt ctc ttg c 63 | atg tct ctt ggg cga tag gt 97 | 200 |
| 11 | 1624–1833 | 210 | II S1 | 16894/32236 | att tct tct gaa aga aca gc 64 | gga ggg atc agg gag ttc gc 98 | 310 |
| 12 | 1834–1946 | 113 | II S2, II S3 | 16894 | caa gcc taa cct cct ctc tg 65 | ttc tca ggg gca aga gct g 99 | 200 |
| 13 | 1947–2051 | 105 | II S3, II S4 | 16894 | att tgg agg gag gag ttt gg 66 | tca ctt tcc caa ctt tct gg 100 | 310 |
| 14 | 2052–2191 | 140 | II S4, II S5 | 16894 | cag aaa gtt ggg aaa gta gc 67 | ttg aat tcc tgt gaa gga c 101 | 250 |
| 15 | 2192–2264 | 73 | | 16894 | ctt gga gat gag ata ctg agc 68 | cag gca ctt tca tct gtg ac 102 | 200 |
| 16 | 2265–2382 | 118 | II S6 | 16894 | tcc aca gct gca tct cca ag 69 | acc ctc cct tga gcc cc 103 | 270 |
| 17 | 2383–2450 | 68 | II S6 | 16894 | cag tgg ttg ctt ctt ctg ac 70 | ttg cca gag aaa cat tct cc 104 | 130 |
| 18 | 2451–2557 | 107 | | 16894 | tga aca aag att cca cgt gc 71 | ttc agg agc cag ggt agc atc 105 | 170 |
| 19 | 2558–3367 | 810 | | 16894 | tag caa tgc tct aag tcc tc 72 | tgt ttc ctg agg aag tcc tc 106 | 320 |
| | | | | | cgc agg aga acc gca aca a 73 | gcg atg acg tcg atg ctc 107 | 450 |
| | | | | | gc agc agg gag agc cgc agc 74 | tac cgt cat tct gcg gat tc 108 | 300 |
| 20 | 3368–3831 | 464 | | 16894 | ggt tct ttt tca ttc act tgc 75 | ttt cct ggc agt ctt agc tc 109 | 430 |
| | | | | | gag aat agc ctt atc gtc ac 76 | cag tga tgt gag agc aga 110 | 200 |
| 21 | 3832–3973 | 142 | | 16894/34275 | tgg gaa att gtg gag gga gc 77 | tga ctt ccg cca ctc tgg tg 111 | 250 |
| 22 | 3974–4103 | 130 | III S1 | 16894/34275 | agc ctg tgg tct gag tgg ac 78 | tag gaa ggg gtg tgc tct gtc 112 | 210 |
| 23 | 4104–4163 | 60 | III S2, III S3 | 16894/34275 | atc cac tgc tct ctt gct tt 79 | gtg gtt ctc act tat aat ctg 113 | 170 |
| 24 | 4164–4270 | 107 | III S3 | 34275 | tgg cct cat tgg ctt ccc tgc 80 | aag agg aaa ccc ttg cga ag 114 | 250 |
| 25 | 4271–4370 | 100 | III S4 | 34275 | cta ccc aac ctg acc tct gc 81 | aca tga taa ccc tga cag tc 115 | 220 |
| 26 | 4371–4531 | 161 | III S5 | 34275 | ctc atg ctc tct gtc aac tc 82 | tgg ttc caa tgg gaa tgt gc 116 | 250 |
| 27 | 4532–4669 | 138 | | 34275 | ctg ctt ccc aag cag tct ag 83 | tcc tgg ata gat ttc cag tc 117 | 300 |
| 28 | 4670–4871 | 202 | III S6 | 34275 | agt ttt taa agg aca gat gg 84 | ttt ccc tgc ccc att cct ttg c 118 | 280 |
| 29 | 4872–5036 | 165 | IV S1 | 34275 | ctc tgc cgc tac cac cac tg 85 | ttt atc agg tag agg cag g 119 | 250 |
| 30 | 5037–5147 | 111 | IV S1, IV S2 | 34275 | ttc caa gcc cat agc tgt agc 86 | tga ccc tgc tac tcc tgc ttc 120 | 180 |
| 31 | 5148–5231 | 84 | IV S3 | 15496 | act gtg cct cta aca tgc ac 121 | aag tgc tgg ctc aag cag 138 | 250 |
| 32 | 5232–5348 | 117 | IV S4 | 15496 | tct gtg agt ggt gac agc tc 122 | gtc acc tgt ctt ctc agc 139 | 240 |
| 33 | 5349–5414 | 66 | IV S5 | 15496 | tgg aag gac tct ggc acg tg 123 | gga cag gct ggg aac ctt ag 140 | 250 |
| 34 | 5415–5530 | 116 | | 15496 | aga agc cac tgg agg aat ggc 124 | att atc aga gca ggt ccc ctt c 141 | 250 |
| 35 | 5531–5681 | 151 | IV S6 | 15496 | tcc gag tct ctg att tct cc 125 | aga cgg ccc tca cag tgt c 142 | 210 |
| 36 | 5682–5809 | 128 | IV S6 | 15496 | ttc att ccc tcg gtc tct gc 126 | ctg act gaa cct gtg aga c 143 | 350 |
| 37 | 5810–5906 | 97 | | 15496 | tgt gaa ccc act gcc tgc a 127 | tgg gaa tga ctg cgc ttg c 144 | 200 |
| 38 | 5907–6012 | 106 | | 15496 | atg cct ggg aat gac tgc 128 | tgt cac gcc tgt ctg tgc 145 | 200 |
| 39 | 6013–6120 | 108 | | 15496 | tga cac cca ggc agg cag 129 | tct gtc ctg gtg gat tgg atc 146 | 200 |
| 40 | 6121–6221 | 101 | | 15496 | ttg tgg agc tca ccg tgt 130 | ttc ccg tgg tga cat gca agc 147 | 200 |
| 41 | 6222–6331 | 110 | | 15496 | gtc cac aca ctg ctc tct gc 131 | aca ctc cac ctc cct ggc 148 | 320 |
| 42 | 6332–6470 | 139 | | 15496 | gcc agg gag gtg gag tgt 132 | ggt tcc ttc cac cgc aac 149 | 550 |
| 43 | 6471–6584 | 114 | | 15496/30762 | caa ctc ccc aat ggc tc 133 | cct acc cag tgc aga gtg agg 150 | 350 |
| 44 | 6585–6620 | 36 | | 15496/30762 | tct gtg tgc acc atc cca tg 134 | aag gat tgg gct cca tgg ag 151 | 200 |
| 45 | 6621–6807 | 187 | | 15496/30762 | gtt ggt gct agc tgc tga c 135 | ctt tct tct tcc tta gtg tc 152 | 330 |
| 46 | 6808–7061 | 254 | | 15496/30762 | gtg tgc tgt ctg acc ctc ac 136 | agc ctg ggg tca ctt gca gc 153 | 320 |
| 47 | 7062–UTR | ≥350 | | /30762 | cct tgg ttt caa ttt tcg tgt ag 137 | tgg ggc ctg ggt acc tcc ta 154 | 280 |

Note.
Sizes of exons and PCR products are given in basepairs; domains of protein are indicated according to Stea et al., 1995.
( ) The sequence identification number (SEQ ID NO:) is in parenthesis immediately following each sequence.

TABLE 2

Polymorphisms in coding sequence of the invented gene

| Location | Nucleotide change | | Frequency | Consequence |
|---|---|---|---|---|
| exon 4 | nt 854 | G - A | $Thr_{193}$ | 0.02 | — |
| exon 6 | nt 1151 | A - G | $Glu_{292}$ | 0.07 | — |
| exon 8 | nt 1457 | G - A | $Glu_{394}$ | 0.38 | — |
| exon 11 | nt 1635 | G - A | $Ala_{454}$ | 0.02 | $Ala_{454}$ - Thr (A454T) |
| exon 16 | nt 2369 | G - A | $Thr_{698}$ | 0.12 | — |
| exon 19 | nt 3029 | G - A | $Glu_{918}$ | 0.07 | — |
| exon 23 | nt 4142 | T - C | $Phe_{1289}$ | 0.22 | — |
| exon 46 | nt 6938 | T - C | $His_{2222'}$ | 0.46 | — |
| exon 47 | nt 7213 | $(CAG)_n$ | 3'UTR | # | — |

Note

Frequency as observed in 100 control chromosome: # Seven alleles of $(CAG)_n$ were observed in the range between n = 4 to n = 14, with a heterozygosity value of 0.75.

TABLE 3

Mutations of the invented gene in families with FHM or EA-2

| Disease | Family | Location | Domain | Nucleotide change | | Consequence | |
|---|---|---|---|---|---|---|---|
| FHM | It-II | exon 4 | I S4 | nt 850 | G - A | $Arg_{192}$ - Gln (gain of Sfcl site) | R192Q |
| FHM | US-P | exon 16 | P-segment | nt 2272 | C - T | $Thr_{666}$ - Met | T666M |
| FHM | UK-B | exon 17 | II S6 | nt 2416 | T - C | $Val_{214}$ - Ala (gain of BovI site) | V714A |
| FHM | NL-A/US-C | exon 36 | IV S6 | nt 5706 | A - C | $Ile_{181}$ - Leu (gain of MnII site) | I1811L |
| EA-2 | CAN-191 | exon 22 | III S1 | nt 4073 | deletion C | frameshift (loss of NiaIV site) | $STOP_{1294}$ |
| EA-2 | CAN-26 | intron 24 | space site | nt 4270-1 | G - A | AC/gt - AC/at (loss of BsaAl site) | aberrant splicing |

TABLE 4

Parental transmission of migraine for 36 unrelated Dutch families.

| parents | N | offspring | N | affected N (%) | ratio* |
|---|---|---|---|---|---|
| heathy father x migraine mother | 51 | daughters sons | 72 72 | 48 (66.7%) 21 (29.2%) | 2.3:1 |
| migraine father x healthy mother | 18 | daughters sons | 26 15 | 17 (65.4%) 4 (26.7%) | 2.5:1 |

*ratio of proportion affected sons/proportion affected daughters

What is claimed is:

1. An isolated nucleic acid comprising SEQ ID NO:43.

2. The nucleic acid according to claim 1 comprising a mutation at codon 192 resulting in the replacement of arganine by glutamine.

3. The nucleic acid according to claim 1 comprising a mutation at codon 666 resulting in the replacement of threonine by methionine.

4. The nucleic acid according to claim 1 comprising a mutation at codon 714 resulting in the replacement of valine by alanine.

5. The nucleic acid according to claim 1 comprising a mutation at codon 1811 resulting in a replacement of isoleucine by leucine.

6. The nucleic acid according to claim 1 comprising a G-to-A mutation at codon 193.

7. The nucleic acid according to claim 1 comprising an A-to-G mutation at codon 292.

8. The nucleic acid according to claim 1 comprising a G-to-A mutation at codon 394.

9. The nucleic acid according to claim 1 comprising a G-to-A mutation at codon 454 resulting in a replacement of alanine by threonine.

10. The nucleic acid according to claim 1 comprising a C-to-A mutation at codon 698.

11. The nucleic acid according to claim 1 comprising a G-to-A mutation at codon 918.

12. The nucleic acid according to claim 1 comprising a T-to-C mutation at codon 1289.

13. The nucleic acid according to claim 1 comprising a T-to-C mutation at codon 2221.

14. The nucleic acid according to claim 1 comprising a (CAG)n repeat sequence in its 3'UTR region as indicated in table 2.

15. An isolated nucleic acid comprising a nucleic acid sequence encoding an amino acid sequence depicted in SEQ ID NO:44.

* * * * *

SEQUENCE LISTING

<160> NUMBER OF SEQ ID NOS: 146

<210> SEQ ID NO 1
<211> LENGTH: 953
<212> TYPE: DNA
<213> ORGANISM: human

<400> SEQUENCE: 1

```
tttttttacg ttctcttttt tttcgagtgg tgactggatg ctgattcttc ctcgtatttt      60
tgctgcttct ctctccctcc cctccttccc gggcccgggc ccgccccgca ccctccttcc     120
gcccctcctt ctccggggtc agccaggaag atgtcccgag ctgctatccc cggctcggcc     180
cgggcagccg ccttctgagc ccccgacccg agcgccgagc cgccgcgcga tgggctgggc     240
cgtggagcgt ctccgcagtc gtagctccag ccgccgcgct cccagccccg gcagcctcag     300
catcagcggc ggcggcggcg gcggcggcgt cttccgcatc gttcgccgca gcgtaaccgg     360 agcccttttgc tctttgcaga atgggccgct tcggagacga gatgccggcc cgctacgggg     420
gaggaggctc cggggcagcc gccggggtgg tcgtgggcag cggaggcggg cgaggagccg     480
ggggcagccg gcagggcggg cagcccgggg cgcaaaggat gtacaagcag tcaatggcgc     540
agagagcgcg gaccatggca ctctacaacc ccatccccgt ccgacagaac tgcctcacgg     600
ttaaccggtc tctcttcctc ttcagcgaag acaacgtggt gagaaaatac gccaaaagat     660
caccgaatgg ccatatcctt ttgcccgaac cccagcagca gctgcgcctc cccctcctcc     720
ctccgcctcc cctcttccag gctgggagag agacccgggg gttgatggga ggtggggagg     780 agggggtct tccaggggct gggagagggg gcaccgggag gagtgtgaaa gaatctctcc     840
```

```
acccccgagct gggttgagct accctggagg cttgggaatg ggttttttcgg gggctggggg      900 ccggccagcc ggagagtgga tccttcccaa ggaccgactc tagaatgaga tct              953
```

<210> SEQ ID NO 2
<211> LENGTH: 527
<212> TYPE: DNA
<213> ORGANISM: human

<400> SEQUENCE: 2

```
gatctttycc actggggtca gtgggggtgg gtgcacctcc aacacccttc ttttctttga       60
acaagatttt tccttaattc cccaatactc cctttgaata tatgatttta gccaccatca      120
tagcgaattg catcgtcctc gcactggagc agcatctgcc tgatgatgac aagaccccga      180
tgtctgaacg gctggtgagt gatgtctttt ctcagggtct tctccttggc tttagcagga      240
cattaatttt tgggggagtg gagcagggca cagaggaggc tctcagtcct ggagcccaga      300
gccagatcat gggaagccta aatttccttt tcatttttc ttgaaccaga gtctcgctct       360
gtcacccagg ctggagtgca gtggttcagt catagctcac tgcagcctcc acctcctggg      420
ctcaagccat cctcccactg cagcctcctg agtagcaggg actaacaggt gccaccatgc      480
ccagttaatt ttcttatttt tatctttttt tgtaagaaga tgggat                     527
```

<210> SEQ ID NO 3
<211> LENGTH: 441
<212> TYPE: DNA
<213> ORGANISM: human

<400> SEQUENCE: 3

```
gatcttgtca acatctgccc agcccaagac gctgaccttg ccttctctcc cttccaggat       60
gacacagaac catacttcat tggaattttt tgtttcgagg ctggaattaa aatcattgcc      120
cttgggtttg ccttccacaa aggctcctac ttgaggaatg ctggaatgt catggacttt       180 gtggtggtgc taacgggta agtggcgcgt gctatacgct ttggatttaa ctagctgaag       240
gattacgagg cttttggttg gtgtggtccg ggccaggctc aggaaggctg agcccttgtg      300
ttctccctcc ccttgttatg cgcctgcctc ctttctgcca acaccccacc tccatgtctc      360
agctgtatat tacagcagat gctttctgtt acaattaaaa taatagctca ttattgttgg      420
ctgcttccag agtgctttat g                                                441
```

<210> SEQ ID NO 4
<211> LENGTH: 259
<212> TYPE: DNA
<213> ORGANISM: human

<400> SEQUENCE: 4

```
aaaactgagg ccagtggtgt cgagtcacct gcctgtggtc acccaaccaa tacaggacag       60
cttggaatcc caagcaccc cgccctgctg tctgaccccc aaaacccacc ctctgttctc       120
cattctggct tctttctttc agcatctggg cgacagttgg gacggagttt gacctacgga      180
cgctgagggc agttcgagtg ctgcggccgc tcaagctggt gtctggaatc ccaagtgcgt      240
gagtttccga ccctgacaa                                                   259
```

<210> SEQ ID NO 5
<211> LENGTH: 399
<212> TYPE: DNA
<213> ORGANISM: human

```
<400> SEQUENCE: 5
cttaatattc cctcaggaac acacctgctt tgtctgggag agacctgggc gtcttggtgg      60
cggggttttg gggtacttg ctcatgggct tatgggcct ctctctgtgt cccccaggt       120 ttacaagtcg tcctgaagtc gatcatgaag gcgatgatcc ctttgctgca gatcggcctc     180
ctcctatttt ttgcaatcct tattttgca atcatagggt tagaattta tatgggaaaa      240 tttcatacca cctgctttga agaggggaca gtaggtcca cggagcatga tgcatctttc      300
cagttttctc cttcagggac aagctcttgg gaggattagg cagggtgtg cttctttctc     360 ctggcagctg ggaggaccgt ctccttcaga gagcactac                           399

<210> SEQ ID NO 6
<211> LENGTH: 586
<212> TYPE: DNA
<213> ORGANISM: human

<400> SEQUENCE: 6 tttttttccct tcccttttgt agatgacatt cagggtgagt ctccggctcc atgtgggaca    60
gaagagcccg cccgcacctg ccccaatggg accaaatgtc agccctactg ggaagggccc    120
aacaacggga tcactcagtt cgacaacatc ctgtttgcag tgctgactgt tttccagtgc    180
ataaccatgg aagggtggac tgatctcctc tacaatgtaa gtgatgctgg acagtgtgt    240 gtggacaatc agagtctcag ggaggtggcc tcctgggacc agtgagactc caaggctgca    300
atggagggac cctgagctgg gaaaggcagc ccaaggacaa cacagcccca ctgaagctgg    360
cctgaggctc aggcttttga agattacagg ggctcatgag cagaactcta actatagggc    420
atagaagtct ggagggcccc cagatgcaac atcattttc attgtgcaag tgtttagata    480 taatttttaga ttttttgaata cggaaaggtt atgtgatcca aaatccaaca cagataaaag   540
atagagtaat atctttggac gtaggcgagg ggtccctgcc ctgagg                   586

<210> SEQ ID NO 7
<211> LENGTH: 387
<212> TYPE: DNA
<213> ORGANISM: human

<400> SEQUENCE: 7
tttcttcaga aaacggttcc ttcctccatt tcccctctg ggatgccaga gccccagaac      60
tccacaagcc aagaacattt aagacagagc cacaagagaa ccgagcttcc ccttccctca    120
cctgtcaggt tctatctgag tcccagtcaa ctctcacctg cttcccctcc tcacacccta    180
cagagcaacg atgcctcagg gaacacttgg aactggttgt acttcatccc cctcatcatc    240
atcggctcct tttttatgct gaaccttgtg ctgggtgtgc tgtcagggta agtttctgct    300 actcccacc ccatcccact cactcctctt tgctaacttc tttccaagta gaggccattg    360
aagctttgtt ttcattcact agacaga                                        387

<210> SEQ ID NO 8
<211> LENGTH: 412
<212> TYPE: DNA
<213> ORGANISM: human

<400> SEQUENCE: 8
cccagtcttt tcccagaagt cctgactcct cctgttgaaa actcctgacc tccagggact    60
tctgaatccc caaacacaca cacacacaaa cacacacaca cacacacaca cacacacaca   120
caaacacaca cacaaacgtt tcctaacatt ttcaaaacag ccatactctg gcttttctat   180
```

```
gcttctccag ggagtttgcc aaagaaaggg aacgggtgga gaaccggcgg gcttttctga    240
agctgaggcg gcaacaacag attgaacgtg agctcaatgg gtacatggaa tggatctcaa    300
aagcaggtga ggccctttca tcctggggcc caggatgga gatcccaggc cacagagtac     360
aaagagagtc atgcagtttg gagaaggcta agctgggagg gttatgatgg ga            412

<210> SEQ ID NO 9
<211> LENGTH: 611
<212> TYPE: DNA
<213> ORGANISM: human

<400> SEQUENCE: 9
gagtaggaag ttagaggcag ggtggtcagg gaaggcttct ctaaggaagt accctctgag    60
cagagagacc tgaaggacgt gaagaaggaa gctgtgggga tgtcaaggga aggggcattc    120
caggcagaga cagcaagtgc aaaggccctg agctaggaac gtatttgaga cacagcaagg    180
aagccagtgc agctgaaaca gagtgagagg tggggacagc tggaggagag aagacagga    240 aggtgatgga gatcagatca agcagggct tataggctgt ggtgtggaca ttggttttta    300
ttttgcgcga ggtggggaga atgttggcta ttgctactgt tgcggaggtg gggcttgaag    360
tcacaaacca cccagcagca tgttttttgg tcggttgagc tgtcaccatc agtcagcaga    420 gaatggggt ggccgggcag acccttcttc ctggtccaag ggagaactca tcctccaaat    480
gcaggagctt aactctgtgc tcttcctctt cagaagaggt gatcctcgcc gaggatgaaa    540
ctgacgggga gcagaggcat ccctttgatg gtaactgctc taaacccacc tcaggggtgg    600
gtcccagggg a                                                        611

<210> SEQ ID NO 10
<211> LENGTH: 656
<212> TYPE: DNA
<213> ORGANISM: human
<220> FEATURE:
<221> NAME/KEY: Unsure
<222> LOCATION: (638)..(638)
<223> OTHER INFORMATION: n = g, a, c, t or u
<220> FEATURE:
<221> NAME/KEY: misc_feature
<222> LOCATION: (638)..(638)
<223> OTHER INFORMATION: n is a, c, g, t or u

<400> SEQUENCE: 10
ttaatccaag acacactgtg tgtcctatat ggtctgtgtt cgaaaaaggg taacgtcttt    60
ttctcttgcc atgtttccat tgttaggagc tctgcggaga accaccataa agaaaagcaa    120
gacagatttg ctcaacccccg aagaggctga ggatcagctg gctgatatag cctctgtggg    180
tgagtccctt cctctgccac ctatcagttg ttcatcacct atcgcccaag agacatggtg    240 gggtggggc agagggcttg caaaccgtgc tgcctggatt tgggtctcag ctccacccttt   300 tcccacctgt gcgtgtgtcc tgggcagatt acatcattat gggaataaca tccgtgccta    360
gcttctcatt attttgtggg aattcaacta aatgatcccc atgaagcatg gcaaaccagc    420
acctggcagg gacgaagctc ccagtcaagt tggtgaatgt ttgtgactca ttcgggaagt    480
atcatggggg acctgcttat attaggtgct tggttgcaaa caacaaggc agtcacgagg    540 ctgagctggg aggatcactt gagcctggga agtggaggct gcaataagcc attattgtgt    600
tactgcactc cagcctggca cagaaaaaaa aaaaaaanac aaactgagcc agcaca       656

<210> SEQ ID NO 11
```

<211> LENGTH: 778
<212> TYPE: DNA
<213> ORGANISM: human

<400> SEQUENCE: 11

```
gatcacttct aaagttaaat gtccatggga aaacagtctc atccacatct ctttctggag        60
gccttccaag cgtgctccat gcagctctgt tgcctgcccc tgcatcaggg aatggaggct       120
ctgctttatc ctgccctgtg gtgtgactcc cagaggcatc agatgtggct gggagtggga       180
gacatggaaa attggctcct gcaacagaga actatcagcc ttcccatcaa ttggttactt       240
ctaattctgt tattttcag gggcactgtc ttctcataag ctccatctat gcaaaactaa        300
gcccatgggt catgatggtt ccctcaggcc agaggcttgc tggagagact aatggatccc       360
ctggctaaaa tctgtgcttg gctgcacat tggttaattt cttctgaagg aacagcctga        420
gcctgacatt ctccatcttt tccctggcag gttctccctt cgcccgagcc agcattaaaa       480
gtgccaagct ggagaactcg acctttttc acaaaaagga gaggaggatg cgtttctaca        540
tccgccgcat ggtcaaaact caggccttct actggactgt actcagtttg gtagctctca       600
acacgctgtg tgttgctatt gttcactaca accagcccga gtggctctcc gacttccttt       660
gtgagtatca cccagcccca ccctgccaa ctccctgatc cctccctcac accttttc          720
cacttctctt tctctggtag tatgtgtatc ttctttggtc ctcattgaat ctgcccctt        778
```

<210> SEQ ID NO 12
<211> LENGTH: 626
<212> TYPE: DNA
<213> ORGANISM: human
<220> FEATURE:
<221> NAME/KEY: Unsure
<222> LOCATION: (27)..(27)
<223> OTHER INFORMATION: n = g, a, c, t or u
<220> FEATURE:
<221> NAME/KEY: misc_feature
<222> LOCATION: (27)..(27)
<223> OTHER INFORMATION: n is a, c, g, t or u

<400> SEQUENCE: 12

```
gatcacttgt ggccaggagt tcaagancag ccagggcaac atagtgagga ccccccatctc       60
cacattaaaa attttaaaaa gaaaaaagat aagtcagaag ttgggtgtgg tgacacatgc       120
ctgtagttct agcatgttgg aggccaaatc agggaaactg tttgaggcca ggagtttgaa       180
accagcctaa cagcatagca agacctcatc tctacaaaaa ataaaaagtt taaaaatgat       240
aataaaagga aagtcagagc cacctggaac ccctaccctc agcaagccta acctcctctc       300
tgtttcctcc ttctcccttc tagactatgc agaattcatt ttcttaggac tctttatgtc       360
cgaaatgttt ataaaaatgt acgggcttgg gacgcggcct tacttccact cttccttcaa       420
ctgctttgac tgtggggtaa gtgctcttgt ttctaagagt tcatttctcc agctcttgcc       480
tggaatgaca gatacctgga cacattaaag ggagaaaggt aaagtcaccc ctgaatatga       540
gagactcaga tggatgcaga aggaatgaga aaacaatcca aacactggca aggatacagt       600
gtacccagaa ccctcaacca ccgcca                                            626
```

<210> SEQ ID NO 13
<211> LENGTH: 976
<212> TYPE: DNA
<213> ORGANISM: human
<220> FEATURE:
<221> NAME/KEY: Unsure
<222> LOCATION: (5)..(7)
<223> OTHER INFORMATION: n = g, a, c, t or u

```
<220> FEATURE:
<221> NAME/KEY: misc_feature
<222> LOCATION: (5)..(5)
<223> OTHER INFORMATION: n is a, c, g, t or u
<220> FEATURE:
<221> NAME/KEY: misc_feature
<222> LOCATION: (7)..(7)
<223> OTHER INFORMATION: n is a, c, g, t or u

<400> SEQUENCE: 13
gatcngncat gcacaccagc ctgggtgata agagcaagac tcctctcaaa ataaatgaat    60
aaataaaaat aaataaataa ataagaggcc gggtgcagtg gctcaatgct ttggaaagtg   120
gaggccaaca gttggagaga ccaaagcagg aggatggctt cagcccagaa gtttgaggcc   180
mgcctgggca atactagcga gacactatct ctataaaaat gttttaaaat tagccagatg   240
tggtggggca cacctgtaat cccagctact caagaggctg aggtgggagg atcacttaag   300
cccaggagga cagtgctgca gtgagctatg attgcgccca ctgcactcca gcctgggtga   360
cacagtgaga cccggtctct atagataaat gaatggatga atgaggggt caaggatcct    420
cacccggctt ccatttggag ggaggagttt ggttgagttc ttgcaaggtt ggtacctagg   480
aaatgcttgc cagttctgga gcccagacac tgtccctgga catgagacca ggttctctgc   540
cctaggttat cattgggagc atcttcgagg tcatctgggc tgtcataaaa cctggcacat   600
cctttggaat cagcgtgtta cgagccctca ggttattgcg tattttcaaa ctcacaaagt   660
aagtctttgg ggttcctgga catttgtaca ggggtgggg atgggggaca tggtggggcc    720
gcctccagaa agttgggaaa gtgagcctcg tgtttcgagg gctgactccg gggcctgcct   780
wccccgcctg gcctgagtcc tcgcctggsc tctgtcggca ggtactgggc atctctcaga   840
aacctggtcg tctctctcct caactccatg aagtccatca tcagcctgtt gtttctcctt   900
ttcctgttca ttgtcgtctt cgcccttttg ggaatgcaac tcttcggcgg ccagtaagtc   960
cttcacagga attcaa                                                   976

<210> SEQ ID NO 14
<211> LENGTH: 1110
<212> TYPE: DNA
<213> ORGANISM: human
<220> FEATURE:
<221> NAME/KEY: Unsure
<222> LOCATION: (620)..(620)
<223> OTHER INFORMATION: n = g, a, c, t or u
<220> FEATURE:
<221> NAME/KEY: misc_feature
<222> LOCATION: (620)..(620)
<223> OTHER INFORMATION: n is a, c, g, t or u

<400> SEQUENCE: 14
ccctccacgt gcaggctgcc ttcctcgtag cccagacacc catttgcggt cacccaaatg    60
ggcagggccc tggtaccac tcagggtttc ctggggacag agatgatgga acgttcgtt    120
tccttggaga tgagatactg agccacaccc tcagagcacc ccgggtgggg ccaacgtgaa   180
atgtctgtgt cctcccctgca ggtttaattt cgatgaaggg actcctccca ccaacttcga   240
tacttttcca gcagcaataa tgacggtgtt tcaggtacag cctccacctg gccccacggg   300
ccaacacctc tcagtgtcac agatgaaagt gcctgctcca catccaaggg gcttccctga   360
actcctcctt ctctacctgg ccttttcaca ccactttgaa acacagattt tatggttatc   420
attattcaat tatggtgagg ccaacagatc aggagatgaa tgtcattgga aagatagttt   480
gtggctgggc acggtggctc acacccataa tcccagcact ttggccaggt acggtggctc   540
```

```
acacctgtaa tcccaacgct ttgggaagcc caggtgggcg gatcacttga gatcaggaat      600
tcgagaccag cctggccaan atggtgaaac cccatctcta ctaaaaatac aaaaattagc      660
cgggcgtggt agcacatgcc tgtaatccca gctactcggg agatgaggca caagaattgc      720
ttgaacctgg gaggcagagg ttgcagtgag ccaagatcgc gccactgcac tcmagcctgg      780
gcaacagagt gagactccat ctcaaaaaag caaaagaaaa aaaaaaccac tttgggaggt      840
caagatggga ggactacttg aggccaggag tttgagacaa gtctgggcaa catagtgaga      900
ctccgtctct gcaaaaaaat wataataata attagctggg catggtgata catacctcct      960
agctactagg gcagctgaag tggaaggatt gcttaagccc aggaggttga ggctgcagta     1020
agctacaatc acaccactat actccagcct gggcgagaga gcaaagccct gtctcaaaaa     1080
cgaaaagaaa gtttgttata ctcacagatc                                      1110
```

<210> SEQ ID NO 15
<211> LENGTH: 982
<212> TYPE: DNA
<213> ORGANISM: human

<400> SEQUENCE: 15

```
gatcctccca ccttggcctc ccaaagtgct gggattacag gcatgagcca tggcatgcgg       60
tctcttcctg ttcttataag ggcactaata ccatcatgaa gtcccccatg acctcatcta      120
accctagtta cctcttaaag gccccatctc caaataccat cccatcatag gttagggctt      180
caactcatga atttggaggc gggcacaatt tagtccataa caaatcccct taatcacatc      240
aagtaagaca gagttacagg agggtctgtg actcctccag ggtcccattt tcctagaagc      300
caggctaaga gccccacgac gcaggaacgg ccctttctac tcgcaaacaa agagaaaagc      360
caaggagaag ccaacacgga gtctggctct gcaaaccggg caggattgtt aaagacctcc      420
tgggctcggg gatggggtgg gcggattccg gctccacagc tgcatctcca aggggcccgt      480
ggctgagagg ggggttggct gtgtgtttct tcctcccctt tcagatcctg acgggcgaag      540
actggaacga ggtcatgtac gacgggatca agtctcaggg gggcgtgcag gcggcatgg       600 tgttctccat ctatttcatt gtactgacgc tctttgggaa ctgtatcctt catggagaga      660
gagaagggga caggcctgga cctctggcag aggagaggtt gcaggggctc aagggagggt      720
actgagagac ccagataccc agggcccaag tggtgtccca ccagtggttg cttttcctga      780
ctcagacatt tgcagacacc ctcctgaatg tgttcttggc catcgctgtg acaatctgg       840 ccaacgccca ggagctcacc aaggtggagg cggtgggaga atgtttctct ggcaaagtta      900
ccacctgccc atggcagatc aagcacttt ttggattaac tgagccacag gaaataacat       960
tttcaaatag atkaaaaaga tc                                               982
```

<210> SEQ ID NO 16
<211> LENGTH: 314
<212> TYPE: DNA
<213> ORGANISM: human

<400> SEQUENCE: 16

```
ccttggttct gattggtcga aatatttcaa atgttgcccc tggtcagcaa cagggtcaga       60
agtgagtccc caaggcctag ttcatgtttt gtgaacaaag attccacgtg ccttttcagg      120
acgagcaaga ggaagaagaa gcagcgaacc agaaacttgc cctacagaaa gccaaggagg      180
tggcagaagt gagtcctctg tccgcggcca acatgtctat agctgtgtaa gtcccctaat      240
ccctgggatg ctaccctggc tcctgaacgt gtccgaccac tatccaggca cagatttggg      300
```

```
aagcagtggg ggtg                                                    314

<210> SEQ ID NO 17
<211> LENGTH: 1113
<212> TYPE: DNA
<213> ORGANISM: human

<400> SEQUENCE: 17
gcccctagcc aggtgggagc catggagggt tcttgagcag aggaggctgg gacctgactc    60
agatgctcac agactcctag cattcaggtg gggagtagag ggtggagagc aggagtggga   120
ggctgagatg tgggttggtt cgcctgggtc atccatccaa gctacagtgc ctagcaatgc   180
tctaagctcc tgtgaccatg ccactgcagg aaagagcaac agaagaatca aaagccagcc   240
aagtccgtgt gggagcagcg gaccagtgag atgcgaaagc agaacttgct ggccagccgg   300
gaggccctgt ataacgaaat ggacccggac gagcgctgga aggctgccta cacgcggcac   360
ctgcggccag acatgaagac gcacttggac cggccgctgg tggtggaccc gcaggagaac   420
cgcaacaaca acaccaacaa gagccgggcg gccgagccca ccgtggacca gcgcctcggc   480
cagcagcgcg ccgaggactt cctcaggaaa caggcccgct accacgatcg ggcccgggac   540
cccagcggct cggcgggcct ggacgcacgg aggccctggg cgggaagcca ggaggccgag   600
ctgagccggg aggaccccta cggccgcgag tcggaccacc acgcccggga gggcagcctg   660
gagcaacccg ggttctggga gggcgaggcc gagcgaggca aggccgggga ccccaccgg    720 aggcacgtgc accggcaggg gggcagcagg gagagccgca gcgggtcccc gcgcacgggc   780
gcggacgggg agcatcgacg tcatcgcgcg caccgcaggc ccggggagga gggtccggag   840
gacaaggcga gcggagggc gcggcaccgc gagggcagcc ggccgcccg gggcggcgag    900 ggcgagggcg agggtcccga cggggcgag cgcaggagaa ggcaccggca tggcgctcca   960
gccacgtacg aggggacgc gcggaggag gacaaggagc ggaggcatcg gaggaggaag   1020
taagtggagg tgacctcgaa tccgcagaat gacggtaaca ttaataatac aacagccaaa  1080
gtagcacgtg ctgtgtattt gttataaaat ata                              1113

<210> SEQ ID NO 18
<211> LENGTH: 590
<212> TYPE: DNA
<213> ORGANISM: human

<400> SEQUENCE: 18
gtcctgaaac tttgcctttt aatcctaaat cattgttggt tctttttcat tcacttgcct    60
tcctcagaga gaaccagggc tccgggtcc ctgtgtcggg ccccaacctg tcaaccaccc   120
ggccaatcca gcaggacctg ggccgccaag acccacccct ggcagaggat attgacaaca   180
tgaagaacaa caagctggcc accgcggagt cggccgctcc ccacggcagc cttggccacg   240
ccggcctgcc ccagagccca gccaagatgg gaaacagcac cgaccccggc ccatgctgg    300 ccatccctgc catggccacc aaccccagaa cgccgccag ccgccggacg cccaacaacc   360
cggggaaccc atccaatccc ggcccccca agaccccga gaatagcctt atcgtcacca   420
accccagcgg cacccagacc aattcagcta agactgccag gaaacccgac acaccacag    480 tggacatccc cccagcctgc ccacccccc tcaaccacac cgtcgtacaa ggtgagaccc   540
tctgctctca catcactggg caggggacct ggcgtcctgg agccagaggt             590

<210> SEQ ID NO 19
```

```
<211> LENGTH: 340
<212> TYPE: DNA
<213> ORGANISM: human
<220> FEATURE:
<221> NAME/KEY: Unsure
<222> LOCATION: (1)..(340)
<223> OTHER INFORMATION: n = g, a, c, t or u
<220> FEATURE:
<221> NAME/KEY: misc_feature
<222> LOCATION: (278)..(297)
<223> OTHER INFORMATION: n is a, c, g, t or u

<400> SEQUENCE: 19
ggagtacacc gaggagttcc cagagacttg tgggaaattg tggagggagc cctgtgttgg      60
ttcttgtccc aacagtgaac aaaaacgcca acccagaccc actgccaaaa aagaggaag     120
agaagaagga ggaggaggaa gaagacgacc gtggggaaga cggccctaag ccaatgcctc    180
cctatagctc catgttcatc ctgtccacga ccaacccgtg agtatggccc ccgagcagag    240
ggcaggggg gctgggtctc ccaccagggt ggcggaannn nnnnnnnnnn nnnnnnnctc     300
ccaccaggt ggcggaagtc aggccagatt agagggcaat                           340

<210> SEQ ID NO 20
<211> LENGTH: 477
<212> TYPE: DNA
<213> ORGANISM: human

<400> SEQUENCE: 20
gatctcagta gtggtaggta acatgagatt atggaagaaa agggtttgtg agcctgtggt      60
ctgagtggac ctctgcacgc ccatctgtct ccaacagcct tcgccgcctg tgccattaca    120
tcctgaacct gcgctacttt gagatgtgca tcctcatggt cattgccatg agcagcatcg    180
ccctggccgc cgaggaccct gtgcagccca acgcacctcg gaacaacgtg agtcccacag    240
agcacacccc ttcctagcct ggctgctctg cctcaggcca cttctcctg catccaaaat     300
gctcataggt agggtgggat gttggggtca ccctaggca tagcccttat ggctgctggt     360
tgagagggga agctctgatt ccttgggggat gctcttggga gcaagacatt ccttgaggca    420
gtttctctgt gagcctggtg gggtggaggt ggcccagagt gactggggct gaaaatt        477

<210> SEQ ID NO 21
<211> LENGTH: 168
<212> TYPE: DNA
<213> ORGANISM: human

<400> SEQUENCE: 21
gatccactgc tctcttgctt ttatccctta caggtgctgc gatactttga ctacgttttt      60
acaggcgtct ttacctttga gatggtgatc aaggtgagtg cagattataa gtgagaacac    120
acggtaattt tttttttttaa gcaagtgcag ggctgggcac agtggatc                 168

<210> SEQ ID NO 22
<211> LENGTH: 368
<212> TYPE: DNA
<213> ORGANISM: human

<400> SEQUENCE: 22
gatctaagag ccggcaagcc agagctggct tccatcaggc aaaggggggc cgcctcatgg      60
ggcagggggct ccccactcct ccctgggagt cctctggcca ctgcccatcc ctgcaagatg    120
aggtggcctc attggcttcc ctgcctctcc ccgagaggct agagagtggg tggcagcacc    180
ccagggtggg gatcaggtgg gggttctgag caccctctct tctcccccac agatgattga    240
```

```
cctggggctc gtcctgcatc agggtgccta cttccgtgac ctctggaata ttctcgactt      300
catagtggtc agtggggccc tggtagcctt tgccttcacg taagtctctt cgcaagggtt      360
tcctcttg                                                                368
```

<210> SEQ ID NO 23
<211> LENGTH: 515
<212> TYPE: DNA
<213> ORGANISM: human

<400> SEQUENCE: 23

```
gatcttaacc ccaagacact tcatctaaag gaaaaactgc cataatacac agattatttt      60
aggtcagctc actttactgc catctgctgg gaagttgtaa taatacaaat atccatacac      120
gatggctagg atgttatcag cacctccttt aatgtgttgt ccttgagcag tgtacaacct     180
gctcagctgt acatgataac cctgacagtc ccccccaccg caccccacca tctcccaatc     240
tcaccttgag ctttggcagc cgcttgatgg ttttaagagg tcgtagcacc cggaggactc     300
ggagggattt aatcgtgttg atgtcttttc ctttgctatt gccactgtgg aggaatgttt      360
aggtgggaag aagggaagag aggaagcaga ggtcaggttg ggtaggggc agcccacagc      420 tccatgggac cctacccttc ccaggcctag aagtctgggg tgagcttggc acaagcctgc     480
cctttcctgg tgaagagtgg tccattttac cctgt                                 515
```

<210> SEQ ID NO 24
<211> LENGTH: 406
<212> TYPE: DNA
<213> ORGANISM: human

<400> SEQUENCE: 24

```
ggccactgga ggcagaaggt tggcaggtcc ccagcccctc atgctctctg tcaactccac      60
cccacaggct gtgtttgact gtgtggtgaa ctcacttaaa aacgtcttca acatcctcat     120
cgtctacatg ctattcatgt tcatcttcgc cgtggtggct gtgcagctct tcaaggggaa      180
attcttccac tgcactgacg agtccaaaga gtttgagaaa gattgtcggt gggtctccgc     240
tttccagcac attcccattg gaaccagcag gtgggcaggg gggaagtggc tagaggcatt      300
ggccacttgg gctcagagac tggagaagtg atgagccttg gaagtgactc agttgcaacc      360
agcttggatc aagggtagaa agaaaaccgg ttttagaatt tgagtc                     406
```

<210> SEQ ID NO 25
<211> LENGTH: 516
<212> TYPE: DNA
<213> ORGANISM: human
<220> FEATURE:
<221> NAME/KEY: Unsure
<222> LOCATION: (421)..(516)
<223> OTHER INFORMATION: n = g, a, c, t or u
<220> FEATURE:
<221> NAME/KEY: misc_feature
<222> LOCATION: (421)..(421)
<223> OTHER INFORMATION: n is a, c, g, t or u
<220> FEATURE:
<221> NAME/KEY: misc_feature
<222> LOCATION: (490)..(490)
<223> OTHER INFORMATION: n is a, c, g, t or u
<220> FEATURE:
<221> NAME/KEY: misc_feature
<222> LOCATION: (509)..(509)
<223> OTHER INFORMATION: n is a, c, g, t or u

<400> SEQUENCE: 25

-continued

```
gatctcaaac tcctggcctc aagtgataca tctgccttgg cctcctaaag tgttgggatt    60
acaggcgtga gcaccatgcc cggcctccaa gacctttctt attgctaagc tctcaggccc   120
tttatcctcc tgctcccag ggctcctcct ggatagattt ccagtcgggc cacttactgt    180
ggccagcctt ctcccgtgga cacggtgaag agggtcagca gagcccacag cacattgtcg   240
taatggaatt catacttctt ccactcccgg tctcgcgcct tcacctcatt cttctcgtag   300
aggaggtatt tgcctctgcc acagagagtg gggactgtta gtaaatggga aagagggct    360 gtcttgcact tgtctttggt tatcagagac aggggaggg aaaggaagag tggtccacca    420
ncctagactg cttgggaagc agtgacttcc catcctgcca ccatgtgttc ctgtgcttca   480 tagggggatgn cgtgtgcaat ctacttttna ggataa                             516
```

<210> SEQ ID NO 26
<211> LENGTH: 489
<212> TYPE: DNA
<213> ORGANISM: human

<400> SEQUENCE: 26

```
accttcctca tcacccttgg gtccctgtct ctctccttcc tgccccttcc ctctccctgc    60
cccattcctt gcagggtcct caagcattcg gtggacgcca cctttgagaa ccagggcccc   120
agccccgggt accgcatgga gatgtccatt ttctacgtcg tctactttgt ggtgttcccc   180
ttcttctttg tcaatatctt tgtggccttg atcatcatca ccttccagga gcaaggggac   240
aagatgatgg aggaatacag cctggagaaa aatgaggtgc cacttccaat tccatctgtc   300 cttaaaaac tggggacaca cacaaacttt aaaacacaca caacacccag gaaccccttt    360
ctaggggtac ctgggggagg gaacagaagc attgtcccaa ccgaatccag tcttcagggc   420
agcccttcat ggagtttcag aggaaacaca tcatatagtg tatgtatcag tcagtttaga   480
ctaggttat                                                            489
```

<210> SEQ ID NO 27
<211> LENGTH: 512
<212> TYPE: DNA
<213> ORGANISM: human
<220> FEATURE:
<221> NAME/KEY: Unsure
<222> LOCATION: (1)..(512)
<223> OTHER INFORMATION: n = g, a, c, t or u
<220> FEATURE:
<221> NAME/KEY: misc_feature
<222> LOCATION: (13)..(13)
<223> OTHER INFORMATION: n is a, c, g, t or u
<220> FEATURE:
<221> NAME/KEY: misc_feature
<222> LOCATION: (26)..(26)
<223> OTHER INFORMATION: n is a, c, g, t or u
<220> FEATURE:
<221> NAME/KEY: misc_feature
<222> LOCATION: (48)..(48)
<223> OTHER INFORMATION: n is a, c, g, t or u
<220> FEATURE:
<221> NAME/KEY: misc_feature
<222> LOCATION: (69)..(69)
<223> OTHER INFORMATION: n is a, c, g, t or u
<220> FEATURE:
<221> NAME/KEY: misc_feature
<222> LOCATION: (103)..(103)
<223> OTHER INFORMATION: n is a, c, g, t or u
<220> FEATURE:
<221> NAME/KEY: misc_feature
<222> LOCATION: (109)..(109)
<223> OTHER INFORMATION: n is a, c, g, t or u
<220> FEATURE:
<221> NAME/KEY: misc_feature
<220> FEATURE:
<221> NAME/KEY: misc_feature
<222> LOCATION: (134)..(134)
<223> OTHER INFORMATION: n is a, c, g, t or u
<220> FEATURE:
<221> NAME/KEY: misc_feature
<222> LOCATION: (136)..(136)
<223> OTHER INFORMATION: n is a, c, g, t or u
<220> FEATURE:
<221> NAME/KEY: misc_feature
<222> LOCATION: (449)..(449)
<223> OTHER INFORMATION: n is a, c, g, t or u

<400> SEQUENCE: 27

```
tagcccatgc aanaatgggg aaatgncagt gcaagttttg gcagttgntg acatctcaag      60
caactgtanc tgttgggata agaaagcaat ggtgagaagg aanagaganc ccaggaatcc     120
tggctggggg caananaggc agagactcaa gcagaagcac ttgagaaccg cgacgagtta     180
gacagagggt gcccggtgta cagccacctt cctcctgcct ctgccgctct caccactggc     240
ctctctcccg cagagggcct gcattgattt cgccatcagt gccaagccgc tgacccgaca     300
catgccgcag aacaagcaga gcttccagta ccgcatgtgg cagttcgtgg tgtctccgcc     360
tttcgagtac acgatcatgg ccatgatcgc cctcaacacc atcgtgctta tgatgaaggt     420
aagtgcccca caccagcccc cagcactant taaccccccac ctcgttcctg cctctaccct     480
gataaaatga aaccatttgc agatttccca ga                                   512
```

<210> SEQ ID NO 28
<211> LENGTH: 411
<212> TYPE: DNA
<213> ORGANISM: human
<220> FEATURE:
<221> NAME/KEY: Unsure
<222> LOCATION: (306)..(309)
<223> OTHER INFORMATION: n = g, a, c, t or u
<220> FEATURE:
<221> NAME/KEY: misc_feature
<222> LOCATION: (306)..(306)
<223> OTHER INFORMATION: n is a, c, g, t or u
<220> FEATURE:
<221> NAME/KEY: misc_feature
<222> LOCATION: (309)..(309)
<223> OTHER INFORMATION: n is a, c, g, t or u

<400> SEQUENCE: 28

```
gggtctttcc tgaactgtgc ctcctaccag tgaggttgct cagaccttgc ctggggctgg      60
agtgttgcct ggagaacagc catgaagctg acctccccac ttcccacttc ccacccctgc     120
tcgctgaccc ctgctactcc tgcttctttc ccctagttct atggggcttc tgtggcttat     180
gaaaatgccc tgcgggtgtt caacatcgcc ttcacctccc tcttctctct ggaatgtgtg     240
ctgaaagcca tggcttttgg gattctggta agtaccacct tggggctaca gctatgggct     300
tggaanaanc ccaaggggga acaatgggtc ctggatgatg gtctcccaac gtggccccaa     360 gaacccaac ctcaagggtg gcttcagtat cctgcccagt ggccacagat c               411
```

<210> SEQ ID NO 29
<211> LENGTH: 420
<212> TYPE: DNA
<213> ORGANISM: human

<400> SEQUENCE: 29

```
ctgtcccggg cactccgctg atgggcaact gtgcctctaa catgcaccgg ccagcctagg      60
gggccgggaa ccaagccctc tgttggcatc tctgtcttgt gggtccccat tctagaatta     120
tttccgcgat gcctggaaca tcttcgactt tgtgactgtt ctgggcagca tcaccgatat     180
```

```
cctcgtgact gagtttgggg taagtctccc tccagcttct ctctgggtga ctctgggctg    240
gacgaggcag gcggcagggg gcggggggagc ggtcccagag gcagtgtgtc ccggaagcca    300
tagctgcttg agccagcact tggccatgac cagagaggga gaactgggc cccgggggaca    360 agggcagccc ctcaggaggg cattgtgggg agatgggggt aacaaagctt ggctgtaggg    420

<210> SEQ ID NO 30
<211> LENGTH: 342
<212> TYPE: DNA
<213> ORGANISM: human

<400> SEQUENCE: 30
ttaatagtgc tttctctctc cctccttatt tggggtctgg cttgcttttt tcctgttggt     60
tggcttcatg taggggcctc tgtgagtggt gacagtctg agcctttggg gtgggtggat    120
ggtcacccct cttcctccat ctccccagaa taacttcatc aacctgagct ttctccgcct    180
cttccgagct gcccggctca tcaaacttct ccgtcaggt tacaccatcc gcattcttct    240
ctggaccttt gtgcagtcct tcaaggtgag tcctcgtccc tgctgctggc ccagggcctg    300
agaagacagg tgaccctcat gctctggctg aatgtagaag tc                      342

<210> SEQ ID NO 31
<211> LENGTH: 559
<212> TYPE: DNA
<213> ORGANISM: human
<220> FEATURE:
<221> NAME/KEY: Unsure
<222> LOCATION: (536)..(536)
<223> OTHER INFORMATION: n = g, a, c, t or u
<220> FEATURE:
<221> NAME/KEY: misc_feature
<222> LOCATION: (536)..(536)
<223> OTHER INFORMATION: n is a, c, g, t or u

<400> SEQUENCE: 31
cccccaagaa gaatgcccac caagccctgg aaggactctg gcacgtggca tatggccacc     60
caacccagtg gggcagagca ctgggacaag ggaggaagac tgcagtgcgg ctgagggacc    120
cccagcactc ttcttcattg cctttttttcc caccaggccc tgcctttatgt ctgtctgctg    180 atcgccatgc tcttcttcat ctatgccatc attgggatgc aggtgagtgt cgtgtcccta    240
aggttcccag agcctcccaa ggagggcagc caccccttaga aaggggtggg tcagaggagc    300
ctggttcaca gaagcagcca tggaggttga gctgggtttc ccagaagcca ctggaggaat    360
ggcagcccct ggtcgtcacc cwmcaattcc acaggtgttt ggtaacattg gcatcgacgt    420
ggaggacgag gacagtgatg aagatgagtt ccaaatcact gagcacaata acttccggac    480
cttcttccag gccctcatgc tctcttccgg tcagaagggg acctgctctg ataatnctgt    540
ttccgtgggg tggggtgcc                                                 559

<210> SEQ ID NO 32
<211> LENGTH: 316
<212> TYPE: DNA
<213> ORGANISM: human

<400> SEQUENCE: 32
tcagagccat gctcactgtg tgctccactc ctgaggaggc gttggtacca gtcagggctg     60
ggtgtccgag tctctgattt ctccctgtcc tcaggagtgc caccggggaa gcttggcaca    120
acatcatgct ttcctgcctc agcgggaaac cgtgtgataa gaactctggc atcctgactc    180
gagagtgtgg caatgaattt gcttattttt actttgtttc cttcatcttc ctctgctcgt    240
```

```
ttctggtgag tctgtggaca ctgtgagggc cgtctgggct ccctaagcct ggcttccttt    300
cagggagtgg ttctgt                                                   316
```

<210> SEQ ID NO 33
<211> LENGTH: 694
<212> TYPE: DNA
<213> ORGANISM: human
<220> FEATURE:
<221> NAME/KEY: Unsure
<222> LOCATION: (413)..(413)
<223> OTHER INFORMATION: n = g, a, c, t or u
<220> FEATURE:
<221> NAME/KEY: misc_feature
<222> LOCATION: (413)..(413)
<223> OTHER INFORMATION: n is a, c, g, t or u

<400> SEQUENCE: 33

```
gtgtagtgag aactcacctc tccattcccc agtctctttc tgtctctgtc tcatttcctt    60
tccccatctt ctctctatcc ctctctccat ctggggcctc tgtgtctgtc tttgggtctg   120
tctgtccgtc tgactgtctg tatccttctc acttcactca ttcattccct cggtctctgc   180
cccattctct cttggtcccg ggtccccaca gatgctgaat ctctttgtcg ccgtcatcat   240
ggacaacttt gagtacctca cccgagactc ctccatcctg gcccccacc acctggatga    300 gtacgtgcgt gtctgggccg agtatgaccc cgcagcttgg taagaagtca ccccgaatcc   360
tccagccaca atactcacct ctccctggaa ctggaacacg ggctaggcta ggncccaga    420 ctctggagca ctgaactcct ggggctccta gcagggtct cacaggttca gtcaggagag    480
aagatataag aatcatcacc cttgcatacc ccagattaaa cacgtagggt gccaacctgc   540
ccaaaccctg gaggactttc tgggaaatga ggagggcgtc aaccatgaga tgtctgaaga   600
gccctctcct cctacgagtc tctcctgtct ctcactgtga agtctccaga tggtgaggat   660
cgattagcca ggctccagga gaaaccaaca gact                               694
```

<210> SEQ ID NO 34
<211> LENGTH: 474
<212> TYPE: DNA
<213> ORGANISM: human

<400> SEQUENCE: 34

```
aagggaggtg cctgcagtcc cgaactcgac tgacatccta cacccctggg tctccccagt    60
gtctgggaat gtactgggaa ttcacttgtc cccagtctct cccactcctt gaagccaggg   120 acacccagc ctcgggcatc atgacctcgt tgtgtgccca gggagcccgt gtgaacccat    180
tgcctgcact aaccccttt cttctccttt cagcggtcgg attcattata aggatatgta    240
cagtttatta cgagtaatat ctccccctct cggcttaggc aagaaatgtc ctcataggg    300 tgcttgcaag gtttgacttc cactaaaacc tgctagcatc catggaatga gtgtggcttg   360
gggttcttca atatatatat ttcatatata tatatatata tatctctctc tctctaaaaa   420
aacagagcca tctctctttc ttgcattaaa ctagaaaact ctcttagcca acag          474
```

<210> SEQ ID NO 35
<211> LENGTH: 413
<212> TYPE: DNA
<213> ORGANISM: human
<220> FEATURE:
<221> NAME/KEY: Unsure
<222> LOCATION: (323)..(413)
<223> OTHER INFORMATION: n = g, a, c, t or u
<220> FEATURE:

<221> NAME/KEY: misc_feature
<222> LOCATION: (323)..(324)
<223> OTHER INFORMATION: n is a, c, g, t or u
<220> FEATURE:
<221> NAME/KEY: misc_feature
<222> LOCATION: (332)..(334)
<223> OTHER INFORMATION: n is a, c, g, t or u
<220> FEATURE:
<221> NAME/KEY: misc_feature
<222> LOCATION: (339)..(341)
<223> OTHER INFORMATION: n is a, c, g, t or u

<400> SEQUENCE: 35

```
cctgggtagg ggcgggcgcg gctcacggga gacccaggag ggatgcctgg gaatgactgc      60
gcttgccttg ggttttctgt agcggcttct gcggatggac ctgcccgtcg cagatgacaa     120
caccgtccac ttcaattcca ccctcatggc tctgatccgc acagccctgg acatcaagat     180
tgccaagggt aaggaaggga caggggcggg cacagacagg cgtgacaggg tggaactggg     240
gatctcctcc ctaccccaaa ctagaggatc tgctgtcacc acccggatct tcattcactc     300
ttccattcat tcgttccaca ggnnttttg gnnnttggnn ntttgtgtt tttttttttt     360
ttttgagaca gagtcttgct ctgttgccca ggcagcagtg cggtgacatg atc            413
```

<210> SEQ ID NO 36
<211> LENGTH: 636
<212> TYPE: DNA
<213> ORGANISM: human
<220> FEATURE:
<221> NAME/KEY: Unsure
<222> LOCATION: (332)..(332)
<223> OTHER INFORMATION: n = g, a, c, t or u
<220> FEATURE:
<221> NAME/KEY: misc_feature
<222> LOCATION: (332)..(332)
<223> OTHER INFORMATION: n is a, c, g, t or u

<400> SEQUENCE: 36

```
gggtctcgtt ctcgggagcc tatggctttg cagctgaccc agagtccagc tgacacccag      60
gcaggcagtc agggtctgtc tacaccccca ttgcaggagg agccgacaaa cagcagatgg     120
acgctgagct gcggaaggag atgatggcga tttggcccaa tctgtcccag aagacgctag     180
acctgctggt cacacctcac aagtgtaaga gctgagccca gccctgggat ccaatccacc     240
aggacagatg gaggggagg gaaaggggag gcctgggag agtgttggct gggctggtat     300
acacagggac ccaggacaag gtccccaaag angcctgccc ttggtgagct caccgtgtgt     360
gtcccccagc cacggacctc accgtgggga agatctacgc agccatgatg atcatggagt     420
actaccggca gagcaaggcc aagaagctgc aggccatgcg cgaggagcag gtgcgctgtt     480
cgccgctctg gggacatctg ggctgggac agtggcttgc atgtcaccac gggaaccaac     540
tggaatatga gggtggctga gccccagggc aggtccctga aaagtagggg ctggtgcaca     600
gcagctcaca cctgcaatct cagtgctttg agaggc                              636
```

<210> SEQ ID NO 37
<211> LENGTH: 829
<212> TYPE: DNA
<213> ORGANISM: human

<400> SEQUENCE: 37

```
gatcttcagg gccatgggag ctgcaggaag gactctggct ttttccccaa gcaagtggga      60
gccatggagg gttctaagca aaggagggat aggacctgac tcaagtgctc atgggcgccc     120
tctggtggct cttgtggaac agtggggttg aaggtaggag cgggagacct gggagaaggt     180
```

```
gcctgcagtg agagatgagg acgcgggacc aggctggggc tatgacttgg gtggaggagt      240
gagaagtggt ccagttctgc gtggaattgg aagggtctag atggatgaga cctgagagag      300
tgtgtgtgtg tgtgtgtgtg tatactgggg atgtcgcaat gccttctggg taccaccgtc      360
caccacccca cccttgtcca cacactgctc tctgccccat tccccaggac cggacacccc      420
tcatgttcca gcgcatggag ccccgtccc caacgcagga aggggacct ggccagaacg        480 ccctcccctc cacccagctg gacccaggag gagccctgtg agtgtcaccc ctgccaggga     540
ggtggagtgt ggggtgccg tggtccccac gttctggaag ctgccaagc gcccactgct       600 accccggcct ctgtccccca tgcaggatgg ctcacgaaag cggcctcaag gagagcccgt     660
cctgggtgac ccagcgtgcc caggagatgt tccagaagac gggcacatgg agtccggaac    720
aaggcccccc taccgacatg cccaacagcc agcctaactc tcaggtgcct ctgtccccca     780
actccccaat ggctcccagg gcccgggtgg ttgcggtgga aggaaccat                829

<210> SEQ ID NO 38
<211> LENGTH: 801
<212> TYPE: DNA
<213> ORGANISM: human
<220> FEATURE:
<221> NAME/KEY: Unsure
<222> LOCATION: (161)..(161)
<223> OTHER INFORMATION: n = g, a, c, t or u
<220> FEATURE:
<221> NAME/KEY: misc_feature
<222> LOCATION: (161)..(161)
<223> OTHER INFORMATION: n is a, c, g, t or u

<400> SEQUENCE: 38
tcactgcaac ctccaccttc cagtctcaag tgattcctcc tgcctcagcc tcccaagtca     60
ctggattaca ggcgcccacc accatgctca ggtatttttt tttgtatttt tagtagagac    120
ggggtttcac aatgttggtc aggctggtct cgaactgctg nccattgtga tctggaggtc   180
aggccccaga gctcatctgg cttttgccatt cgtccgcagt ccgtggagat gcgagagatg   240
ggcagagatg gctactccga cagcgagcac tacctcccca tggaaggcca gggccgggct   300
gcctccatgc cccgcctccc tgcagagaac caggtgaggg ctttcaccac tgccctgggg   360
ctggacccct cactctgcac tgggtagggc caggcccccc cacaagcagc ccagtgcatc   420
ccctcctgcc ggactcaggc ctgggtaggg actccttcag tctctgaagc agtctgcagg   480
ccccacccac cacctggtca cacctggagc acctgcagac cctcctccct cacagaggac   540
agagaggaaa gtgctccccc tggggcagag ggcagtggcc actgcaaaat ggtctctggc   600
tgccctggtt ggaggctgca gacagggag gttgtgaar atttgtgggt gcagcaggt     660 tcaacagggc cagctgagac ctgccacgaa gawcctttga ggccaggagt ttgagaccag   720
gttgggcaac atagcaaaac cctgtctctt tttttttttt gagacggagt ttcactcttg   780
ttgccccagg ctggagtgac a                                             801

<210> SEQ ID NO 39
<211> LENGTH: 329
<212> TYPE: DNA
<213> ORGANISM: human
<220> FEATURE:
<221> NAME/KEY: Unsure
<222> LOCATION: (177)..(177)
<223> OTHER INFORMATION: n = g, a, c, t or u
<220> FEATURE:
<221> NAME/KEY: misc_feature
<222> LOCATION: (177)..(177)
```

<223> OTHER INFORMATION: n is a, c, g, t or u

<400> SEQUENCE: 39

| | |
|---|---|
| cctcctcact cttccctctt gcctttatat ttattttctt ctttctgttt tttctgtgtg | 60 |
| caccatccat ggggctgtga cagaggagaa ggggccggcc acgtgggaat aacctcagtg | 120 |
| tatgtacggc ctgcccaggg cccagcaggc tccggccccc tcttcctccc caccccncct | 180 |
| ccagggagtc ccgtaatctc taccggtccc cggaccccac cctttctttg gcaatcgcac | 240 |
| cctctcccct ccatggagcc caatccttgt gtgtggtgtc ctgtgtgtgc cctgacccat | 300 |
| aagcctggtg gggcggccat ccccatcct | 329 |

<210> SEQ ID NO 40
<211> LENGTH: 554
<212> TYPE: DNA
<213> ORGANISM: human

<400> SEQUENCE: 40

| | |
|---|---|
| gatcaggggg agccaaggcc ccatggcatc ccctggcccc tgccccagga tggtcacacc | 60 |
| gcagtcaccg aaggccacca ccaggctgcc acaatgggc aggaaggacc gggaccactt | 120 |
| ggtgctagct gctgacccca gcccaccggc ctgtcccctc ccccagacca tctcagacac | 180 |
| cagccccatg aagcgttcag cctccgtgct gggcccaag gcccgacgcc tggacgatta | 240 |
| ctcgctggag cgggtcccgc ccgaggagaa ccagcggcac caccagcggc gccgcgaccg | 300 |
| cagccaccgc gcctctgagc gctccctggg ccgctacacc gatgtggaca caggtgggca | 360 |
| gccctgtggt gctcagggac aagcagaaca gaggagagga gagggagga gaaggcaggg | 420 |
| cggaggagac actaaggaag aagaaaggga gaggcctcca tggagagggg acagagcggg | 480 |
| ccaggcagcg gctgcaggaa cctgggtact acccctccc cccaacccac tgacctgcct | 540 |
| cggttcaggg gatc | 554 |

<210> SEQ ID NO 41
<211> LENGTH: 461
<212> TYPE: DNA
<213> ORGANISM: human

<400> SEQUENCE: 41

| | |
|---|---|
| ctgtgtgctg tctgaccctc acccggccca ggcttgggga cagacctgag catgaccacc | 60 |
| caatccgggg acctgccgtc gaaggagcgg gaccaggagc ggggccggcc caaggatcgg | 120 |
| aagcatcgac agcaccacca ccaccaccac caccaccacc atccccgcc cccgacaag | 180 |
| gaccgctatg cccaggaacg gccggaccac ggccgggcac gggctcggga ccagcgctgg | 240 |
| tcccgctcgc ccagcgaggg ccgagagcac atggcgcacc ggcaggtggg tgcggctgca | 300 |
| agtgacccca ggctgggctc ggccgggagg cggggaggag agaagggat accccatcca | 360 |
| acagccactc taggcaaagg tccccggatc ccggctgtga ccacctccca tcctgccccc | 420 |
| aagccaccgg ggtgcccggc ggccggagcg gagcacggat c | 461 |

<210> SEQ ID NO 42
<211> LENGTH: 664
<212> TYPE: DNA
<213> ORGANISM: HUMAN

<400> SEQUENCE: 42

| | |
|---|---|
| tttctcattt ctcttttcac ttttgttgtg ttggtttccg actcctcccc tccctgtctc | 60 |
| actcccccctc ctcccctccc tcctccctgt ggctgttgct ttttccatt caatgtcctg | 120 |

-continued

```
tgtcccccct ctcctcctcc tcctcctcct cccctcctc cctctcctcc cggcccctct    180
cccttcgctc ccctcatctt cctcccaatc ccgtgtctcc tttgattttg ttgtatcttt    240
ttttttgatt tcctttgttt caattttcgt gtagggcagt agttccgtaa gtggaagccc    300 agcccctca acatctggta ccagcactcc gcggcgggc cgccgccagc tcccccagac     360 ccctccacc ccccggccac acgtgtccta ttcccctgtg atccgtaagg ccggcggctc     420 ggggccccg cagcagcagc agcagcagca gcagcagcag caggcggtgg ccaggccggc     480
cgggcggcca ccagcggccc tcggaggtac ccaggcccca cggccgagcc tctggccgga    540
gatcggcgcc cacgggggc cacagcagcg gccgcacgcc caggatggag aggcgggtcc     600
aggcccggcc cggagcgagt ctccagggcc tggtcgacac ggcggggccc ggctggcggc    660
agtc                                                                 664

<210> SEQ ID NO 43
<211> LENGTH: 6789
<212> TYPE: DNA
<213> ORGANISM: HUMAN

<400> SEQUENCE: 43
atggcccgct tcggagacga gatgccggcc cgctacgggg gaggaggctc cggggcagcc     60
gccggggtgg tcgtgggcag cggaggcggg cgaggagccg gggcagccg gcagggcggg    120 cagcccgggg cgcaaaggat gtacaagcag tcaatggcgc agagagcgcg gaccatggca    180
ctctacaacc ccatccccgt ccgacagaac tgcctcacgg ttaaccggtc tctcttcctc    240
ttcagcgaag acaacgtggt gagaaaatac gccaaaaaga tcaccgaatg cctcccttt    300 gaatatatga ttttagccac catcatagcg aattgcatcg tcctcgcact ggagcagcat    360
ctgcctgatg atgacaagac cccgatgtct gaacggctgg atgacacaga accatacttc    420
attggaattt tttgtttcga ggctggaatt aaaatcattg cccttgggtt tgccttccac    480
aaaggctcct acttgaggaa tggctggaat gtcatggact tgtggtggt gctaacgggc    540 atcttggcga cagttgggac ggagtttgac ctacggacgc tgagggcagt tcgagtgctg    600
cggccgctca agctggtgtc tggaatccca gtttacaag tcgtcctgaa gtcgatcatg    660
aaggcgatga tcccttttgct gcagatcggc ctcctcctat ttttgcaat ccttattttt    720 gcaatcatag ggttagaatt ttatatggga aaatttcata ccacctgctt tgaagagggg    780
acagatgaca ttcagggtga gtctccggct ccatgtggga cagaagagcc cgcccgcacc    840
tgccccaatg ggaccaaatg tcagccctac tgggaagggc ccaacaacgg gatcactcag    900
ttcgacaaca tcctgttttgc agtgctgact gttttccagt gcataaccat ggaagggtgg    960
actgatctcc tctacaatag caacgatgcc tcagggaaca cttggaactg gttgtacttc   1020
atccccctca tcatcatcgg ctccttttttt atgctgaacc ttgtgctggg tgtgctgtca   1080
ggggagtttg ccaaagaaag ggaacgggtg gagaaccggc gggcttttct gaagctgagg   1140
cggcaacaac agattgaacg tgagctcaat gggtacatgg aatggatctc aaaagcagaa   1200
gaggtgatcc tcgccgagga tgaaactgac ggggagcaga ggcatcccct tgatggagct   1260
ctgcggagaa ccaccataaa gaaaagcaag acagatttgc tcaaccccga agaggctgag   1320
gatcagctgg ctgatatagc ctctgtgggt tctcccttcg cccgagccag cattaaaagt   1380
gccaagctgg agaactcgac cttttttcac aaaaaggaga ggaggatgcg tttctacatc   1440
cgccgcatgg tcaaaactca ggccttctac tggactgtac tcagtttggt agctctcaac   1500
```

-continued

```
acgctgtgtg ttgctattgt tcactacaac cagcccgagt ggctctccga cttcctttac    1560
tatgcagaat tcattttctt aggactcttt atgtccgaaa tgtttataaa aatgtacggg    1620
cttgggacgc ggccttactt ccactcttcc ttcaactgct ttgactgtgg ggttatcatt    1680
gggagcatct tcgaggtcat ctgggctgtc ataaaacctg gcacatcctt tggaatcagc    1740
gtgttacgag ccctcaggtt attgcgtatt ttcaaagtca caaagtactg ggcatctctc    1800
agaaacctgg tcgtctctct cctcaactcc atgaagtcca tcatcagcct gttgtttctc    1860
cttttcctgt tcattgtcgt cttcgcccct ttgggaatgc aactcttcgg cggccagttt    1920
aatttcgatg aagggactcc tcccaccaac ttcgatactt tccagcagc aataatgacg     1980 gtgtttcaga tcctgacggg cgaagactgg aacgaggtca tgtacgacgg gatcaagtct    2040 cagggggcg tgcagggcgg catggtgttc tccatctatt tcattgtact gacgctcttt     2100
gggaactaca ccctcctgaa tgtgttcttg gccatcgctg tggacaatct ggccaacgcc    2160
caggagctca ccaaggacga gcaagaggaa gaagaagcag cgaaccagaa acttgcccta    2220
cagaaagcca aggaggtggc agaagtgagt cctctgtccg cggccaacat gtctatagct    2280
gtgaaagagc aacagaagaa tcaaaagcca gccaagtccg tgtgggagca gcggaccagt    2340
gagatgcgaa agcagaactt gctggccagc cgggaggccc tgtataacga aatggacccg    2400
gacgagcgct ggaaggctgc ctacacgcgg cacctgcggc cagacatgaa gacgcacttg    2460
gaccggccgc tggtggtgga cccgcaggag aaccgcaaca acaacaccaa caagagccgg    2520
gcggccgagc ccaccgtgga ccagcgcctc ggccagcagc gcgccgagga cttcctcagg    2580
aaacaggccc gctaccacga tcgggcccgg accccagcg gctcggcggg cctggacgca    2640
cggaggccct gggcgggaag ccaggaggcc gagctgagcc gggaggaccc ctacggccgc    2700
gagtcggacc accacgcccg ggagggcagc ctggagcaac ccgggttctg ggagggcgag    2760
gccgagcgag gcaaggccgg ggaccccac cggaggcacg tgcaccggca gggggcagc      2820 agggagagcc gcagcgggtc cccgcgcacg ggcgcggacg gggagcatcg acgtcatcgc    2880
gcgcaccgca ggcccgggga ggagggtccg gaggacaagg cggagcggag ggcgcggcac    2940
cgcgagggca gccggccggc ccggggcggc gagggcgagg gcgaggtcc cgacggggc      3000 gagcgcagga gaaggcaccg gcatggcgct ccagccacgt acgaggggga cgcgcggagg    3060
gaggacaagg agcggaggca tcggaggagg aaagagaacc agggctccgg ggtccctgtg    3120
tcgggcccca acctgtcaac cacccggcca atccagcagg acctgggccg ccaagaccca    3180
cccctggcag aggatattga caacatgaag aacaacaagc tggccaccgc ggagtcggcc    3240
gctccccacg gcagccttgg ccacgccggc ctgcccagc gcccagccaa gatgggaaac     3300
agcaccgacc ccggccccat gctggccatc cctgccatgg ccaccaaccc ccagaacgcc    3360
gccagccgcc ggacgcccaa caacccgggg aacccatcca atcccggccc cccaagacc     3420 cccgagaata gccttatcgt caccaacccc agcggcaccc agaccaattc agctaagact    3480
gccaggaaac ccgaccacac cacagtggac atcccccag cctgcccacc ccccctcaac     3540
cacaccgtcg tacaagtgaa caaaaacgcc aacccagacc cactgccaaa aaagaggaa     3600 gagaagaagg aggaggagga agaagacgac cgtggggaag acggccctaa gccaatgcct    3660
ccctatagct ccatgttcat cctgtccacg accaaccccc ttcgccgcct gtgccattac    3720
atcctgaacc tgcgctactt tgagatgtgc atcctcatgg tcattgccat gagcagcatc    3780
gccctggccg ccgaggaccc tgtgcagccc aacgcacctc ggaacaacgt gctgcgatac    3840
tttgactacg tttttacagg cgtctttacc tttgagatgg tgatcaagat gattgacctg    3900
```

-continued

```
gggctcgtcc tgcatcaggg tgcctacttc cgtgacctct ggaatattct cgacttcata   3960
gtggtcagtg gggccctggt agcctttgcc ttcactggca atagcaaagg aaaagacatc   4020
aacacgatta atccctccg  agtcctccgg gtgctacgac ctcttaaaac catcaagcgg   4080
ctgccaaagc tcaaggctgt gtttgactgt gtggtgaact cacttaaaaa cgtcttcaac   4140
atcctcatcg tctacatgct attcatgttc atcttcgccg tggtggctgt gcagctcttc   4200
aaggggaaat tcttccactg cactgacgag tccaaagagt ttgagaaaga ttgtcgaggc   4260
aaataccctcc tctacgagaa gaatgaggtg aaggcgcgag accgggagtg gaagaagtat   4320
gaattccatt acgacaatgt gctgtgggct ctgctgaccc tcttcaccgt gtccacggca   4380
gaaggctggc cacaggtcct caagcattcg gtggacgcca cctttgagaa ccagggcccc   4440
agccccgggt accgcatgga gatgtccatt ttctacgtcg tctactttgt ggtgttcccc   4500
ttcttctttg tcaatatctt tgtggccttg atcatcatca ccttccagga gcaaggggac   4560
aagatgatgg aggaatacag cctggagaaa atgagaggg  cctgcattga tttcgccatc   4620
agtgccaagc cgctgacccg acacatgccg cagaacaagc agagcttcca gtaccgcatg   4680
tggcagttcg tggtgtctcc gccttt cgag tacacgatca tggccatgat cgccctcaac   4740
accatcgtgc ttatgatgaa gttctatggg gcttctgtgg cttatgaaaa tgccctgcgg   4800
gtgttcaaca tcgccttcac ctccctcttc tctctggaat gtgtgctgaa agccatggct   4860
tttgggattc tgaattattt ccgcgatgcc tggaacatct tcgactttgt gactgttctg   4920
ggcagcatca ccgatatcct cgtgactgag tttgggaata acttcatcaa cctgagcttt   4980
ctccgcctct tccgagctgc ccggctcatc aaacttctcc gtcagggtta caccatccgc   5040
attcttctct ggaccttgt  gcagtccttc aaggccctgc cttatgtctg tctgctgatc   5100
gccatgctct tcttcatcta tgccatcatt gggatgcagg tgtttggtaa cattggcatc   5160
gacgtggagg acgaggacag tgatgaagat gagttccaaa tcactgagca caataacttc   5220
cggaccttct tccaggcccct catgcttctc ttccggagtg ccaccgggga agcttggcac   5280
aacatcatgc tttcctgcct cagcgggaaa ccgtgtgata agaactctgg catcctgact   5340
cgagagtgtg gcaatgaatt tgcttatttt tactttgttt ccttcatctt cctctgctcg   5400
tttctgatgc tgaatctctt tgtcgccgtc atcatggaca actttgagta cctcacccga   5460
gactcctcca tcctgggccc ccaccacctg gatgagtacg tgcgtgtctg ggccgagtat   5520
gacccccgcag cttgcggtcg gattcattat aaggatatgt acagtttatt acgagtaata   5580
tctccccctc tcggcttagg caagaaatgt cctcataggg ttgcttgcaa gcggcttctg   5640
cggatggacc tgcccgtcgc agatgacaac ccgtccact  tcaattccac cctcatggct   5700
ctgatccgca cagccctgga catcaagatt gccaagggag gagccgacaa acagcagatg   5760
gacgctgagc tgcggaagga gatgatggcg atttggccca atctgtccca gaagacgcta   5820
gacctgctgg tcacacctca caagtccacg gacctcaccg tggggaagat ctacgcagcc   5880
atgatgatca tggagtacta ccggcagagc aaggccaaga agctgcaggc catgcgcgag   5940
gagcaggacc ggacacccct catgttccag cgcatggagc cccgtccccc aacgcaggaa   6000
ggggacctg  gccagaacgc cctcccctcc acccagctgg acccaggagg agccctgatg   6060
gctcacgaaa gcggcctcaa ggagagcccg tcctgggtga cccagcgtgc caggagatg   6120
ttccagaaga cgggcacatg gagtccggaa caaggccccc ctaccgacat gcccaacagc   6180
cagcctaact ctcagtccgt ggagatgcga gagatgggca gagatggcta ctccgacagc   6240
```

-continued

```
gagcactacc tccccatgga aggccagggc cgggctgcct ccatgcccg cctccctgca    6300 gagaaccaga ggagaagggg ccggccacgt gggaataacc tcagtaccat ctcagacacc    6360
agccccatga agccgttcagc ctccgtgctg gccccaagg cccgacgcct ggacgattac    6420
tcgctggagc gggtcccgcc cgaggagaac cagcggcacc accagcggcg ccgcgaccgc    6480
agccaccgcg cctctgagcg ctccctgggc cgctacaccg atgtggacac aggcttgggg    6540
acagacctga gcatgaccac ccaatccggg gacctgccgt cgaaggagcg ggaccaggag    6600
cggggccggc ccaaggatcg gaagcatcga cagcaccacc accaccacca ccaccaccac    6660 catccccgc cccccgacaa ggaccgctat gcccaggaac ggccggacca cggccgggca    6720
cgggctcggg accagcgctg gtcccgctcg cccagcgagg gccgagagca catggcgcac    6780
cggcagtag                                                              6789
```

<210> SEQ ID NO 44
<211> LENGTH: 2262
<212> TYPE: PRT
<213> ORGANISM: human

<400> SEQUENCE: 44

```
Met Ala Arg Phe Gly Asp Glu Met Pro Ala Arg Tyr Gly Gly Gly Gly
1               5                   10                  15

Ser Gly Ala Ala Ala Gly Val Val Gly Ser Gly Gly Gly Arg Gly
            20                  25                  30

Ala Gly Gly Ser Arg Gln Gly Gly Gln Pro Gly Ala Gln Arg Met Tyr
        35                  40                  45

Lys Gln Ser Met Ala Gln Arg Ala Arg Thr Met Ala Leu Tyr Asn Pro
    50                  55                  60

Ile Pro Val Arg Gln Asn Cys Leu Thr Val Asn Arg Ser Leu Phe Leu
65                  70                  75                  80

Phe Ser Glu Asp Asn Val Val Arg Lys Tyr Ala Lys Lys Ile Thr Glu
                85                  90                  95

Trp Pro Pro Phe Glu Tyr Met Ile Leu Ala Thr Ile Ile Ala Asn Cys
            100                 105                 110

Ile Val Leu Ala Leu Glu Gln His Leu Pro Asp Asp Asp Lys Thr Pro
        115                 120                 125

Met Ser Glu Arg Leu Asp Asp Thr Glu Pro Tyr Phe Ile Gly Ile Phe
    130                 135                 140

Cys Phe Glu Ala Gly Ile Lys Ile Ile Ala Leu Gly Phe Ala Gly His
145                 150                 155                 160

Lys Gly Ser Tyr Leu Arg Asn Gly Trp Asn Val Met Asp Phe Val Val
                165                 170                 175

Val Leu Thr Gly Ile Leu Ala Thr Val Gly Thr Glu Phe Asp Leu Arg
            180                 185                 190

Thr Leu Arg Ala Val Arg Val Leu Arg Pro Leu Lys Leu Val Ser Gly
        195                 200                 205

Ile Pro Ser Leu Gln Val Val Leu Lys Ser Ile Met Lys Ala Met Ile
    210                 215                 220

Pro Leu Leu Gln Ile Gly Leu Leu Leu Phe Phe Ala Ile Leu Ile Phe
225                 230                 235                 240

Ala Ile Ile Gly Leu Glu Phe Tyr Met Gly Lys Phe His Thr Thr Cys
                245                 250                 255

Phe Glu Glu Gly Thr Asp Asp Ile Gln Gly Glu Ser Pro Ala Pro Cys
            260                 265                 270
```

```
Gly Thr Glu Glu Pro Ala Arg Thr Cys Pro Asn Gly Thr Lys Cys Gln
        275                 280                 285

Pro Tyr Trp Glu Gly Pro Asn Asn Gly Ile Thr Gln Phe Asp Asn Ile
        290                 295                 300

Leu Phe Ala Val Leu Thr Val Phe Gln Cys Ile Thr Met Glu Gly Trp
305                 310                 315                 320

Thr Asp Leu Leu Tyr Asn Ser Asn Asp Ala Ser Gly Asn Thr Trp Asn
                325                 330                 335

Trp Leu Tyr Phe Ile Pro Leu Ile Ile Ile Gly Ser Phe Phe Met Leu
                340                 345                 350

Asn Leu Val Leu Gly Val Leu Ser Gly Glu Phe Ala Lys Glu Phe Glu
                355                 360                 365

Arg Val Glu Asn Arg Arg Ala Phe Leu Lys Leu Arg Arg Gln Gln Gln
        370                 375                 380

Ile Glu Arg Glu Leu Asn Gly Tyr Met Glu Trp Ile Ser Lys Ala Glu
385                 390                 395                 400

Glu Val Ile Leu Ala Glu Asp Glu Thr Asp Gly Glu Gln Arg His Pro
                405                 410                 415

Phe Asp Gly Ala Leu Arg Arg Thr Thr Ile Lys Lys Ser Lys Thr Asp
                420                 425                 430

Leu Leu Asn Pro Glu Glu Ala Glu Asp Gln Leu Ala Asp Ile Ala Ser
                435                 440                 445

Val Gly Ser Pro Phe Ala Arg Ala Ser Ile Lys Ser Ala Lys Leu Glu
        450                 455                 460

Asn Ser Thr Phe Phe His Lys Lys Glu Arg Arg Met Arg Phe Tyr Ile
465                 470                 475                 480

Arg Arg Met Val Lys Thr Gln Ala Phe Tyr Trp Thr Val Leu Ser Leu
                485                 490                 495

Val Ala Leu Asn Thr Leu Cys Val Ala Ile Val His Tyr Asn Gln Pro
                500                 505                 510

Glu Trp Leu Ser Asp Phe Leu Tyr Tyr Ala Glu Phe Ile Phe Leu Gly
        515                 520                 525

Leu Phe Met Ser Glu Met Phe Ile Lys Met Tyr Gly Leu Gly Thr Arg
530                 535                 540

Pro Tyr Phe His Ser Ser Phe Asn Cys Phe Asp Cys Gly Val Ile Ile
545                 550                 555                 560

Gly Ser Ile Phe Glu Val Ile Trp Ala Val Ile Lys Pro Gly Thr Ser
                565                 570                 575

Phe Gly Ile Ser Val Leu Arg Ala Leu Arg Leu Leu Arg Ile Phe Lys
                580                 585                 590

Val Thr Lys Tyr Trp Ala Ser Leu Arg Asn Leu Val Val Ser Leu Leu
        595                 600                 605

Asn Ser Met Lys Ser Ile Ile Ser Leu Leu Phe Leu Leu Phe Leu Phe
610                 615                 620

Ile Val Val Phe Ala Leu Leu Gly Met Gln Leu Phe Gly Gly Gln Phe
625                 630                 635                 640

Asn Phe Asp Glu Gly Thr Pro Pro Thr Asn Phe Asp Thr Phe Pro Ala
                645                 650                 655

Ala Ile Met Thr Val Phe Gln Ile Leu Thr Gly Glu Asp Trp Asn Glu
                660                 665                 670

Val Met Tyr Asp Gly Ile Lys Ser Gln Gly Gly Val Gln Gly Gly Met
        675                 680                 685

Val Phe Ser Ile Tyr Phe Ile Val Leu Thr Leu Phe Gly Asn Tyr Thr
```

```
                    690              695              700
Leu Leu Asn Val Phe Leu Ala Ile Ala Val Asp Asn Leu Ala Asn Ala
705              710              715              720
Gln Glu Leu Thr Lys Asp Glu Gln Glu Glu Glu Ala Ala Asn Gln
            725              730              735
Lys Leu Ala Leu Gln Lys Ala Lys Glu Val Ala Glu Val Ser Pro Leu
            740              745              750
Ser Ala Ala Asn Met Ser Ile Ala Val Lys Glu Gln Gln Lys Asn Gln
            755              760              765
Lys Pro Ala Lys Ser Val Trp Glu Gln Arg Thr Ser Glu Met Arg Lys
770              775              780
Gln Asn Leu Leu Ala Ser Arg Glu Ala Leu Tyr Asn Glu Met Asp Pro
785              790              795              800
Asp Glu Arg Trp Lys Ala Ala Tyr Thr Arg His Leu Arg Pro Asp Met
            805              810              815
Lys Thr His Leu Asp Arg Pro Leu Val Asp Pro Gln Glu Asn Arg
            820              825              830
Asn Asn Asn Thr Asn Lys Ser Arg Ala Ala Glu Pro Thr Val Asp Gln
            835              840              845
Arg Leu Gly Gln Gln Arg Ala Glu Asp Phe Leu Arg Lys Gln Ala Arg
850              855              860
Tyr His Asp Arg Ala Arg Asp Pro Ser Gly Ser Ala Gly Leu Asp Ala
865              870              875              880
Arg Arg Pro Trp Ala Gly Ser Gln Glu Ala Glu Leu Ser Arg Glu Asp
            885              890              895
Pro Tyr Gly Arg Glu Ser Asp His His Ala Arg Glu Gly Ser Leu Glu
            900              905              910
Gln Pro Gly Phe Trp Glu Gly Glu Ala Glu Arg Gly Lys Ala Gly Asp
            915              920              925
Pro His Arg Arg His Val His Arg Gln Gly Gly Ser Arg Glu Ser Arg
            930              935              940
Ser Gly Ser Pro Arg Thr Gly Ala Asp Gly Glu His Arg Arg His Arg
945              950              955              960
Ala His Arg Arg Pro Gly Glu Glu Gly Pro Glu Asp Lys Ala Glu Arg
            965              970              975
Arg Ala Arg His Arg Glu Gly Ser Arg Pro Ala Arg Gly Gly Glu Gly
            980              985              990
Glu Gly Glu Gly Pro Asp Gly Gly Glu Arg Arg Arg His Arg His
            995              1000             1005
Gly Ala Pro Ala Thr Tyr Glu Gly Asp Ala Arg Arg Glu Asp Lys
            1010             1015             1020
Glu Arg Arg His Arg Arg Lys Glu Asn Gln Gly Ser Gly Val
            1025             1030             1035
Pro Val Ser Gly Pro Asn Leu Ser Thr Thr Arg Pro Ile Gln Gln
            1040             1045             1050
Asp Leu Gly Arg Gln Asp Pro Pro Leu Ala Glu Asp Ile Asp Asn
            1055             1060             1065
Met Lys Asn Asn Lys Leu Ala Thr Ala Glu Ser Ala Ala Pro His
            1070             1075             1080
Gly Ser Leu Gly His Ala Gly Leu Pro Gln Ser Pro Ala Lys Met
            1085             1090             1095
Gly Asn Ser Thr Asp Pro Gly Pro Met Leu Ala Ile Pro Ala Met
            1100             1105             1110
```

-continued

```
Ala Thr Asn Pro Gln Asn Ala Ala Ser Arg Arg Thr Pro Asn Asn
    1115                1120                1125
Pro Gly Asn Pro Ser Asn Pro Gly Pro Pro Lys Thr Pro Glu Asn
    1130                1135                1140
Ser Leu Ile Val Thr Asn Pro Ser Gly Thr Gln Thr Asn Ser Ala
    1145                1150                1155
Lys Thr Ala Arg Lys Pro Asp His Thr Thr Val Asp Ile Pro Pro
    1160                1165                1170
Ala Cys Pro Pro Pro Leu Asn His Thr Val Val Gln Val Asn Lys
    1175                1180                1185
Asn Ala Asn Pro Asp Pro Leu Pro Lys Lys Glu Glu Glu Lys Lys
    1190                1195                1200
Glu Glu Glu Glu Glu Asp Asp Arg Gly Glu Asp Gly Pro Lys Pro
    1205                1210                1215
Met Pro Pro Tyr Ser Ser Met Phe Ile Leu Ser Thr Thr Asn Pro
    1220                1225                1230
Leu Arg Arg Leu Cys His Tyr Ile Leu Asn Leu Arg Tyr Phe Glu
    1235                1240                1245
Met Cys Ile Leu Met Val Ile Ala Met Ser Ser Ile Ala Leu Ala
    1250                1255                1260
Ala Glu Asp Pro Val Gln Pro Asn Ala Pro Arg Asn Asn Val Leu
    1265                1270                1275
Arg Tyr Phe Asp Tyr Val Phe Thr Gly Val Phe Thr Phe Glu Met
    1280                1285                1290
Val Ile Lys Met Ile Asp Leu Gly Leu Val Leu His Gln Gly Ala
    1295                1300                1305
Tyr Phe Arg Asp Leu Trp Asn Ile Leu Asp Phe Ile Val Val Ser
    1310                1315                1320
Gly Ala Leu Val Ala Phe Ala Phe Thr Gly Asn Ser Lys Gly Lys
    1325                1330                1335
Asp Ile Asn Thr Ile Lys Ser Leu Arg Val Leu Arg Val Leu Arg
    1340                1345                1350
Pro Leu Lys Thr Ile Lys Arg Leu Pro Lys Leu Lys Ala Val Phe
    1355                1360                1365
Asp Cys Val Val Asn Ser Leu Lys Asn Val Phe Asn Ile Leu Ile
    1370                1375                1380
Val Tyr Met Leu Phe Met Phe Ile Phe Ala Val Val Ala Val Gln
    1385                1390                1395
Leu Phe Lys Gly Lys Phe Phe His Cys Thr Asp Glu Ser Lys Glu
    1400                1405                1410
Phe Glu Lys Asp Cys Arg Gly Lys Tyr Leu Leu Tyr Glu Lys Asn
    1415                1420                1425
Glu Val Lys Ala Arg Asp Arg Glu Trp Lys Lys Tyr Glu Phe His
    1430                1435                1440
Tyr Asp Asn Val Leu Trp Ala Leu Leu Thr Leu Phe Thr Val Ser
    1445                1450                1455
Thr Ala Glu Gly Trp Pro Gln Val Leu Lys His Ser Val Asp Ala
    1460                1465                1470
Thr Phe Glu Asn Gln Gly Pro Ser Pro Gly Tyr Arg Met Glu Met
    1475                1480                1485
Ser Ile Phe Tyr Val Val Tyr Phe Val Val Phe Pro Phe Phe Phe
    1490                1495                1500
```

-continued

| | | | | | | | | | | | |
|---|---|---|---|---|---|---|---|---|---|---|---|
| Val | Asn | Ile | Phe | Val | Ala | Leu | Ile | Ile | Thr | Phe | Gln | Glu | Gln |
| 1505 | | | | 1510 | | | | 1515 | | | |

Gly Asp Lys Met Met Glu Glu Tyr Ser Leu Glu Lys Asn Glu Arg
1520                     1525                    1530

Ala Cys Ile Asp Phe Ala Ile Ser Ala Lys Pro Leu Thr Arg His
1535                     1540                    1545

Met Pro Gln Asn Lys Gln Ser Phe Gln Tyr Arg Met Trp Gln Phe
1550                     1555                    1560

Val Val Ser Pro Pro Phe Glu Tyr Thr Ile Met Ala Met Ile Ala
1565                     1570                    1575

Leu Asn Thr Ile Val Leu Met Met Lys Phe Tyr Gly Ala Ser Val
1580                     1585                    1590

Ala Tyr Glu Asn Ala Leu Arg Val Phe Asn Ile Ala Phe Thr Ser
1595                     1600                    1605

Leu Phe Ser Leu Glu Cys Val Leu Lys Ala Met Ala Phe Gly Ile
1610                     1615                    1620

Leu Asn Tyr Phe Arg Asp Ala Trp Asn Ile Phe Asp Phe Val Thr
1625                     1630                    1635

Val Leu Gly Ser Ile Thr Asp Ile Leu Val Thr Glu Phe Gly Asn
1640                     1645                    1650

Asn Phe Ile Asn Leu Ser Phe Leu Arg Leu Phe Arg Ala Ala Arg
1655                     1660                    1665

Leu Ile Lys Leu Leu Arg Gln Gly Tyr Thr Ile Arg Ile Leu Leu
1670                     1675                    1680

Trp Thr Phe Val Gln Ser Phe Lys Ala Leu Pro Tyr Val Cys Leu
1685                     1690                    1695

Leu Ile Ala Met Leu Phe Phe Ile Tyr Ala Ile Ile Gly Met Gln
1700                     1705                    1710

Val Phe Gly Asn Ile Gly Ile Asp Val Glu Asp Glu Asp Ser Asp
1715                     1720                    1725

Glu Asp Glu Phe Gln Ile Thr Glu His Asn Asn Phe Arg Thr Phe
1730                     1735                    1740

Phe Gln Ala Leu Met Leu Leu Phe Arg Ser Ala Thr Gly Glu Ala
1745                     1750                    1755

Trp His Asn Ile Met Leu Ser Cys Leu Ser Gly Lys Pro Cys Asp
1760                     1765                    1770

Lys Asn Ser Gly Ile Leu Thr Arg Glu Cys Gly Asn Glu Phe Ala
1775                     1780                    1785

Tyr Phe Tyr Phe Val Ser Phe Ile Phe Leu Cys Ser Phe Leu Met
1790                     1795                    1800

Leu Asn Leu Phe Val Ala Val Ile Met Asp Asn Phe Glu Tyr Leu
1805                     1810                    1815

Thr Arg Asp Ser Ser Ile Leu Gly Pro His His Leu Asp Glu Tyr
1820                     1825                    1830

Val Arg Val Trp Ala Glu Tyr Asp Pro Ala Ala Cys Gly Arg Ile
1835                     1840                    1845

His Tyr Lys Asp Met Tyr Ser Leu Leu Arg Val Ile Ser Pro Pro
1850                     1855                    1860

Leu Gly Leu Gly Lys Lys Cys Pro His Arg Val Ala Cys Lys Arg
1865                     1870                    1875

Leu Leu Arg Met Asp Leu Pro Val Ala Asp Asp Asn Thr Val His
1880                     1885                    1890

Phe Asn Ser Thr Leu Met Ala Leu Ile Arg Thr Ala Leu Asp Ile

```
                    1895             1900             1905
Lys Ile Ala Lys Gly Gly Ala Asp Lys Gln Gln Met Asp Ala Glu
    1910             1915             1920

Leu Arg Lys Glu Met Met Ala Ile Trp Pro Asn Leu Ser Gln Lys
    1925             1930             1935

Thr Leu Asp Leu Leu Val Thr Pro His Lys Ser Thr Asp Leu Thr
    1940             1945             1950

Val Gly Lys Ile Tyr Ala Ala Met Met Ile Met Glu Tyr Tyr Arg
    1955             1960             1965

Gln Ser Lys Ala Lys Lys Leu Gln Ala Met Arg Glu Glu Gln Asp
    1970             1975             1980

Arg Thr Pro Leu Met Phe Gln Arg Met Glu Pro Pro Ser Pro Thr
    1985             1990             1995

Gln Glu Gly Gly Pro Gly Gln Asn Ala Leu Pro Ser Thr Gln Leu
    2000             2005             2010

Asp Pro Gly Gly Ala Leu Met Ala His Glu Ser Gly Leu Lys Glu
    2015             2020             2025

Ser Pro Ser Trp Val Thr Gln Arg Ala Gln Glu Met Phe Gln Lys
    2030             2035             2040

Thr Gly Thr Trp Ser Pro Glu Gln Gly Pro Pro Thr Asp Met Pro
    2045             2050             2055

Asn Ser Gln Pro Asn Ser Gln Ser Val Glu Met Arg Glu Met Gly
    2060             2065             2070

Arg Asp Gly Tyr Ser Asp Ser Glu His Tyr Leu Pro Met Glu Gly
    2075             2080             2085

Gln Gly Arg Ala Ala Ser Met Pro Arg Leu Pro Ala Glu Asn Gln
    2090             2095             2100

Arg Arg Arg Gly Arg Pro Arg Gly Asn Asn Leu Ser Thr Ile Ser
    2105             2110             2115

Asp Thr Ser Pro Met Lys Arg Ser Ala Ser Val Leu Gly Pro Lys
    2120             2125             2130

Ala Arg Arg Leu Asp Asp Tyr Ser Leu Glu Arg Val Pro Pro Glu
    2135             2140             2145

Glu Asn Gln Arg His His Gln Arg Arg Arg Asp Arg Ser His Arg
    2150             2155             2160

Ala Ser Glu Arg Ser Leu Gly Arg Tyr Thr Asp Val Asp Thr Gly
    2165             2170             2175

Leu Gly Thr Asp Leu Ser Met Thr Thr Gln Ser Gly Asp Leu Pro
    2180             2185             2190

Ser Lys Glu Arg Asp Gln Glu Arg Gly Arg Pro Lys Asp Arg Lys
    2195             2200             2205

His Arg Gln His His His His His His His His His Pro Pro
    2210             2215             2220

Pro Pro Asp Lys Asp Arg Tyr Ala Gln Glu Arg Pro Asp His Gly
    2225             2230             2235

Arg Ala Arg Ala Arg Asp Gln Arg Trp Ser Arg Ser Pro Ser Glu
    2240             2245             2250

Gly Arg Glu His Met Ala His Arg Gln
    2255             2260

<210> SEQ ID NO 45
<211> LENGTH: 20
<212> TYPE: DNA
<213> ORGANISM: human
```

```
<400> SEQUENCE: 45
caacatcatg ctttcctgcc                                               20

<210> SEQ ID NO 46
<211> LENGTH: 20
<212> TYPE: DNA
<213> ORGANISM: human

<400> SEQUENCE: 46
atgatgacgg cgacaaagag                                               20

<210> SEQ ID NO 47
<211> LENGTH: 40
<212> TYPE: DNA
<213> ORGANISM: human

<400> SEQUENCE: 47
tctccgcagt cgtagctcca cgcaaaggat gtacaagcag                         40

<210> SEQ ID NO 48
<211> LENGTH: 41
<212> TYPE: DNA
<213> ORGANISM: human

<400> SEQUENCE: 48
ggttgtagag tgccatggtc attcccaagc ctccagggta g                       41

<210> SEQ ID NO 49
<211> LENGTH: 20
<212> TYPE: DNA
<213> ORGANISM: HUMAN

<400> SEQUENCE: 49 acctccaac acccttcttt                                                20

<210> SEQ ID NO 50
<211> LENGTH: 19
<212> TYPE: DNA
<213> ORGANISM: HUMAN

<400> SEQUENCE: 50
tctgtgccct gctccactc                                                19

<210> SEQ ID NO 51
<211> LENGTH: 20
<212> TYPE: DNA
<213> ORGANISM: HUMAN

<400> SEQUENCE: 51
acgctgacct tgccttctct                                               20

<210> SEQ ID NO 52
<211> LENGTH: 20
<212> TYPE: DNA
<213> ORGANISM: HUMAN

<400> SEQUENCE: 52
caaccaaaag cctcgtaatc                                               20

<210> SEQ ID NO 53
<211> LENGTH: 20
<212> TYPE: DNA
```

<213> ORGANISM: HUMAN

<400> SEQUENCE: 53
aaaacccacc ctctgttctc                                           20

<210> SEQ ID NO 54
<211> LENGTH: 20
<212> TYPE: DNA
<213> ORGANISM: HUMAN

<400> SEQUENCE: 54
ttgtcagggt cggaaactca                                           20

<210> SEQ ID NO 55
<211> LENGTH: 16
<212> TYPE: DNA
<213> ORGANISM: HUMAN

<400> SEQUENCE: 55
cttggtggcg gggttt                                               16

<210> SEQ ID NO 56
<211> LENGTH: 20
<212> TYPE: DNA
<213> ORGANISM: HUMAN

<400> SEQUENCE: 56
ctgcctaatc ctcccaagag                                           20

<210> SEQ ID NO 57
<211> LENGTH: 20
<212> TYPE: DNA
<213> ORGANISM: HUMAN

<400> SEQUENCE: 57
tcccttccct tttgtagatg                                           20

<210> SEQ ID NO 58
<211> LENGTH: 19
<212> TYPE: DNA
<213> ORGANISM: HUMAN

<400> SEQUENCE: 58
gtggggctgt gttgtcctt                                            19

<210> SEQ ID NO 59
<211> LENGTH: 20
<212> TYPE: DNA
<213> ORGANISM: HUMAN

<400> SEQUENCE: 59
gacagagcca caagagaacc                                           20

<210> SEQ ID NO 60
<211> LENGTH: 20
<212> TYPE: DNA
<213> ORGANISM: HUMAN

<400> SEQUENCE: 60
agcaaagagg agtgagtggg                                           20

<210> SEQ ID NO 61
<211> LENGTH: 20

-continued

<210> SEQ ID NO 61
<211> LENGTH: 20
<212> TYPE: DNA
<213> ORGANISM: HUMAN

<400> SEQUENCE: 61
atactctggc ttttctatgc                                              20

<210> SEQ ID NO 62
<211> LENGTH: 20
<212> TYPE: DNA
<213> ORGANISM: HUMAN

<400> SEQUENCE: 62
gcatgactct ctttgtactc                                              20

<210> SEQ ID NO 63
<211> LENGTH: 17
<212> TYPE: DNA
<213> ORGANISM: HUMAN

<400> SEQUENCE: 63
gcagagaatg ggggtgg                                                 17

<210> SEQ ID NO 64
<211> LENGTH: 20
<212> TYPE: DNA
<213> ORGANISM: HUMAN

<400> SEQUENCE: 64
ctgaggtggg tttagagcag                                              20

<210> SEQ ID NO 65
<211> LENGTH: 22
<212> TYPE: DNA
<213> ORGANISM: HUMAN

<400> SEQUENCE: 65
gggtaacgtc tttttctctt gc                                           22

<210> SEQ ID NO 66
<211> LENGTH: 20
<212> TYPE: DNA
<213> ORGANISM: HUMAN

<400> SEQUENCE: 66
atgtctcttg ggcgataggt                                              20

<210> SEQ ID NO 67
<211> LENGTH: 20
<212> TYPE: DNA
<213> ORGANISM: HUMAN

<400> SEQUENCE: 67
atttcttctg aaggaacagc                                              20

<210> SEQ ID NO 68
<211> LENGTH: 20
<212> TYPE: DNA
<213> ORGANISM: HUMAN

<400> SEQUENCE: 68
ggagggatca gggagttggc                                              20

<210> SEQ ID NO 69

```
<211> LENGTH: 20
<212> TYPE: DNA
<213> ORGANISM: HUMAN

<400> SEQUENCE: 69
caagcctaac ctcctctctg                                                 20

<210> SEQ ID NO 70
<211> LENGTH: 19
<212> TYPE: DNA
<213> ORGANISM: HUMAN

<400> SEQUENCE: 70
tcattccagg caagagctg                                                  19

<210> SEQ ID NO 71
<211> LENGTH: 20
<212> TYPE: DNA
<213> ORGANISM: HUMAN

<400> SEQUENCE: 71
atttggaggg aggagtttgg                                                 20

<210> SEQ ID NO 72
<211> LENGTH: 20
<212> TYPE: DNA
<213> ORGANISM: HUMAN

<400> SEQUENCE: 72
tcactttccc aactttctgg                                                 20

<210> SEQ ID NO 73
<211> LENGTH: 20
<212> TYPE: DNA
<213> ORGANISM: HUMAN

<400> SEQUENCE: 73
cagaaagttg ggaaagtagc                                                 20

<210> SEQ ID NO 74
<211> LENGTH: 19
<212> TYPE: DNA
<213> ORGANISM: HUMAN

<400> SEQUENCE: 74
ttgaattcct gtgaaggac                                                  19

<210> SEQ ID NO 75
<211> LENGTH: 21
<212> TYPE: DNA
<213> ORGANISM: HUMAN

<400> SEQUENCE: 75
cttggagatg agatactgag c                                               21

<210> SEQ ID NO 76
<211> LENGTH: 20
<212> TYPE: DNA
<213> ORGANISM: HUMAN

<400> SEQUENCE: 76
caggcacttt catctgtgac                                                 20
```

-continued

```
<210> SEQ ID NO 77
<211> LENGTH: 20
<212> TYPE: DNA
<213> ORGANISM: HUMAN

<400> SEQUENCE: 77
tccacagctg catctccaag                                              20

<210> SEQ ID NO 78
<211> LENGTH: 18
<212> TYPE: DNA
<213> ORGANISM: HUMAN

<400> SEQUENCE: 78
accctccctt gagcccct                                                18

<210> SEQ ID NO 79
<211> LENGTH: 20
<212> TYPE: DNA
<213> ORGANISM: HUMAN

<400> SEQUENCE: 79
cagtggttgc ttttcctgac                                              20

<210> SEQ ID NO 80
<211> LENGTH: 20
<212> TYPE: DNA
<213> ORGANISM: HUMAN

<400> SEQUENCE: 80
ttgccagaga aacattctcc                                              20

<210> SEQ ID NO 81
<211> LENGTH: 20
<212> TYPE: DNA
<213> ORGANISM: HUMAN

<400> SEQUENCE: 81
tgaacaaaga ttccacgtgc                                              20

<210> SEQ ID NO 82
<211> LENGTH: 21
<212> TYPE: DNA
<213> ORGANISM: HUMAN

<400> SEQUENCE: 82
ttcaggagcc agggtagcat c                                            21

<210> SEQ ID NO 83
<211> LENGTH: 59
<212> TYPE: DNA
<213> ORGANISM: HUMAN

<400> SEQUENCE: 83
tagcaatgct ctaagtcctg cgcaggagaa ccgcaacaag cagcagggag agccgcagc   59

<210> SEQ ID NO 84
<211> LENGTH: 58
<212> TYPE: DNA
<213> ORGANISM: HUMAN

<400> SEQUENCE: 84
tgtttcctga ggaagtcctc gcgatgacgt cgatgctcta ccgtcattct gcggattc    58
```

-continued

```
<210> SEQ ID NO 85
<211> LENGTH: 41
<212> TYPE: DNA
<213> ORGANISM: HUMAN

<400> SEQUENCE: 85
ggttcttttt cattcacttg cgagaatagc cttatcgtca c        41

<210> SEQ ID NO 86
<211> LENGTH: 39
<212> TYPE: DNA
<213> ORGANISM: HUMAN

<400> SEQUENCE: 86
tttcctggca gtcttagctg cagtgatgtg agagcagag          39

<210> SEQ ID NO 87
<211> LENGTH: 20
<212> TYPE: DNA
<213> ORGANISM: HUMAN

<400> SEQUENCE: 87
tgggaaattg tggagggagc                               20

<210> SEQ ID NO 88
<211> LENGTH: 20
<212> TYPE: DNA
<213> ORGANISM: HUMAN

<400> SEQUENCE: 88
tgacttccgc caccctggtg                               20

<210> SEQ ID NO 89
<211> LENGTH: 21
<212> TYPE: DNA
<213> ORGANISM: HUMAN

<400> SEQUENCE: 89
taggaagggg tgtgctctgt g                             21

<210> SEQ ID NO 90
<211> LENGTH: 20
<212> TYPE: DNA
<213> ORGANISM: HUMAN

<400> SEQUENCE: 90
agcctgtggt ctgagtggac                               20

<210> SEQ ID NO 91
<211> LENGTH: 20
<212> TYPE: DNA
<213> ORGANISM: HUMAN

<400> SEQUENCE: 91
atccactgct ctcttgcttt                               20

<210> SEQ ID NO 92
<211> LENGTH: 22
<212> TYPE: DNA
<213> ORGANISM: HUMAN

<400> SEQUENCE: 92
gtggttctca cttataatct gc                            22
```

```
<210> SEQ ID NO 93
<211> LENGTH: 21
<212> TYPE: DNA
<213> ORGANISM: HUMAN

<400> SEQUENCE: 93
tggcctcatt ggcttccctg c                                              21

<210> SEQ ID NO 94
<211> LENGTH: 20
<212> TYPE: DNA
<213> ORGANISM: HUMAN

<400> SEQUENCE: 94
aagaggaaac ccttgcgaag                                                20

<210> SEQ ID NO 95
<211> LENGTH: 20
<212> TYPE: DNA
<213> ORGANISM: HUMAN

<400> SEQUENCE: 95
ctacccaacc tgacctctgc                                                20

<210> SEQ ID NO 96
<211> LENGTH: 20
<212> TYPE: DNA
<213> ORGANISM: HUMAN

<400> SEQUENCE: 96
acatgataac cctgacagtc                                                20

<210> SEQ ID NO 97
<211> LENGTH: 20
<212> TYPE: DNA
<213> ORGANISM: HUMAN

<400> SEQUENCE: 97
ctcatgctct ctgtcaactc                                                20

<210> SEQ ID NO 98
<211> LENGTH: 20
<212> TYPE: DNA
<213> ORGANISM: HUMAN

<400> SEQUENCE: 98
tggttccaat gggaatgtgc                                                20

<210> SEQ ID NO 99
<211> LENGTH: 20
<212> TYPE: DNA
<213> ORGANISM: HUMAN

<400> SEQUENCE: 99
ctgcttccca agcagtctag                                                20

<210> SEQ ID NO 100
<211> LENGTH: 20
<212> TYPE: DNA
<213> ORGANISM: HUMAN

<400> SEQUENCE: 100
```

-continued tcctggatag atttccagtc                                                    20

<210> SEQ ID NO 101
<211> LENGTH: 20
<212> TYPE: DNA
<213> ORGANISM: HUMAN

<400> SEQUENCE: 101
agtttttaaa ggacagatgg                                                    20

<210> SEQ ID NO 102
<211> LENGTH: 22
<212> TYPE: DNA
<213> ORGANISM: HUMAN

<400> SEQUENCE: 102
tttccctgcc ccattccttt gc                                                 22

<210> SEQ ID NO 103
<211> LENGTH: 20
<212> TYPE: DNA
<213> ORGANISM: HUMAN

<400> SEQUENCE: 103
ctctgccgct ctcaccactg                                                    20

<210> SEQ ID NO 104
<211> LENGTH: 19
<212> TYPE: DNA
<213> ORGANISM: HUMAN

<400> SEQUENCE: 104
tttatcaggt agaggcagg                                                     19

<210> SEQ ID NO 105
<211> LENGTH: 21
<212> TYPE: DNA
<213> ORGANISM: HUMAN

<400> SEQUENCE: 105
ttccaagccc atagctgtag c                                                  21

<210> SEQ ID NO 106
<211> LENGTH: 21
<212> TYPE: DNA
<213> ORGANISM: HUMAN

<400> SEQUENCE: 106
tgaccctgct actcctgctt c                                                  21

<210> SEQ ID NO 107
<211> LENGTH: 20
<212> TYPE: DNA
<213> ORGANISM: HUMAN

<400> SEQUENCE: 107
actgtgcctc taacatgcac                                                    20

<210> SEQ ID NO 108
<211> LENGTH: 18
<212> TYPE: DNA
<213> ORGANISM: HUMAN

<400> SEQUENCE: 108
aagtgctggc tcaagcag                                                    18

<210> SEQ ID NO 109
<211> LENGTH: 20
<212> TYPE: DNA
<213> ORGANISM: HUMAN

<400> SEQUENCE: 109
tctgtgagtg gtgacagctc                                                  20

<210> SEQ ID NO 110
<211> LENGTH: 18
<212> TYPE: DNA
<213> ORGANISM: HUMAN

<400> SEQUENCE: 110
gtcacctgtc ttctcagc                                                    18

<210> SEQ ID NO 111
<211> LENGTH: 20
<212> TYPE: DNA
<213> ORGANISM: HUMAN

<400> SEQUENCE: 111
tggaaggact ctggcacgtg                                                  20

<210> SEQ ID NO 112
<211> LENGTH: 20
<212> TYPE: DNA
<213> ORGANISM: HUMAN

<400> SEQUENCE: 112
ggaggctctg ggaaccttag                                                  20

<210> SEQ ID NO 113
<211> LENGTH: 21
<212> TYPE: DNA
<213> ORGANISM: HUMAN

<400> SEQUENCE: 113
agaagccact ggaggaatgg c                                                21

<210> SEQ ID NO 114
<211> LENGTH: 22
<212> TYPE: DNA
<213> ORGANISM: HUMAN

<400> SEQUENCE: 114
attatcagag caggtcccct tc                                               22

<210> SEQ ID NO 115
<211> LENGTH: 20
<212> TYPE: DNA
<213> ORGANISM: HUMAN

<400> SEQUENCE: 115
tccgagtctc tgatttctcc                                                  20

<210> SEQ ID NO 116
<211> LENGTH: 19
<212> TYPE: DNA
<213> ORGANISM: HUMAN

```
<400> SEQUENCE: 116
agacggccct cacagtgtc                                            19

<210> SEQ ID NO 117
<211> LENGTH: 20
<212> TYPE: DNA
<213> ORGANISM: HUMAN

<400> SEQUENCE: 117
ttcattccct cggtctctgc                                           20

<210> SEQ ID NO 118
<211> LENGTH: 19
<212> TYPE: DNA
<213> ORGANISM: HUMAN

<400> SEQUENCE: 118
ctgactgaac ctgtgagac                                            19

<210> SEQ ID NO 119
<211> LENGTH: 19
<212> TYPE: DNA
<213> ORGANISM: HUMAN

<400> SEQUENCE: 119
tgtgaaccca ttgcctgca                                            19

<210> SEQ ID NO 120
<211> LENGTH: 19
<212> TYPE: DNA
<213> ORGANISM: HUMAN

<400> SEQUENCE: 120
tgggaatgac tgcgcttgc                                            19

<210> SEQ ID NO 121
<211> LENGTH: 18
<212> TYPE: DNA
<213> ORGANISM: HUMAN

<400> SEQUENCE: 121
atgcctggga atgactgc                                             18

<210> SEQ ID NO 122
<211> LENGTH: 18
<212> TYPE: DNA
<213> ORGANISM: HUMAN

<400> SEQUENCE: 122
tgtcacgcct gtctgtgc                                             18

<210> SEQ ID NO 123
<211> LENGTH: 18
<212> TYPE: DNA
<213> ORGANISM: HUMAN

<400> SEQUENCE: 123
tgacacccag gcaggcag                                             18

<210> SEQ ID NO 124
<211> LENGTH: 18
<212> TYPE: DNA
<213> ORGANISM: HUMAN
```

<400> SEQUENCE: 124
tctgacgcct gtctgtgc                                                18

<210> SEQ ID NO 125
<211> LENGTH: 18
<212> TYPE: DNA
<213> ORGANISM: HUMAN

<400> SEQUENCE: 125
ttggtgagct caccgtgt                                                18

<210> SEQ ID NO 126
<211> LENGTH: 21
<212> TYPE: DNA
<213> ORGANISM: HUMAN

<400> SEQUENCE: 126
ttcccgtggt gacatgcaag c                                            21

<210> SEQ ID NO 127
<211> LENGTH: 20
<212> TYPE: DNA
<213> ORGANISM: HUMAN

<400> SEQUENCE: 127
gtccacacac tgctctctgc                                              20

<210> SEQ ID NO 128
<211> LENGTH: 18
<212> TYPE: DNA
<213> ORGANISM: HUMAN

<400> SEQUENCE: 128
acactccacc tccctggc                                                18

<210> SEQ ID NO 129
<211> LENGTH: 18
<212> TYPE: DNA
<213> ORGANISM: HUMAN

<400> SEQUENCE: 129
gccagggagg tggagtgt                                                18

<210> SEQ ID NO 130
<211> LENGTH: 18
<212> TYPE: DNA
<213> ORGANISM: HUMAN

<400> SEQUENCE: 130
ggttccttcc accgcaac                                                18

<210> SEQ ID NO 131
<211> LENGTH: 17
<212> TYPE: DNA
<213> ORGANISM: HUMAN

<400> SEQUENCE: 131
caactcccca atggctc                                                 17

<210> SEQ ID NO 132
<211> LENGTH: 21
<212> TYPE: DNA

<213> ORGANISM: HUMAN

<400> SEQUENCE: 132
cctacccagt gcagagtgag g    21

<210> SEQ ID NO 133
<211> LENGTH: 20
<212> TYPE: DNA
<213> ORGANISM: HUMAN

<400> SEQUENCE: 133
tctgtgtgca ccatcccatg    20

<210> SEQ ID NO 134
<211> LENGTH: 20
<212> TYPE: DNA
<213> ORGANISM: HUMAN

<400> SEQUENCE: 134 aaggatttggg ctccatggag    20

<210> SEQ ID NO 135
<211> LENGTH: 19
<212> TYPE: DNA
<213> ORGANISM: HUMAN

<400> SEQUENCE: 135
gttggtgcta gctgctgac    19

<210> SEQ ID NO 136
<211> LENGTH: 20
<212> TYPE: DNA
<213> ORGANISM: HUMAN

<400> SEQUENCE: 136
ctttcttctt ccttagtgtc    20

<210> SEQ ID NO 137
<211> LENGTH: 20
<212> TYPE: DNA
<213> ORGANISM: HUMAN

<400> SEQUENCE: 137
gtgtgctgtc tgaccctcac    20

<210> SEQ ID NO 138
<211> LENGTH: 20
<212> TYPE: DNA
<213> ORGANISM: HUMAN

<400> SEQUENCE: 138
agcctggggt cacttgcagc    20

<210> SEQ ID NO 139
<211> LENGTH: 23
<212> TYPE: DNA
<213> ORGANISM: HUMAN

<400> SEQUENCE: 139
cctttgtttc aattttcgtg tag    23

<210> SEQ ID NO 140
<211> LENGTH: 20

-continued

```
<212> TYPE: DNA
<213> ORGANISM: HUMAN

<400> SEQUENCE: 140
tggggcctgg gtacctccga                                           20

<210> SEQ ID NO 141
<211> LENGTH: 19
<212> TYPE: DNA
<213> ORGANISM: HUMAN

<400> SEQUENCE: 141
ctttaattgc cctgtcttc                                            19

<210> SEQ ID NO 142
<211> LENGTH: 18
<212> TYPE: DNA
<213> ORGANISM: HUMAN

<400> SEQUENCE: 142
ttaattcgac cacttccc                                             18

<210> SEQ ID NO 143
<211> LENGTH: 20
<212> TYPE: DNA
<213> ORGANISM: HUMAN

<400> SEQUENCE: 143
agtgagactc gtctctaatg                                           20

<210> SEQ ID NO 144
<211> LENGTH: 20
<212> TYPE: DNA
<213> ORGANISM: HUMAN

<400> SEQUENCE: 144
acctacctga attcctgacc                                           20

<210> SEQ ID NO 145
<211> LENGTH: 22
<212> TYPE: DNA
<213> ORGANISM: HUMAN

<400> SEQUENCE: 145
aacactagtg acattatttt ca                                        22

<210> SEQ ID NO 146
<211> LENGTH: 20
<212> TYPE: DNA
<213> ORGANISM: HUMAN

<400> SEQUENCE: 146
agctaggcct gaaggcttct                                           20
```